United States Patent [19]
Justice et al.

[11] Patent Number: 5,824,645
[45] Date of Patent: Oct. 20, 1998

[54] METHOD OF TREATING INFLAMMATION

[75] Inventors: Alan Justice, Sunnyvale; Tejinder Singh, Palo Alto; Kishor Chandra Gohil, Richmond; Karen L. Valentino, San Carlos; George P. Miljanich, Redwood City, all of Calif.

[73] Assignee: Neurex Corporation, Menlo Park, Calif.

[21] Appl. No.: 742,774

[22] Filed: Nov. 1, 1996

Related U.S. Application Data

[63] Continuation of Ser. No. 675,354, Jul. 3, 1996, which is a continuation of Ser. No. 49,794, Apr. 15, 1993, Pat. No. 5,587,454, which is a continuation-in-part of Ser. No. 814,759, Dec. 30, 1991, abandoned.

[51] Int. Cl.$^6$ .......................... A61K 38/00; A61K 38/02; C07K 5/00; C07K 7/00
[52] U.S. Cl. .................................. 514/12; 514/21; 514/13; 514/14; 514/15; 530/321; 530/324; 530/325; 530/326
[58] Field of Search .................................. 514/12, 13, 14, 514/15, 21; 530/324, 325, 326, 327

[56] References Cited

U.S. PATENT DOCUMENTS

| | | | |
|---|---|---|---|
| 4,975,446 | 12/1990 | Trager et al. | 514/363 |
| 5,189,020 | 2/1993 | Miljanich et al. | 514/12 |
| 5,587,454 | 12/1996 | Justice et al. | 530/324 |

OTHER PUBLICATIONS

Andersson, S.E. and Le Greves, P., "Ruthenium Red and Capsaicin Induce a Neurogenic Inflammatory Response in the Rabbit Eye: Effects of ω–conotoxin GVIA and tetrodotoxin," *Eur. J. Pharmacol.*, 209:175–183 (1991).

*Primary Examiner*—Avis M. Davenport
*Attorney, Agent, or Firm*—Carol A. Stratford; Peter J. Dehlinger

[57] ABSTRACT

A method of producing analgesia in nociceptive and neuropathic pain is disclosed. The method includes administering to a subject an omega conopeptide which is characterized by its ability to (a) inhibit electrically stimulated contraction of the guinea pig ileum, and (b) bind selectively to omega conopeptide MVIIA binding sites present in neuronal tissue. Also disclosed are novel omega conotoxin peptides effective in producing analgesia.

9 Claims, 26 Drawing Sheets

|  | 1 | 5 | 10 | 15 | 20 | 25 | 30 |
|---|---|---|---|---|---|---|---|
| MVIIA/SNX-111 | C | K G K G A K | C S R L M Y D | C C T G S C | - R - S G K | - C |  |
| MVIIB/SNX-159 | C | K G K G A S C | H R T S Y D | C C T G S C | N R - - G K | - C |  |
| GVIA/SNX-124 | C | K S X G S S C | S X T S Y N | C C R - - S | C N X Y T - | K R C - - Y |  |
| GVIIB/SNX-178 | C | K S X G T X C | S R G M R D | C C T - - S | C L L Y S N K | - C R R Y |  |
| RVIA/SNX-182 | C | K P X G S X C | R V S S Y N | C C S - - S | C K S Y - N K K | C G |  |

Fig. 1A

| | 1 | | | | 5 | | | | | 10 | | | | | 15 | | | | | 20 | | | | | 25 | | | | | 30 |
|---|---|---|---|---|---|---|---|---|---|---|---|---|---|---|---|---|---|---|---|---|---|---|---|---|---|---|---|---|---|---|
| SVIA/SNX-157 | C | R | S | S | G | S | X | C | G | V | T | S | I | - | C | C | - | G | R | C | - | I | - | Y | R | G | K | - | C | T |
| TVIA/SNX-185 | C | L | S | X | G | S | S | C | S | X | T | S | Y | N | C | C | R | - | S | C | N | X | Y | S | - | R | K | C | R |
| SVIB/SNX-183 | C | K | L | K | G | Q | S | C | R | K | T | S | Y | D | C | C | S | G | S | C | G | R | - | S | G | K | - | C | |
| MVIIC/SNX-230 | C | K | G | K | G | A | P | C | R | K | T | M | Y | D | C | C | S | G | S | C | G | R | - | R | G | K | - | C | |
| SNX-231 | C | K | G | K | G | A | X | C | R | K | T | M | Y | D | C | C | S | G | S | C | G | R | - | R | G | K | - | C | |

Fig. 1B

| | 1 | | | | 5 | | | | | 10 | | | | | 15 | | | | | 20 | | | | | 25 | |
|---|---|---|---|---|---|---|---|---|---|---|---|---|---|---|---|---|---|---|---|---|---|---|---|---|---|---|
| MVIIA (SNX-111) | C | K | G | K | G | A | K | C | S | R | L | M | Y | D | C | C | T | G | S | C | R | S | G | K | C-NH$_2$ |
| SNX-190 | - | - | - | - | A | - | - | - | - | - | - | - | - | - | - | - | - | - | - | - | - | - | - | - | NH$_2$ |
| SNX-191 | - | A | - | - | - | - | - | - | - | - | - | - | - | - | - | - | - | - | - | - | - | - | - | - | NH$_2$ |
| SNX-193 | - | - | - | - | - | - | - | - | - | - | - | - | - | - | - | - | - | - | - | - | - | - | - | - | G-OH |
| SNX-194 | - | - | - | - | - | - | - | - | - | - | - | Nle | - | - | - | - | - | - | - | - | - | - | - | - | NH$_2$ |
| SNX-195 | - | - | - | - | - | - | - | - | - | - | - | - | - | - | - | - | - | - | - | - | - | - | - | A | NH$_2$ |
| SNX-196 | N- | - | - | - | - | - | - | - | - | - | - | - | - | - | - | - | - | - | - | - | - | - | - | - | G-OH |
| SNX-197 | NS- | - | - | - | - | - | - | - | - | - | - | - | - | - | - | - | - | - | - | - | - | - | - | - | NH$_2$ |
| SNX-198 | - | - | - | - | - | - | - | - | - | - | - | - | - | - | - | - | - | - | - | - | - | A | - | - | NH$_2$ |
| SNX-199 | - | - | - | - | - | - | - | - | - | A | - | - | - | - | - | - | - | - | - | - | - | - | - | - | NH$_2$ |

Fig. 2A

| | 1 | | 5 | | | | | 10 | | | | | 15 | | | | | 20 | | | | | 25 | |
|---|---|---|---|---|---|---|---|---|---|---|---|---|---|---|---|---|---|---|---|---|---|---|---|---|
| SNX-200 | | | | A | | | | | | | | | | | | | | | | | | | | NH$_2$ |
| SNX-201 | | | | | | | R | K | T | S | | | | | | | | | | | | | | NH$_2$ |
| SNX-239 | | | | | | | | | L | | | | | | | | | | | | | | | NH$_2$ |
| SNX-240 Ac- | | | | | | | | | L | | | | | | | | | | | | | | | NH$_2$ |
| SVIB (SNX-183) | C | L | K | G | Q | S | C | R | K | T | S | Y | D | C | C | S | G | S | C | G | R | S | G | K | C NH$_2$ |
| SNX-202 | | | | | | | | | | S | R | L | M | | | | | | | | | | | | NH$_2$ |
| TVIA (SNX-185) | C | L | S | X | G | S | S | C | S | X | T | S | Y | N | C | C | R | S | C | N | X | Y | S | R K | C R NH$_2$ |
| SNX-207 | | | | | | | | | | R | L | M | | | | | | | | | | | | | NH$_2$ |
| SNX-236 | | | | | | | | | | R | L | M | | | | | | | P | | | | | | NH$_2$ |

Fig. 2B

ROSTRAL SECTIONS CAUDAL SECTIONS
*111
 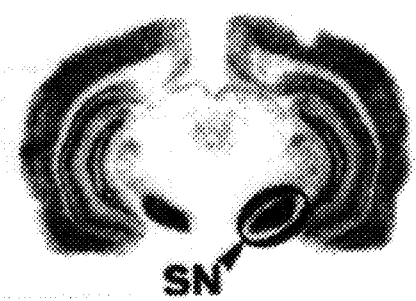
Fig. 12A  Fig. 12B
*111
+
excess
111
Fig. 12C  Fig. 12D
*183
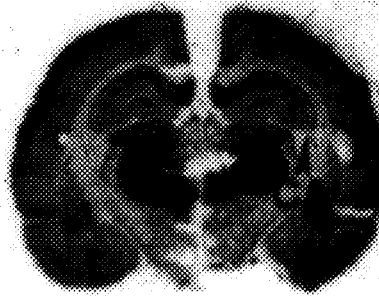 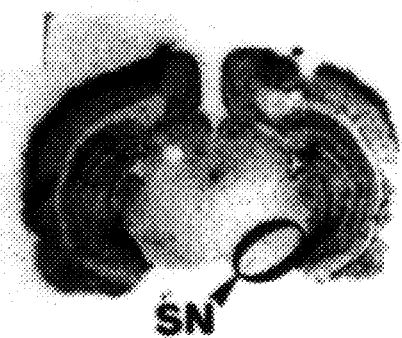
Fig. 12E  Fig. 12F
*183
+
excess
183
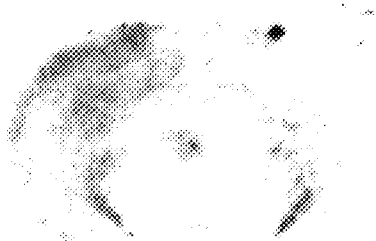
Fig. 12G  Fig. 12H

Fig. 14

| | 1 | | | | 5 | | | | | 10 | | | | | 15 | | | | | 20 | | | | | 25 | | | | | 30 | |
|---|---|---|---|---|---|---|---|---|---|---|---|---|---|---|---|---|---|---|---|---|---|---|---|---|---|---|---|---|---|---|---|
| I. | | | | | | | | | | | | | | | | | | | | | | | | | | | | | | | |
| MVIIA | C | K | G | K | G | A | K | C | S | R | L | M | Y | D | C | C | T | G | S | C | - | R | - | S | G | K | - | C | | | |
| SNX-239 | C | K | G | K | G | A | K | C | S | L | L | M | Y | D | C | C | T | G | S | C | - | R | - | S | G | K | - | C | | | |
| SNX-199 | C | K | G | K | G | A | K | C | S | A | L | M | Y | D | C | C | T | G | S | C | - | R | - | S | G | K | - | C | | | |
| MVIIB | C | K | G | K | G | A | S | C | H | R | T | S | Y | D | C | C | T | G | S | C | N | R | - | - | G | K | - | C | | | |
| II. | | | | | | | | | | | | | | | | | | | | | | | | | | | | | | | |
| TVIA | C | L | S | X | G | S | S | C | S | X | T | S | Y | N | C | C | R | - | S | C | N | X | Y | S | R | K | - | C | R | | |
| SNX-207 | C | L | S | X | G | S | S | C | S | R | L | M | Y | N | C | C | R | - | S | C | N | X | Y | S | R | K | - | C | R | | |
| SNX-236 | C | L | S | X | G | S | S | C | S | R | L | M | Y | N | C | C | R | - | S | C | N | P | Y | S | R | K | - | C | R | | |
| III. | | | | | | | | | | | | | | | | | | | | | | | | | | | | | | | |
| RVIA | C | K | P | X | G | S | X | C | R | V | S | S | Y | N | C | C | S | - | S | C | K | S | Y | - | N | K | K | C | G | | |
| SVIA | C | R | S | S | G | S | X | C | R | G | V | T | S | H | I | C | C | - | G | R | C | - | Y | R | G | K | - | C | T | | |
| GVIIA | C | K | S | X | G | T | X | C | S | R | G | M | R | D | C | C | T | - | S | S | C | L | L | Y | S | N | K | C | R | R | Y D |
| SVIB | C | K | L | K | G | Q | S | C | R | K | T | M | Y | D | C | C | S | G | S | C | G | R | - | S | G | K | - | C | | | |
| MVIIC | C | K | G | K | G | A | P | C | R | K | T | M | Y | D | C | C | S | G | S | C | G | R | - | R | G | K | - | C | | | |
| SNX-231 | C | K | G | K | G | A | X | C | R | K | T | M | Y | D | C | C | S | G | S | C | G | R | - | R | G | K | - | C | | | |

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: MVIIA/SNX- 111, FIGURE 1

( x i ) SEQUENCE DESCRIPTION: SEQ ID NO:1:

Cys Lys Gly Lys Gly Ala Lys Cys Ser Arg Leu Met Tyr Asp Cys Cys
1               5                           10                          15

Thr Gly Ser Cys Arg Ser Gly Lys Cys
              20                  25

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: MVIIB/SNX- 159, FIGURE 1

( x i ) SEQUENCE DESCRIPTION: SEQ ID NO:2:

Cys Lys Gly Lys Gly Ala Ser Cys His Arg Thr Ser Tyr Asp Cys Cys
1               5                           10                          15

Thr Gly Ser Cys Asn Arg Gly Lys Cys
              20                  25

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: GVIA/SNX- 124, FIGURE 1

( i x ) FEATURE:
        ( A ) NAME/KEY: Modified-site
        ( B ) LOCATION: 4
        ( D ) OTHER INFORMATION: /note= "where X is hydroxyproline"

( i x ) FEATURE:
        ( A ) NAME/KEY: Modified-site
        ( B ) LOCATION: 10
        ( D ) OTHER INFORMATION: /note= "where X is hydroxyproline"

( i x ) FEATURE:
        ( A ) NAME/KEY: Modified-site
        ( B ) LOCATION: 21
        ( D ) OTHER INFORMATION: /note= "where X is hydroxyproline"

( x i ) SEQUENCE DESCRIPTION: SEQ ID NO:3:

Cys Lys Ser Xaa Gly Ser Ser Cys Ser Xaa Thr Ser Tyr Asn Cys Cys
1               5                           10                          15

Arg Ser Cys Asn Xaa Tyr Thr Lys Arg Cys Tyr
              20                  25

( 2 ) INFORMATION FOR SEQ ID NO:4:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( i i i ) HYPOTHETICAL: NO (v i) ORIGINAL SOURCE:
       (C) INDIVIDUAL ISOLATE: GVIIA/SNX-178, FIGURE 1

(i x) FEATURE:
       (A) NAME/KEY: Modified-site
       (B) LOCATION: 4
       (D) OTHER INFORMATION: /note= "where X is hydroxyproline"

(i x) FEATURE:
       (A) NAME/KEY: Modified-site
       (B) LOCATION: 7
       (D) OTHER INFORMATION: /note= "where X is hydroxyproline"

(x i) SEQUENCE DESCRIPTION: SEQ ID NO:4:

Cys Lys Ser Xaa Gly Thr Xaa Cys Ser Arg Gly Met Arg Asp Cys Cys
1               5               10                  15

Thr Ser Cys Leu Leu Tyr Ser Asn Lys Cys Arg Arg Tyr
            20              25

(2) INFORMATION FOR SEQ ID NO:5:

(i) SEQUENCE CHARACTERISTICS:
       (A) LENGTH: 27 amino acids
       (B) TYPE: amino acid
       (D) TOPOLOGY: linear (i i) MOLECULE TYPE: protein (i i i) HYPOTHETICAL: NO (v i) ORIGINAL SOURCE:
       (C) INDIVIDUAL ISOLATE: RVIA/SNX-182, FIGURE 1

(i x) FEATURE:
       (A) NAME/KEY: Modified-site
       (B) LOCATION: 4
       (D) OTHER INFORMATION: /note= "where X is hydroxyproline"

(i x) FEATURE:
       (A) NAME/KEY: Modified-site
       (B) LOCATION: 7
       (D) OTHER INFORMATION: /note= "where X is hydroxyproline"

(x i) SEQUENCE DESCRIPTION: SEQ ID NO:5:

Cys Lys Pro Xaa Gly Ser Xaa Cys Arg Val Ser Ser Tyr Asn Cys Cys
1               5               10                  15

Ser Ser Cys Lys Ser Tyr Asn Lys Lys Cys Gly
            20              25

(2) INFORMATION FOR SEQ ID NO:6:

(i) SEQUENCE CHARACTERISTICS:
       (A) LENGTH: 24 amino acids
       (B) TYPE: amino acid
       (D) TOPOLOGY: linear (i i) MOLECULE TYPE: protein (i i i) HYPOTHETICAL: NO (v i) ORIGINAL SOURCE:
       (C) INDIVIDUAL ISOLATE: SVIA/SNX-157, FIGURE 1

(i x) FEATURE:
       (A) NAME/KEY: Modified-site
       (B) LOCATION: 7
       (D) OTHER INFORMATION: /note= "where X is hydroxyproline"

(x i) SEQUENCE DESCRIPTION: SEQ ID NO:6:

Cys Arg Ser Ser Gly Ser Xaa Cys Gly Val Thr Ser Ile Cys Cys Gly
1               5               10                  15

```
        Arg  Cys  Tyr  Arg  Gly  Lys  Cys  Thr
                      20
```

(2) INFORMATION FOR SEQ ID NO:7:

(i) SEQUENCE CHARACTERISTICS:
    (A) LENGTH: 27 amino acids
    (B) TYPE: amino acid
    (D) TOPOLOGY: linear (ii) MOLECULE TYPE: protein (iii) HYPOTHETICAL: NO (vi) ORIGINAL SOURCE:
    (C) INDIVIDUAL ISOLATE: TVIA/SNX- 185, FIGURE 1

(ix) FEATURE:
    (A) NAME/KEY: Modified-site
    (B) LOCATION: 4
    (D) OTHER INFORMATION: /note= "where X is hydroxyproline"

(ix) FEATURE:
    (A) NAME/KEY: Modified-site
    (B) LOCATION: 10
    (D) OTHER INFORMATION: /note= "where X is hydroxyproline"

(ix) FEATURE:
    (A) NAME/KEY: Modified-site
    (B) LOCATION: 21
    (D) OTHER INFORMATION: /note= "where X is hydroxyproline"

(xi) SEQUENCE DESCRIPTION: SEQ ID NO:7:

```
Cys  Leu  Ser  Xaa  Gly  Ser  Ser  Cys  Ser  Xaa  Thr  Ser  Tyr  Asn  Cys  Cys
  1                 5                        10                         15

Arg  Ser  Cys  Asn  Xaa  Tyr  Ser  Arg  Lys  Cys  Arg
              20                       25
```

(2) INFORMATION FOR SEQ ID NO:8:

(i) SEQUENCE CHARACTERISTICS:
    (A) LENGTH: 26 amino acids
    (B) TYPE: amino acid
    (D) TOPOLOGY: linear (ii) MOLECULE TYPE: protein (iii) HYPOTHETICAL: NO (vi) ORIGINAL SOURCE:
    (C) INDIVIDUAL ISOLATE: SVIB/SNX- 183, FIGURE 1

(xi) SEQUENCE DESCRIPTION: SEQ ID NO:8:

```
Cys  Lys  Leu  Lys  Gly  Gln  Ser  Cys  Arg  Lys  Thr  Ser  Tyr  Asp  Cys  Cys
  1                 5                        10                         15

Ser  Gly  Ser  Cys  Gly  Arg  Ser  Gly  Lys  Cys
              20                       25
```

(2) INFORMATION FOR SEQ ID NO:9:

(i) SEQUENCE CHARACTERISTICS:
    (A) LENGTH: 25 amino acids
    (B) TYPE: amino acid
    (D) TOPOLOGY: linear (ii) MOLECULE TYPE: protein (iii) HYPOTHETICAL: NO (vi) ORIGINAL SOURCE:
    (C) INDIVIDUAL ISOLATE: SNX-190, FIGURE 2

(xi) SEQUENCE DESCRIPTION: SEQ ID NO:9:

```
Cys Lys Gly Ala Gly Ala Lys Cys Ser Arg Leu Met Tyr Asp Cys Cys
1               5                       10                      15

Thr Gly Ser Cys Arg Ser Gly Lys Cys
                20                  25
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-191, FIGURE 2

( x i ) SEQUENCE DESCRIPTION: SEQ ID NO:10:

```
Cys Ala Gly Ala Gly Ala Lys Cys Ser Arg Leu Met Tyr Asp Cys Cys
1               5                       10                      15

Thr Gly Ser Cys Arg Ser Gly Lys Cys
                20                  25
```

( 2 ) INFORMATION FOR SEQ ID NO:11:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-193, FIGURE 2

( x i ) SEQUENCE DESCRIPTION: SEQ ID NO:11:

```
Cys Lys Gly Ala Gly Ala Lys Cys Ser Arg Leu Met Tyr Asp Cys Cys
1               5                       10                      15

Thr Gly Ser Cys Arg Ser Gly Lys Cys Gly
                20                  25
```

( 2 ) INFORMATION FOR SEQ ID NO:12:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-194, FIGURE 2

( i x ) FEATURE:
        ( A ) NAME/KEY: Modified-site
        ( B ) LOCATION: 12
        ( D ) OTHER INFORMATION: /note= "where X is Nle"

( x i ) SEQUENCE DESCRIPTION: SEQ ID NO:12:

```
Cys Lys Gly Ala Gly Ala Lys Cys Ser Arg Leu Xaa Tyr Asp Cys Cys
1               5                       10                      15

Thr Gly Ser Cys Arg Ser Gly Lys Cys
                20                  25
```

( 2 ) INFORMATION FOR SEQ ID NO:13:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-195, FIGURE 2

( x i ) SEQUENCE DESCRIPTION: SEQ ID NO:13:

```
Cys Lys Gly Ala Gly Ala Lys Cys Ser Arg Leu Xaa Tyr Asp Cys Cys
1               5                   10                  15
Thr Gly Ser Cys Arg Ser Gly Ala Cys
            20              25
```

( 2 ) INFORMATION FOR SEQ ID NO:14:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-196, FIGURE 2

( x i ) SEQUENCE DESCRIPTION: SEQ ID NO:14:

```
Asn Cys Lys Gly Ala Gly Ala Lys Cys Ser Arg Leu Xaa Tyr Asp Cys
1               5                   10                  15
Cys Thr Gly Ser Cys Arg Ser Gly Ala Cys Gly
                20                  25
```

( 2 ) INFORMATION FOR SEQ ID NO:15:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-197, FIGURE 2

( x i ) SEQUENCE DESCRIPTION: SEQ ID NO:15:

```
Asn Ser Cys Lys Gly Ala Gly Ala Lys Cys Ser Arg Leu Xaa Tyr Asp
1                   5                   10                  15
Cys Cys Thr Gly Ser Cys Arg Ser Gly Ala Cys
                20                  25
```

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-198, FIGURE 2

( x i ) SEQUENCE DESCRIPTION: SEQ ID NO:16:

Cys Lys Gly Lys Gly Ala Lys Cys Ser Arg Leu Met Tyr Asp Cys Cys
1               5                   10                  15

Thr Gly Ser Cys Ala Ser Gly Lys Cys
            20              25

( 2 ) INFORMATION FOR SEQ ID NO:17:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-200, FIGURE 2

( x i ) SEQUENCE DESCRIPTION: SEQ ID NO:17:

Cys Lys Gly Ala Gly Ala Ala Cys Ser Arg Leu Met Tyr Asp Cys Cys
1               5                   10                  15

Thr Gly Ser Cys Arg Ser Gly Lys Cys
            20              25

( 2 ) INFORMATION FOR SEQ ID NO:18:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-201, FIGURE 2

( x i ) SEQUENCE DESCRIPTION: SEQ ID NO:18:

Cys Lys Gly Lys Gly Ala Lys Cys Arg Lys Thr Ser Tyr Asp Cys Cys
1               5                   10                  15

Thr Gly Ser Cys Arg Ser Gly Lys Cys
            20              25

( 2 ) INFORMATION FOR SEQ ID NO:19:

( i ) SEQUENCE CHARACTERISTICS:
      ( A ) LENGTH: 26 amino acids
      ( B ) TYPE: amino acid
      ( D ) TOPOLOGY: linear ( i i ) MOLECULE TYPE: protein ( i i i ) HYPOTHETICAL: NO ( v i ) ORIGINAL SOURCE:
      ( C ) INDIVIDUAL ISOLATE: SNX-202, FIGURE 2

( x i ) SEQUENCE DESCRIPTION: SEQ ID NO:19:

Cys Lys Leu Lys Gly Gln Ser Cys Ser Arg Leu Met Tyr Asp Cys Cys
1               5                   10                  15

Ser Gly Ser Cys Gly Arg Ser Gly Lys Cys 2 0                           2 5

(2) INFORMATION FOR SEQ ID NO:20:

(i) SEQUENCE CHARACTERISTICS:
        (A) LENGTH: 27 amino acids
        (B) TYPE: amino acid
        (D) TOPOLOGY: linear (i i) MOLECULE TYPE: protein (i i i) HYPOTHETICAL: NO (v i) ORIGINAL SOURCE:
        (C) INDIVIDUAL ISOLATE: SNX-207, FIGURE 2

(i x) FEATURE:
        (A) NAME/KEY: Modified-site
        (B) LOCATION: 4
        (D) OTHER INFORMATION: /note= "where X is hydroxyproline"

(i x) FEATURE:
        (A) NAME/KEY: Modified-site
        (B) LOCATION: 21
        (D) OTHER INFORMATION: /note= "where X is hydroxyproline"

(x i) SEQUENCE DESCRIPTION: SEQ ID NO:20:

Cys Leu Ser Xaa Gly Ser Ser Cys Ser Arg Leu Met Tyr Asn Cys Cys
1               5                   10                  15

Arg Ser Cys Asn Xaa Tyr Ser Arg Lys Cys Arg
                20              25

(2) INFORMATION FOR SEQ ID NO:21:

(i) SEQUENCE CHARACTERISTICS:
        (A) LENGTH: 26 amino acids
        (B) TYPE: amino acid
        (D) TOPOLOGY: linear (i i) MOLECULE TYPE: protein (i i i) HYPOTHETICAL: NO (v i) ORIGINAL SOURCE:
        (C) INDIVIDUAL ISOLATE: SNX-231, FIGURE 2

(i x) FEATURE:
        (A) NAME/KEY: Modified-site
        (B) LOCATION: 7
        (D) OTHER INFORMATION: /note= "where X is hydroxyproline"

(x i) SEQUENCE DESCRIPTION: SEQ ID NO:21:

Cys Lys Gly Lys Gly Ala Xaa Cys Arg Lys Thr Met Tyr Asp Cys Cys
1               5                   10                  15

Ser Gly Ser Cys Gly Arg Arg Gly Lys Cys
                20              25

(2) INFORMATION FOR SEQ ID NO:22:

(i) SEQUENCE CHARACTERISTICS:
        (A) LENGTH: 6 amino acids
        (B) TYPE: amino acid
        (D) TOPOLOGY: linear (i i) MOLECULE TYPE: protein (i i i) HYPOTHETICAL: NO (v i) ORIGINAL SOURCE:
        (C) INDIVIDUAL ISOLATE: CONOPEPTIDE GROUP 1 FRAGMENT, PAGE
        32

(x i) SEQUENCE DESCRIPTION: SEQ ID NO:22:

```
            Cys  Lys  Gly  Lys  Gly  Ala
            1                  5
```

( 2 ) INFORMATION FOR SEQ ID NO:23:

( i ) SEQUENCE CHARACTERISTICS:
        ( A ) LENGTH: 1 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT, PAGE
            32

( x i ) SEQUENCE DESCRIPTION: SEQ ID NO:23:

```
            Cys

1
```

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT, PAGE
            32

( x i ) SEQUENCE DESCRIPTION: SEQ ID NO:24:

```
            Tyr  Asp  Cys  Cys  Thr  Gly  Ser  Cys
            1                  5
```

( 2 ) INFORMATION FOR SEQ ID NO:25:

( i ) SEQUENCE CHARACTERISTICS:
        ( A ) LENGTH: 1 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 1 FRAGMENT, PAGE
            32

( x i ) SEQUENCE DESCRIPTION: SEQ ID NO:25:

```
            Arg

1
```

( 2 ) INFORMATION FOR SEQ ID NO:26:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( i i i ) HYPOTHETICAL: NO (v i) ORIGINAL SOURCE:
  (C) INDIVIDUAL ISOLATE: CONOPEPTIDE GROUP 1 FRAGMENT, PAGE 32

(x i) SEQUENCE DESCRIPTION: SEQ ID NO:26:

Gly Lys Cys
1

(2) INFORMATION FOR SEQ ID NO:27:

(i) SEQUENCE CHARACTERISTICS:
    (A) LENGTH: 9 amino acids
    (B) TYPE: amino acid
    (D) TOPOLOGY: linear (i i) MOLECULE TYPE: protein (i i i) HYPOTHETICAL: NO (v i) ORIGINAL SOURCE:
    (C) INDIVIDUAL ISOLATE: CONOPEPTIDE GROUP 2 FRAGMENT, PAGE 32

(i x) FEATURE:
    (A) NAME/KEY: Modified-site
    (B) LOCATION: 4
    (D) OTHER INFORMATION: /note= "where X is hydroxyproline"

(x i) SEQUENCE DESCRIPTION: SEQ ID NO:27:

Cys Leu Ser Xaa Gly Ser Ser Cys Ser
1               5

(2) INFORMATION FOR SEQ ID NO:28:

(i) SEQUENCE CHARACTERISTICS:
    (A) LENGTH: 8 amino acids
    (B) TYPE: amino acid
    (D) TOPOLOGY: linear (i i) MOLECULE TYPE: protein (i i i) HYPOTHETICAL: NO (v i) ORIGINAL SOURCE:
    (C) INDIVIDUAL ISOLATE: CONOPEPTIDE GROUP 2 FRAGMENT, PAGE 32

(x i) SEQUENCE DESCRIPTION: SEQ ID NO:28:

Tyr Asn Cys Cys Arg Ser Cys Asn
1               5

(2) INFORMATION FOR SEQ ID NO:29:

(i) SEQUENCE CHARACTERISTICS:
    (A) LENGTH: 26 amino acids
    (B) TYPE: amino acid
    (D) TOPOLOGY: linear (i i) MOLECULE TYPE: protein (i i i) HYPOTHETICAL: NO (v i) ORIGINAL SOURCE:
    (C) INDIVIDUAL ISOLATE: SNX-230, FIGURE 1

(x i) SEQUENCE DESCRIPTION: SEQ ID NO:29:

Cys Lys Gly Lys Gly Ala Pro Cys Arg Lys Thr Met Tyr Asp Cys Cys
1               5                   10                  15
Ser Gly Ser Cys Gly Arg Arg Gly Lys Cys
                20                  25

( 2 ) INFORMATION FOR SEQ ID NO:30:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-236, FIGURE 2

( x i ) SEQUENCE DESCRIPTION: SEQ ID NO:30:

```
Cys Leu Ser Xaa Gly Ser Ser Cys Ser Arg Leu Met Tyr Asn Cys Cys
1                5                   10                  15
Arg Ser Cys Asn Pro Tyr Ser Arg Lys Cys Arg
                20                  25
```

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: CONOPEPTIDE GROUP 2 FRAGMENT, PAGE 32

( x i ) SEQUENCE DESCRIPTION: SEQ ID NO:31:

```
Tyr Ser Arg Lys Cys Arg
1                5
```

( 2 ) INFORMATION FOR SEQ ID NO:32:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( C ) INDIVIDUAL ISOLATE: SNX-239, FIGURE 2

( x i ) SEQUENCE DESCRIPTION: SEQ ID NO:32:

```
Cys Lys Gly Lys Gly Ala Lys Cys Ser Leu Leu Met Tyr Asp Cys Cys
1                5                   10                  15
Thr Gly Ser Cys Arg Ser Gly Lys Cys
                20                  25
```

( 2 ) INFORMATION FOR SEQ ID NO:33:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:

-continued (C) INDIVIDUAL ISOLATE: SNX-199, FIGURE 2

(x i) SEQUENCE DESCRIPTION: SEQ ID NO:33:

```
Cys Lys Gly Lys Gly Ala Lys Cys Ser Ala Leu Met Tyr Asp Cys Cys
1               5                   10                  15
Thr Gly Ser Cys Arg Ser Gly Lys Cys
            20                  25
```

(2) INFORMATION FOR SEQ ID NO:34:

(i) SEQUENCE CHARACTERISTICS:
    (A) LENGTH: 25 amino acids
    (B) TYPE: amino acid
    (D) TOPOLOGY: linear (i i) MOLECULE TYPE: protein (i i i) HYPOTHETICAL: NO (v i) ORIGINAL SOURCE:
    (C) INDIVIDUAL ISOLATE: SNX 240, FIGURE 2

(i x) FEATURE:
    (A) NAME/KEY: Modified-site
    (B) LOCATION: 1
    (D) OTHER INFORMATION: /note= "THE CYSTEINE RESIDUE CARRIES AN ACETYL GROUP"

(x i) SEQUENCE DESCRIPTION: SEQ ID NO:34:

```
Cys Lys Gly Lys Gly Ala Lys Cys Ser Leu Leu Met Tyr Asp Cys Cys
1               5                   10                  15
Thr Gly Ser Cys Arg Ser Gly Lys Cys
            20                  25
```

METHOD OF TREATING INFLAMMATION

This is a continuation of application Ser. No. 08/675,354, filed Jul. 3, 1996 now pending, which is a continuation of allowed application Ser. No. 08/049,794, filed Apr. 15, 1993 now U.S. Pat. No. 5,587,454, which is a continuation-in-part of application Ser. No. 07/814,759, filed Dec. 30, 1991, now abandoned.

1. FIELD OF THE INVENTION

The present invention relates to compositions and methods of producing analgesia particularly in the treatment of pain and neuropathic pain.

2. REFERENCES

Ahmad, S. N. and Miljanich, G. P. (1988) Brain Research 453:247–256.

Basilico, L., Parenti, M., Frevola, L., and Giagnon, G. (1989). *Pharmacol. Res.* 21:65–66.

Bennett, G. J. and Xie, Y.-K. (1988) *Pain* 33:87–107.

Bennett, J. P. et al. (1983) *Neurotransmitter Receptor Binding* pp. 61–89; Raven Press, New York.

Ben-Sreti, M. M., Gonzalez, J. P. and Sewell, R. D. E. (1983) *Eur. J. Pharmacol.* 90:385–391.

Contreras, E., Tamayo, L., and Amigo, M. (1988) *Eur. J. Pharmacol.* 148:463–466.

Delgado-Escueta, A. V. et al., eds. (1986) *Adv. Neurol.* 44:1–120.

Dixon, W. J. (1976) *Ann. Rev. Pharmacol. Toxicol.* 20:441–462.

Fitzgerald, M. (1989) *TINS* 12(3):86–87.

Gray, W., Olivera, B., and Cruz, L. (1988) *Annual Review of Biochemistry* 57:665–700.

Hartley, D. and Choi, D. (1989), *The Journal of Pharmacology and Experimental Therapeutics* 250:752–758.

Jadad, A. R. et al. (1992) *Lancet* 339:1367–1371.

Kenakin, T. P. (1987) *Pharmacologic Analysis of Drug-Receptor Interaction*, Raven Press, NY.

Kim, S. H. and Chung, J. M. (1992) *Pain* 50:355–363.

Lehman, A. (1989) *J. Neurochem.* 53:525–535.

Lindorth, P. and Mopper, K. (1979) *Anal. Chem.* 51:1667–1674.

McCleskey, E. W. et al., *Proc. Natl. Acad. Sci. USA* 84:4327–31 (1987).

McGeer, P. L., Eccles, J. C. and McGeer, E. G. (1987) *Molecular Neurobiology of the Mammalian Brain*, Plenum Press, NY.

Newcomb, R. (1983) *J. Comp. Physiol.* 52: 331–341.

Nowycky, M. C., Fox, A. P., and Tsien, R. W., *Nature* (London), 316:440–443 (1985).

Olivera, B., McIntosh, M., Cruz, L., Luque, F., and Gray, W. (1984) *Biochemistry* 23:5087–5090.

Paxinos, G., and Watson, C. (1986). *The Rat Brain in Stereotaxic Coordinates*, 2nd Edition.

Ritchie, J. M. and Greene, N. M. (1990) in *Goodman and Gilman's The Pharmacological Basis of Therapeutics*, (Eighth Edition) Pergamon Press (New York) Chapter 15, pp. 311–331.

Sher, E. et al. (1991) *FASEB J.* 5:2677–2683.

Sher, E. and Clementi, F. (1991) *Neuroscience:* 42301–42307.

Takemura, M., et al. (1988). *Neuroscience Res.* 5:405–416.

Westerink, B. H. C. et al. *Life Sci.* 41:1763–1776.

Yaksh, T. L. and Noueihed, R. (1985) *Ann. Rev. Pharmacol. Toxicol.* 25:433–462.

Yaksh, T. L., and Rudy, T. A. (1976) *Physiol. Behav.* 17:1031–1036.

Yaksh, T. L., Yamamoto, 1 and Myers, R. R. (1992) in *Hyperalgesia and Allodynia* (Willis, W. D., editor), Raven Press, New York, Chapter 20, pp. 245–258.

Yamamoto, T. and Yaksh, T. L. (1991) *Life Sciences* 49:1955–1963.

Yamamoto, T. and Yaksh, T. L. (1992) *Neuroscience Lett.* 135:67–70.

Yamashiro, D. (1987) *Int. J. Peptide Protein Res.* 30:9–12.

3. BACKGROUND OF THE INVENTION

Chronic or intractable pain, such as may occur in conditions such as bone degenerative diseases and cancer, is a debilitating condition which is treated with a variety of analgesic agents, and often opioid compounds, such as morphine.

In general, brain pathways governing the perception of pain are still incompletely understood, sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region (McGeer). Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminal and which, when they fire, inhibit release of neurotransmitters, including substance P. Descending pathways from the brain are also inhibitory on C- and A-fiber firing.

Certain types of pain have complex etiologies. For example, neuropathic pain is generally a chronic condition attributable to injury or partial transection of a peripheral nerve. This type of pain is characterized by hyperesthesia, or enhanced sensitivity to external noxious stimuli. The hyperesthetic component of neuropathic pain does not respond to the same pharmaceutical interventions as does more generalized and acute forms of pain.

Opioid compounds (opiates) such as morphine, while effective in producing analgesia for many types of pain, are not always effective, and may induce tolerance in patients. When a subject is tolerant to opioid narcotics, increased doses are required to achieve a satisfactory analgesic effect. At high doses, these compounds produce side effects, such as respiratory depression, which can be life threatening. In addition, opioids frequently produce physical dependence in patients. Dependence appears to be related to the dose of opioid taken and the period of time over which it is taken by the subject. For this reason, alternate therapies for the management of chronic pain are widely sought after. In addition, compounds which serve as either a replacement for or as an adjunct to opioid treatment in order to decrease the dosage of analgesic compound required, have utility in the treatment of pain, particularly pain of the chronic, intractable type.

Although calcium blocking agents, including a number of L-type calcium channel antagonists, have been tested as adjunct therapy to morphine analgesia, positive results are attributed to direct effects on calcium availability, since calcium itself is known to attenuate the analgesic effects of certain opioid compounds (Ben-Sreti). EGTA, a calcium chelating agent, is effective in increasing the analgesic effects of opioids. However, results from tests of calcium antagonists as adjunct therapy to opioids have been contradictory; some L-type calcium channel antagonists have been shown to increase the effects of opioids, while others of these compounds have been shown to decrease opioid effects (Contreras).

U.S. Pat. No. 5,051,403 describes the use of omega-conopeptides having defined binding/inhibitory properties in the treatment of ischemia-related neuronal damage. Co-pending parent U.S. patent application Ser. No. 07/814,759 demonstrates the effectiveness of omega-conopeptide compositions in certain animal models of pain. Specifically, omega-conopeptides MVIIA and TVIA and derivatives thereof having related inhibitory and binding activities were demonstrated to produce analgesia in animal models of analgesia in which morphine is the standard positive control. The present invention is directed to the discovery that such omega conopeptides also exhibit analgesic properties in certain models of analgesia, such as neuropathic pain models of analgesia, in which morphine is not expected to produce positive results.

4. SUMMARY OF THE INVENTION

In one aspect, the invention includes a method of producing analgesia in a mammalian subject. The method includes administering to the subject, an omega conopeptide which is effective to (a) to inhibit electrically stimulated contraction of the guinea pig ileum, and (b) to bind selectively to omega conopeptide MVIIA binding sites present in neuronal tissue, where the activities in these assays are within the activities of omega conopeptides MVIIA (SNX-111) and TVIA (SNX-185). In another embodiment, the method includes administering an omega conopeptide which is further characterized by exhibiting a selectivity ratio of binding at said MVIIA binding site to binding at a site 2 omega conopeptide binding site which is within the range of selectivity ratios determined for omega conopeptides MVIIA/SNX-111, SNX-199, SNX-236, SNX-239 and TVIA/SNX-185. The omega-conopeptide is administered at a dose effective to produce analgesia in a standard animal model of nociceptive pain, as described herein.

In a preferred embodiment, the omega conopeptide is selected from the group consisting of SEQ ID NO: 7 (TVIA/SNX-185), SEQ ID NO: 1 (MVIIA/SNX-111), SEQ ID NO: 30 (SNX-236), SEQ ID NO: 2 (SNX-159), SEQ ID NO: 32 (SNX-239), SEQ ID NO: 33 (SNX-199) and derivatives thereof.

In yet another embodiment, the invention includes a method of producing analgesia in a mammalian subject experiencing neuropathic pain. This method includes administering to the subject, an omega conopeptide which is effective (a) to inhibit electrically stimulated contraction of the guinea pig ileum, and (b) to bind selectively and reversibly to omega conopeptide MVIIA binding sites present in neuronal tissue, where the activities in these assays are within the activities of omega conopeptides MVIIA (SNX-111) and TVIA (SNX-185). In a preferred embodiment, the omega conopeptide is selected from the group consisting of SEQ ID NO: 1 (MVIIA/SNX-111), SEQ ID NO: 32 (SNX-239), SEQ ID NO: 2 (SNX-159) and derivatives thereof.

In yet another aspect, the invention also includes novel conopeptides having the sequences: SEQ ID NO: 30 (SNX-236), SEQ ID NO: 32 (SNX-239), and SEQ ID NO: 33 (SNX-199).

These and other objects and features of the present invention will become more fully apparent when the following detailed description of the invention is read in conjunction with the accompanying drawings.

BRIEF DESCRIPTION OF THE DRAWINGS

FIGS. 1A and 1B shows primary sequences of several natural omega-conopeptides, MVIIA/SNX-111 (SEQ ID NO: 01), MVIIB/SNX-159 (SEQ ID NO: 02), GVIA/SNX-124 (SEQ ID NO: 03), GVIIA/SNX-178 (SEQ ID NO: 04), RVIA/SNX-182 (SEQ ID NO: 05), SVIA/SNX-157 (SEQ ID NO: 06), TVIA/SNX-185 (SEQ ID NO: 07), SVIB/SNX-183 (SEQ ID NO: 08), and MVIIC/SNX-230 (SEQ ID NO: 29), and SNX-231 (SEQ ID NO: 21);

FIGS. 2A and 2B shows several analog omega-conopeptides SNX-190 (SEQ ID NO: 09), SNX-191 (SEQ ID NO: 10), SNX-193 (SEQ ID NO: 11), SNX-194 (SEQ ID NO: 12), SNX-195 (SEQ ID NO: 13), SNX-196 (SEQ ID NO: 14), SNX-197 (SEQ ID NO: 15), SNX-198 (SEQ ID NO: 16), SNX-199 (SEQ ID NO: 33), SNX-200 (SEQ ID NO: 17), SNX-201 (SEQ ID NO: 18), SNX-239 (SEQ ID NO: 32), SNX-240 (SEQ ID NO: 34), SNX-202 (SEQ ID NO: 19), SNX-207 (SEQ ID NO: 20), SNX-236 (SEQ ID NO: 30), and their relationships to SNX-111 (SEQ ID NO: 01), SNX-185 (SEQ ID NO: 07) or SNX-183 (SEQ ID NO: 08);

FIG. 12 shows autoradiograms of the distributions of [$^{125}$I]-SNX-111 (A,B,C,D) and [$^{125}$I]-SNX-183 (E,F,G,H) binding to coronal rat brain rostral (A,C,E,G) and caudal (B,D,F,H) sections labeled in the absence of excess nonradioactive SNX-III (A,B) or SNX-183 (E,F) or in the presence of excess non-radioactive SNX-111 (C,D) or SNX-183 (G,H), in which "CA" indicates the $CA_3$ region of the hippocampus and "SN" indicates the substantia nigra;

FIG. 14 shows omega-conopeptide groupings: I, MVIIA, SNX-199 (SEQ ID NO: 33), MVIIB and SNX-239 (SEQ ID NO: 32), II, TVIA, SNX-207 and SNX-236, III, RVIA, SVIA, GVIIA, SVIB, MVIIC, SNX-231;

DETAILED DESCRIPTION OF THE INVENTION

I. Omega-conopeptides

Figure 3:
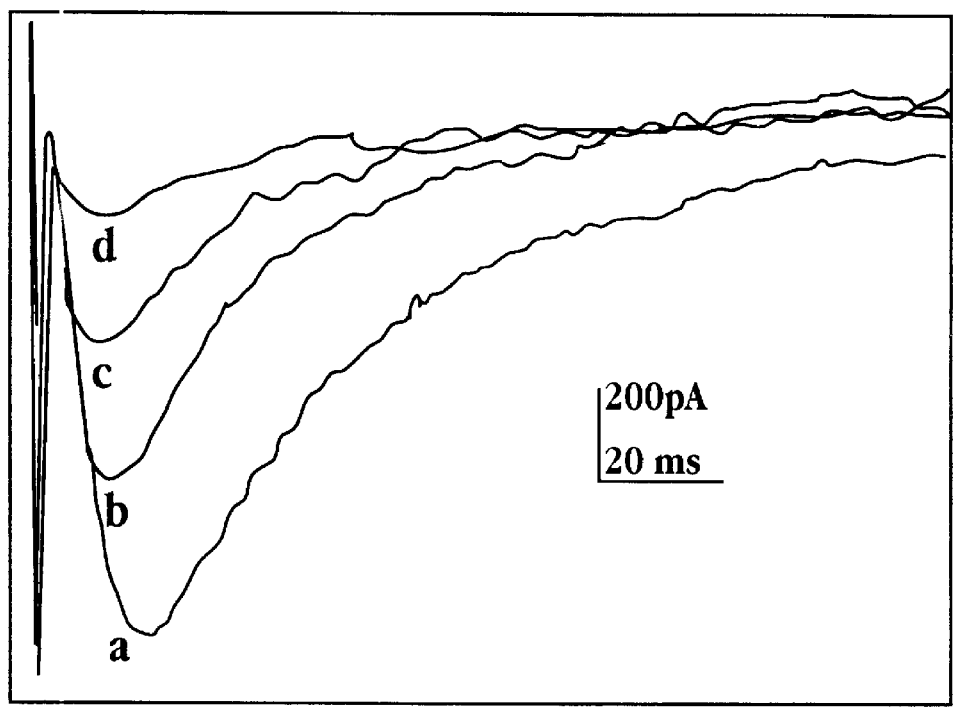
FIGS. 3A–3D show voltage-gated calcium current traces induced by a voltage step from $-100$ or $-80$ mV to $-20$ mV in untreated N1E-115 neuroblastoma cells (3A) and in neuroblastoma cells exposed to increasing concentrations of OCT MVIIA (SNX-111) (3B–3D)

Omega-conopeptides are components of peptide toxins produced by marine snails of the genus Conus, and which act as calcium channel blockers (Gray). About 500 species of cone snails in the Conus genus have been identified, and a variety of omega-conopeptides from several of these species have been isolated. The primary sequences of eight natural omega-conopeptides are shown in FIG. 1, where SNX-231 is an alternative form of MVIIC/SNX-230. Conventional letter initials are used for the amino acid residues, and X represents 4-hydroxyproline, also abbreviated 4Hyp. All of the peptides shown in the figure are amidated at their C-termini.

The peptides shown in FIG. 1 are identified by names which are commonly associated with either the naturally occurring peptide (single letter followed by a Roman numeral followed by a single letter), and by a synthetic designation (SNX-plus numeral). Either or both of these designations will be used interchangeably throughout the specification. For example, the peptide whose sequence is designated MVIIA/SNX-111 will be referred to herein as OCT MVIIA, or alternatively, SNX-111, the latter to signify that the compound is synthetic in origin. Synthetic and naturally occurring peptides having the same sequence behave substantially identically in the assays and methods of treatment of the invention.

The OCT MVIIA (SNX-111) and OCT GVIA (SNX-124) peptides also have the common names CmTx and CgTx, respectively.

All of the omega-conopeptides have three disulfide linkages connecting cysteine residues 1 and 4, 2 and 5, and 3 and 6, as indicated for the MVIIA peptide in FIG. 2. FIG. 2 shows analogs or derivatives of natural OCT MVIIA, OCT TVIA, and OCT SVIB peptides which have been synthesized and tested in accordance with the invention.

Standard single amino acid code letters are used in the figure; X=hydroxyproline; Nle=norleucine; $NH_2$ group at the C terminus indicates that the peptide is C-terminal amidated; G—OH indicates termination in an unmodified glycine residue.

A. Preparation of Omega-conopeptides

This section describes the synthesis, by solid phase methods, of several naturally occurring omega conotoxin (OCT) peptides and additional omega-conopeptides which are used in the present invention.

Omega-conopeptides, such as those shown in FIGS. 1 and 2, can be synthesized by conventional solid phase methods, such as have been described (Olivera). Briefly, N-alpha-protected amino acid anhydrides are prepared in crystallized form or prepared freshly in solution and used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1–2 reaction cycles are used for the first twelve residue additions, and 2–3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amide, after peptide cleavage from the resin. After removal of the hydrogen fluoride, the peptide is extracted into 1M acetic acid solution and lyophilized. The three disulfide linkages in the peptides may be formed by air oxidation in the presence of dithiothreitol (DTT) or optionally other thiol containing compounds (e.g., cysteine, glutathione), according to procedures detailed in Example 1.

The peptide can be isolated by an initial separation by gel filtration, to remove peptide dimers and higher molecular weight polymers, and also to remove undesired salts, such as guanidine hydrochloride, used in the oxidation reaction. The partially purified peptide is further purified by preparative HPLC chromatography, and the purity and identity of the peptide confirmed by amino acid composition analysis, mass spectrometry and by analytical HPLC in two different solvent systems.

B. In vitro Properties of Omega-conopeptides

1. Calcium-Channel Antagonist Activity

Voltage-gated calcium channels are present in neurons, and in cardiac, smooth, and skeletal muscle and other excitable cells, and are known to play a variety of roles in membrane excitability, muscle contraction, and cellular secretion, such as in synaptic transmission (McCleskey). In neuronal cells, voltage-gated calcium channels have been classified by their electrophysiological as well as by their biochemical (binding) properties.

Electrophysiologically, these channels can be classified either as Low-voltage-activated (LVA) or High-voltage-activated (HVA). HVA channels are currently known to comprise at least three groups of channels, known as L-, N- and P-type channels (Nowycky, Sher). These channels have been distinguished one from another electrophysiologically as well as biochemically on the basis of their pharmacology and ligand binding properties. Thus, dihydropyridines, diphenylalkylamines and piperidines bind to the alpha, subunit of the L-type calcium channel and block a proportion of HVA calcium currents in neuronal tissue, which are termed L-type calcium currents.

N- or omega-type HVA calcium channels are distinguishable from other calcium channels by their sensitivity to omega conotoxins (conopeptides). Such channels are insensitive to dihydropyridine compounds, such as L-type calcium channel blockers nimodipine and nifedipine. (Sher, Sher and Clementi).

Omega conotoxins bind to a specific population of binding sites, present mainly in neuronal tissue. Dihydropyridines and other L-type channel blockers do not displace omega conotoxin binding, nor do omega conotoxins displace binding of such L-channel specific ligands to L-type calcium channels. These observations indicate that L-type calcium channel blockers and N-type calcium channel blockers act at distinct channels. Unlike L-type calcium channels, N-type or omega channels are found predominantly, although not exclusively, in nervous tissue (Sher).

One suitable system for testing inhibition (blockage) of N-type or omega HVA neuronal calcium channels is an isolated cell system, such as the mouse neuroblastoma cell line, strain N1E115 or the human neuroblastoma cell line IMR32. Membrane currents are conveniently measured with the whole cell configuration of the patch clamp method, according to the procedure detailed in Example 2. Briefly, a voltage clamp protocol was performed in which the cell potential was stepped from the holding potential of about −100 mV to test potentials that ranged from −60 mV to +20 mV, and the cell was held at the holding potential for 5 seconds between pulses.

FIG. 3 shows a typical inward calcium current elicited by a voltage step from −80 mV to −20 mV in the absence of OCT. In this, and most of the recordings shown, barium (Ba) replaced calcium (Ca) as the charge-carrier through the calcium channels in order to increase the signal (McCleskey). According to the procedure described in Example 2, an N1E115 neuroblastoma cell was bathed in saline with sodium replaced by N-methyl-D-glucamine (NMDG), and 10 mM Ba instead of 2 mM Ca. These substitutions reduced the sodium current that would otherwise have contained the calcium current record, and increased the calcium current above what is would have been with only 2 mM Ca in the bath. Potassium currents were blocked by tetraethylammonium (TEA) in the bath and cesium (Cs) in the pipet solution.

As seen from FIG. 3, curve A, the calcium current activates quickly (within about 20 ms) and inactivates with a time constant of 30 to 40 ms. The calcium current is measured by the amplitude of the peak inward current elicited by the depolarization peak, and has a measured value of about −1200 pA. The cell in FIG. 3 (curve A) was also exposed to 1 $\mu$M nifedipine, a dihydropyridine, which is expected to effectively block L-type calcium channels in the neuroblastoma cells, and no effect on the measured calcium current was observed. The calcium current observed is thus not dihydropyridine-sensitive.

Figure 4:
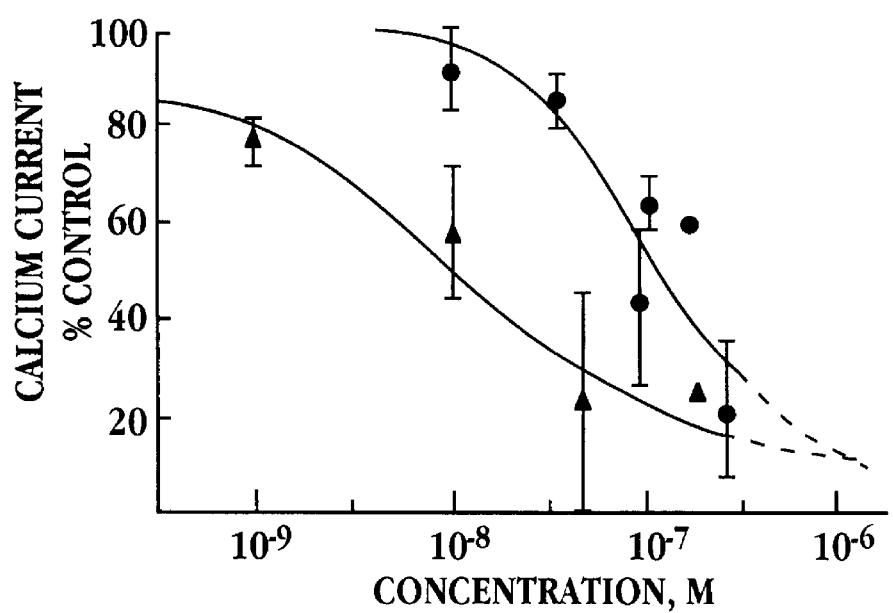
FIG. 4 plots the percent inhibition of peak inward calcium currents in neuroblastoma cells as a function of OCT MVIIA (SNX-111) (solid triangles) and OCT GVIA (SNX-124) (solid circles)

The responses of voltage-gated calcium currents to increasing concentrations of OCTs MVIIA (SNX-111) and GVIA (SNX-124) are shown in FIG. 4. The $IC_{50}$ concentration, at which 50% inhibition of calcium current is produced, is determined from the voltage-gated current amplitudes, plotted as a function of omega-conopeptide concentration. The calculated $IC_{50}$ is about 10 nM for GVIA and 100 nM for MVIIA, indicative of high inhibitory peptide activity. The $IC_{50}$ concentration for these and omega-conopeptides SVIA (SNX-157) and SVIB (SNX-183) are given in Table 1 below.

TABLE 1

| Inhibition of calcium currents in N1E-115 neuroblastoma cells | |
|---|---|
| Compound | $IC_{50}$ |
| GVIA (SNX-124) | 10 nM |
| MVIIA (SNX-111) | 100 nM |
| SVIB (SNX-183) | >1 $\mu$M |
| SVIA (SNX-157) | >20 $\mu$M |

Figure 5A:
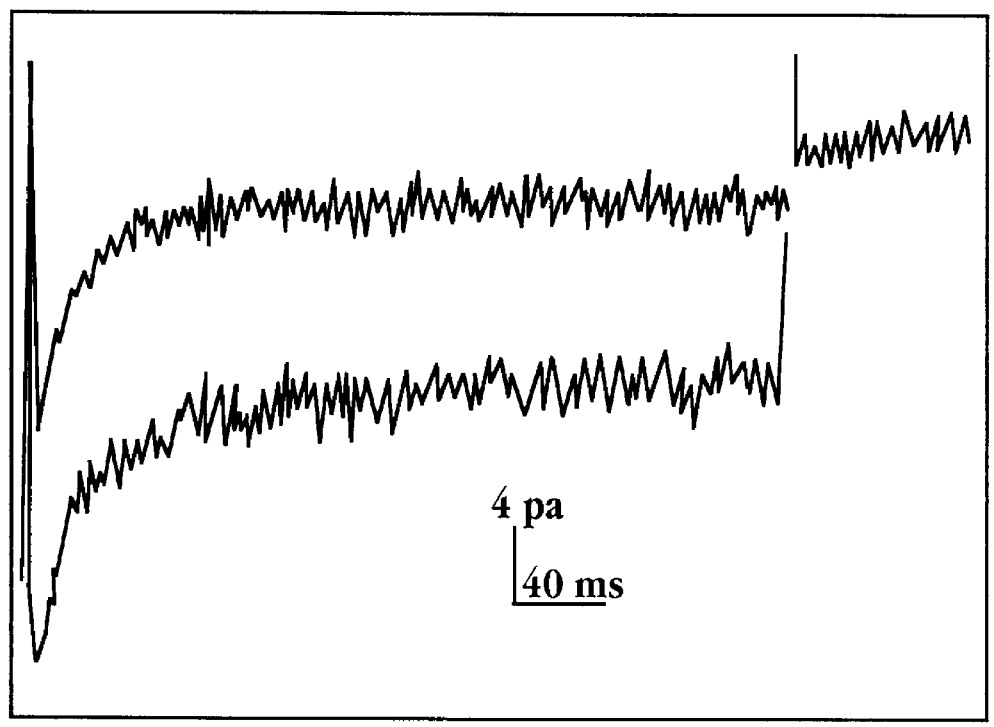
FIG. 5A shows voltage-gated calcium current traces induced by a voltage step from $-70$ to $-20$ mV in human neuroblastoma cells (IMR-32) in the absence (lower trace) and presence (upper tracing) of 150 nM SNX-111.

Calcium currents were also measured in human neuroblastoma IMR32 cells, using techniques described above and in Example 2. Voltage-gated calcium currents were elicited by holding the cell(s) at −70 mV and administering a step-voltage to −10 mV. Current tracings from IMR-32 cells bathed in control medium (lower curve) and in medium containing 150 nM SNX-111 (upper curve) are shown in FIG. 5A. The amplitude of the current is shown on the abscissa. The peak inward current is shown as the difference between the resting potential shown at the far left side of the figure and the lowest point of the curve, just adjacent to the resting value. In this experiment attenuation of voltage-gated calcium current is apparent in the presence of SNX-111 (upper curve), as shown by the decreased amplitude of the peak inward current.

Figure 5B:
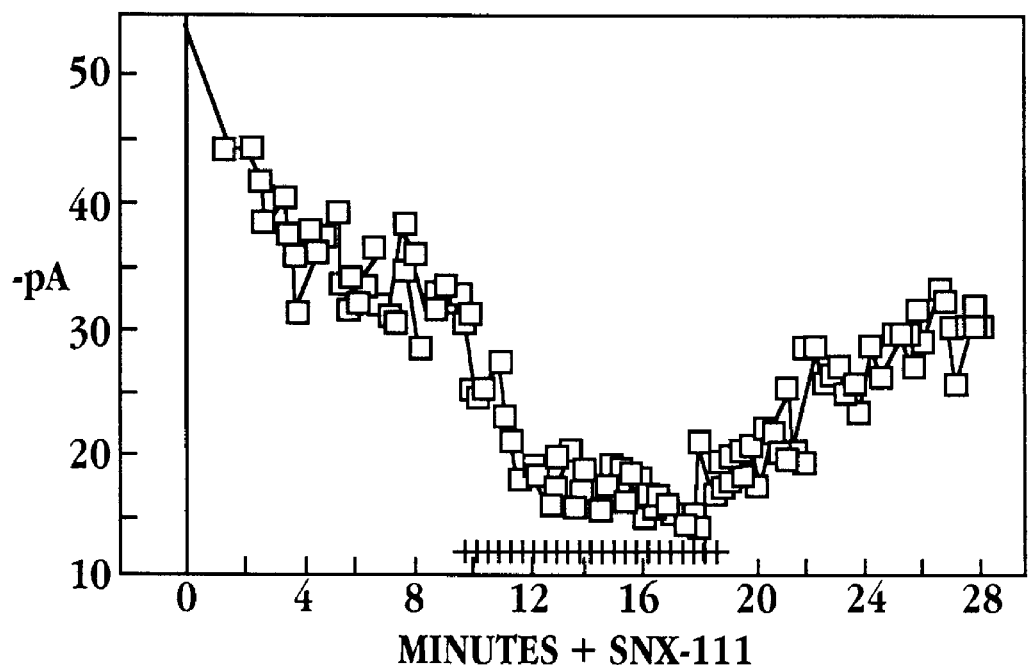
FIG. 5B shows a plot of absolute values of peak inward current measured every 15 seconds in IMR-32 cells, elicited by pulses from $-70$ to $0$ or $-10$ mV, versus time, where addition of SNX-111 to the bathing medium is indicated by hatch marks just above the ordinate.

FIG. 5B shows cumulative data from many consecutive currents, elicited at 15 second intervals as described above, in IMR-32 cells. In these plots, peak inward current recorded from each stimulus is recorded sequentially as a single data point. In the experiment illustrated in FIG. 5B, addition of SNX-111 to the bathing medium resulted in decreased peak inward currents; restoration of substantially normal calcium currents was achieved after washing of the compound from the cell chamber, shown on the right side of the figure.

Test peptides which are inhibitory for neuronal cell calcium currents can be further tested in non-neuronal cells, to confirm that the peptide activity in blocking calcium currents is specific to neuronal cells. A variety of muscle cell types which are refractory to calcium-current inhibition by OCTs, such as vertebrate embryo heart and skeletal muscle cells, are suitable. Cell current measurements are made substantially as outlined above and detailed in Example 2. OCT MVIIA, for example, has been reported to block voltage-gated calcium channels in a variety of neuronal cells, including dorsal root ganglion (DRG) neurons (McCleskey). This blockage or inhibition of calcium channel currents has been reported to be neuron-specific, since calcium current inhibition by the peptide was not observed in cardiac, smooth, and skeletal muscles.

2. Specific. High Affinity Binding to OCT Receptors.

Omega-conopeptides have been shown, in accordance with the invention, to bind with high affinity to specific binding site(s) in neuronal cells. In accordance with the selectivity of the compound, the binding affinity can be characterized either by the binding constant of the compound for the MVIIA (SNX-111) binding site, also referred to as "site 1" herein, or the binding constant of the compound for the SVIB (SNX-183) or the MVIIC (SNX-230) binding site, also referred to as "site 2" herein. Evidence for the existence of at least two distinct OCT binding sites is summarized below. In some cases, when specific binding to one site is preferred, it will be useful to characterize omega-conopeptides according to the ratio of their binding constants measured for binding to neuronal-cell MVIIA (SNX-111) binding site 1 and SVIB (SNX-183) or MVIIC (SNX-230) binding site 2.

Binding to the OCT MVIIA binding site in neuronal tissue can be demonstrated in a variety of cell types and synaptosomal cell fractions. One preferred synaptosomal fraction is a mammalian brain synaptosomal membrane preparation, such as the rat brain synaptosome preparation described in Example 3. The binding constant of a compound for the MVIIA binding site is typically determined by competitive displacement of radiolabeled OCT MVIIA (SNX-111) from the synaptosomal preparation, as follows.

Figure 6A:
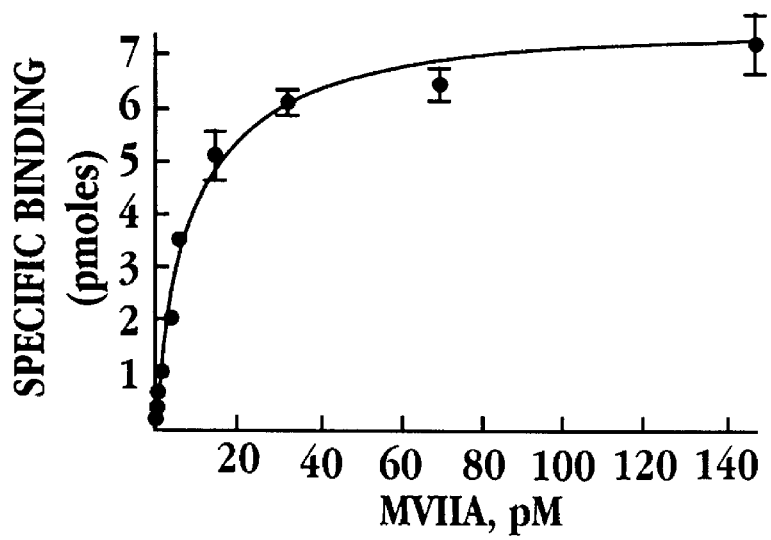
FIGS. 6A and 6B are a binding curve showing the amount of radioiodinated OCT MVIIA (SNX-111) bound to rat synaptosomal membranes, as a function of OCT MVIIA (SNX-111) concentration (6A), and the same data plotted as a Scatchard plot (6B)
Figure 6B:
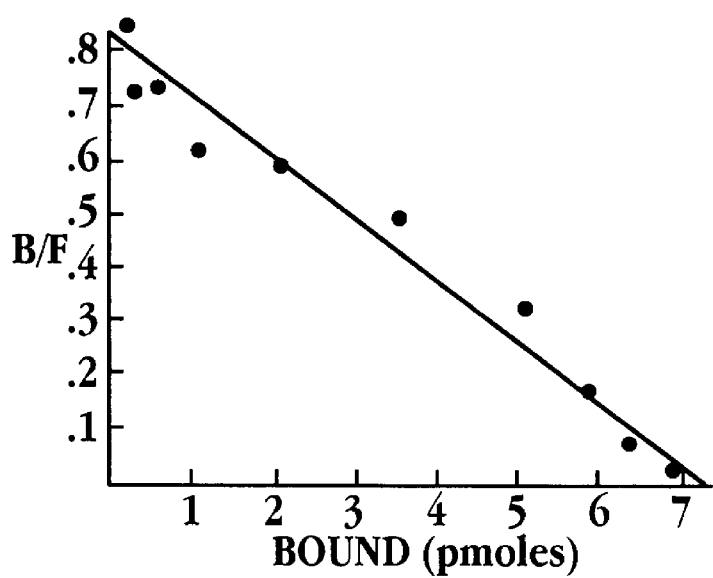

The binding constant $K_d$ of the MVIIA (SNX-111) peptide for the synaptosomal membranes is determined by a saturation binding method in which increasing quantities of radiolabeled peptide are added to the synaptosomal membranes, and the amount of labeled material bound at each concentration is determined (Example 3A). The appropriate binding equation describing the concentration of bound ligand as a function of the total ligand in equilibrium is fitted to the data to calculate the $B_{max}$ (the concentration of binding sites on the synaptosomes), and the $K_d$ (which is approximately the concentration of the ligand required for half saturation of binding sites). FIG. 6A shows the specific binding of radiolabeled OCT MVIIA (SNX-111) to rat brain synaptosomal membranes, plotted as a function of omega-conopeptide concentration, and FIG. 6B shows the same data in Scatchard plot form. From the slope of the Scatchard plot line, a $K_d$ binding value of 10 pM is obtained. Similarly $K_d$'s were determined for binding of radiolabelled SVIB (SNX-183) and MVIIC (SNX-230) to binding sites in synaptosomal membranes.

Reversibility of binding is a characteristic of ligands which, under equilibrium conditions, freely associate with and dissociate from their respective binding sites. Reversibility of binding of a specific compound is demonstrated by the labelled compound's ability to be displaced by unlabelled compound, after equilibrium binding of the labelled compound has been achieved. For example, dissociability of binding of a labelled compound can be determined as detailed in Example 3B, where a synaptosomal preparation was incubated with labelled compound for a time period sufficient to produce a stable level of binding, then excess unlabelled compound was added to the preparation. The preparation was then assayed for bound labelled compounds at various timepoints after addition of unlabelled compound.

Figure 7:
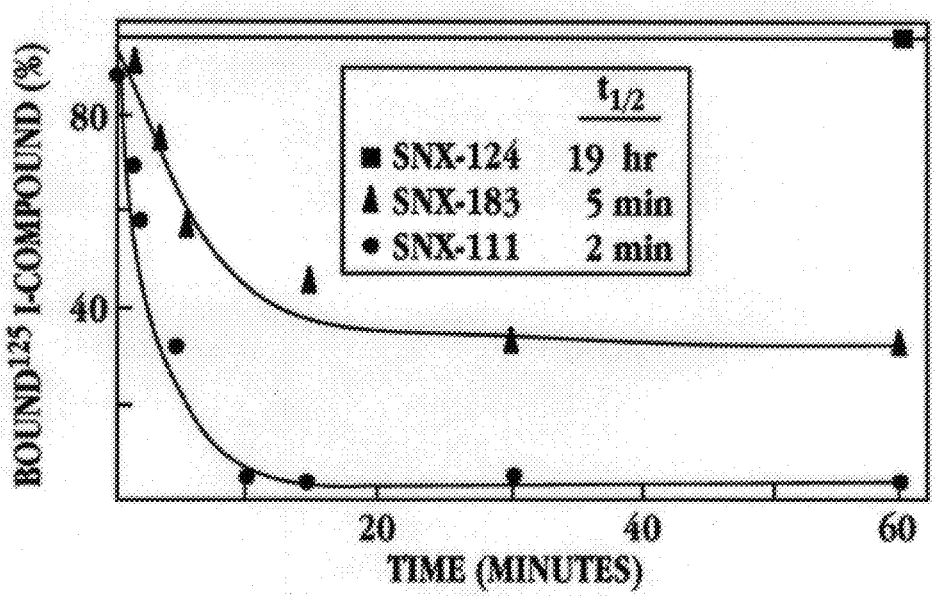
FIG. 7 shows reversibility of equilibrium binding of radioiodinated SNX-111 and SNX-183, and irreversibility of binding of radioiodinated SNX-124 to rat brain synaptosomal membranes.

If the labelled compound binds reversibly to the preparation, a reduction of labelled binding, to essentially non-specific binding levels, should be observed over time. FIG. 7 shows a plot of the dissociation kinetics of labelled SNX-111, SNX-183 and SNX-124. In contrast to SNX-111 binding, labelled OCT GVIA (SNX-124) does not dissociate from synaptosomal membranes over the course of an hour and has a calculated $t_{1/2}$ of 19 hours. SNX-124 binding can therefore be said to be essentially irreversible, while SNX-111 and SNX-183 bind reversibly to their respective binding sites.

Figure 8A:
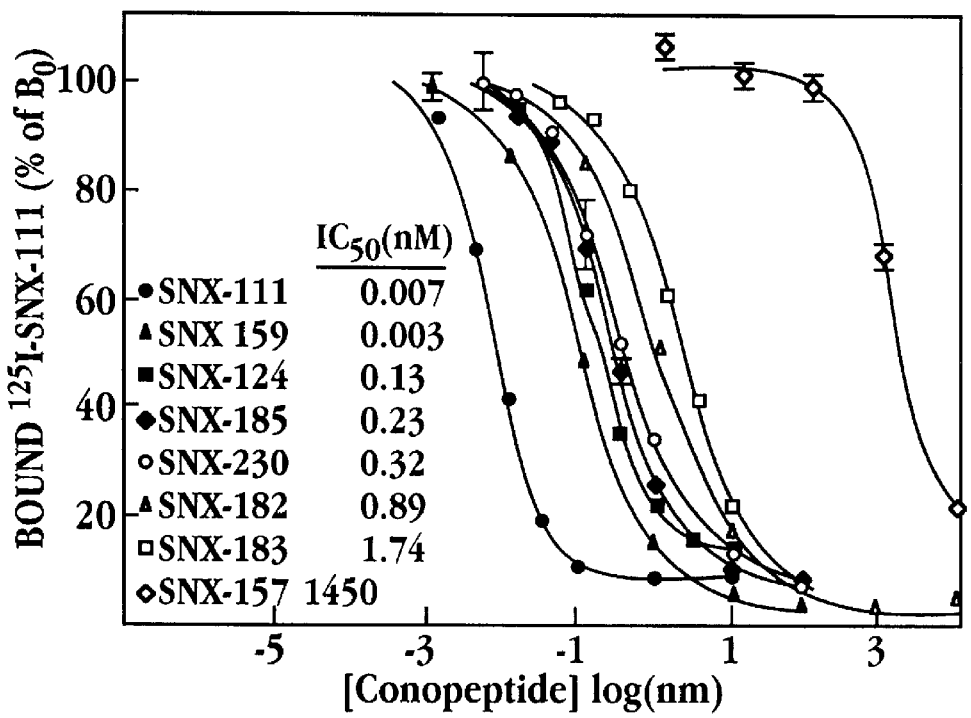
FIGS. 8A and 8B show computer-fit competitive binding curves for omega-conopeptide binding to the OCT MVIIA (SNX-111) binding site in rat brain synaptosomes.
Figure 8B:
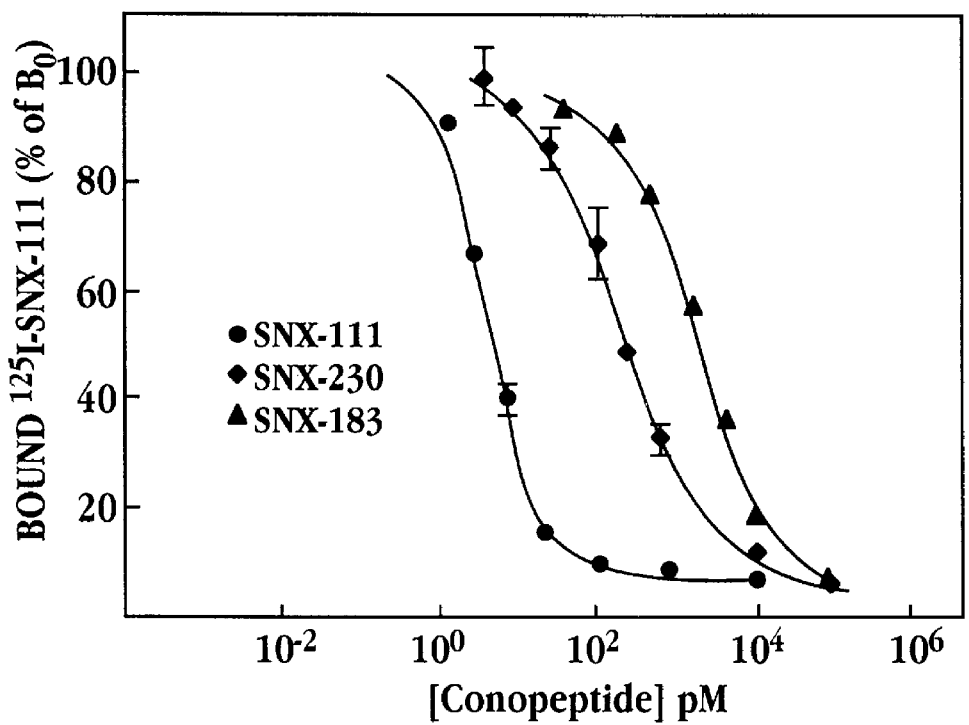

To determine the binding constant of a test compound for an OCT binding site, the test compound is added, at increasing concentrations, to the synaptosome preparation in the presence of a standard concentration of a radiolabeled OCT which exhibits reversible binding, such as OCT MVIIA (SNX-111). The synaptosomal material is then rapidly filtered, washed and assayed for bound radiolabel. The binding constant ($K_i$) of the test compound is determined from computer-fit competitive binding curves, such as shown in FIGS. 8A and 8B for MVIIA (SNX-111) peptide, to determine first the $IC_{50}$ value of the compound, i.e., the concentration which gives 50% displacement of labeled MVIIA peptide. A $K_i$ is determined according to standard methods from the $K_d$ value of OCT MVIIA and the $IC_{50}$ value of the compound, as detailed in Example 3. A relative potency value can also be calculated from this information (Example 3). Like the $K_i$ value, this value allows comparisons between assays performed under slightly differing conditions or at different times. Calculated $IC_{50}$ values for a number of omega-conopeptides for binding of OCT MVIIA (SNX-111) are given in Table 2. The compounds are arranged in order of increasing $IC_{50}$ values.

TABLE 2

Competition of $^{125}$I-MVIIA (SNX-111) Binding by OTC Peptides

| | $IC_{50}$ (nM) |
|---|---|
| SNX-207 | .007 |
| SNX-194 | .008 |
| SNX-195 | .009 |
| MVIIA (SNX-111) | .010 |
| SNX-190 | .021 |
| SNX-236 | .030 |
| SNX-200 | .039 |
| SNX-201 | .046 |
| SNX-202 | .046 |
| SNX-193 | .070 |
| SNX-194 | .090 |
| SNX-239 | .090 |
| MVIIC (SNX-230) | .32 |
| MVIIB (SNX-159) | .101 |

TABLE 2-continued

Competition of $^{125}$I-MVIIA (SNX-111) Binding by OTC Peptides

|  | IC$_{50}$ (nM) |
|---|---|
| GVIA (SNX-124) | .134 |
| SNX-198 | .160 |
| SNX-191 | .165 |
| TVIA (SNX-185) | .228 |
| SNX-196 | .426 |
| RVIA (SNX-182) | .893 |
| SVIB (SNX-183) | 1.5 |
| GVIIA (SNX-178) | 3.70 |
| SNX-197 | 11.3 |
| SVIA (SNX-157) | 1460. |

Figure 9A:
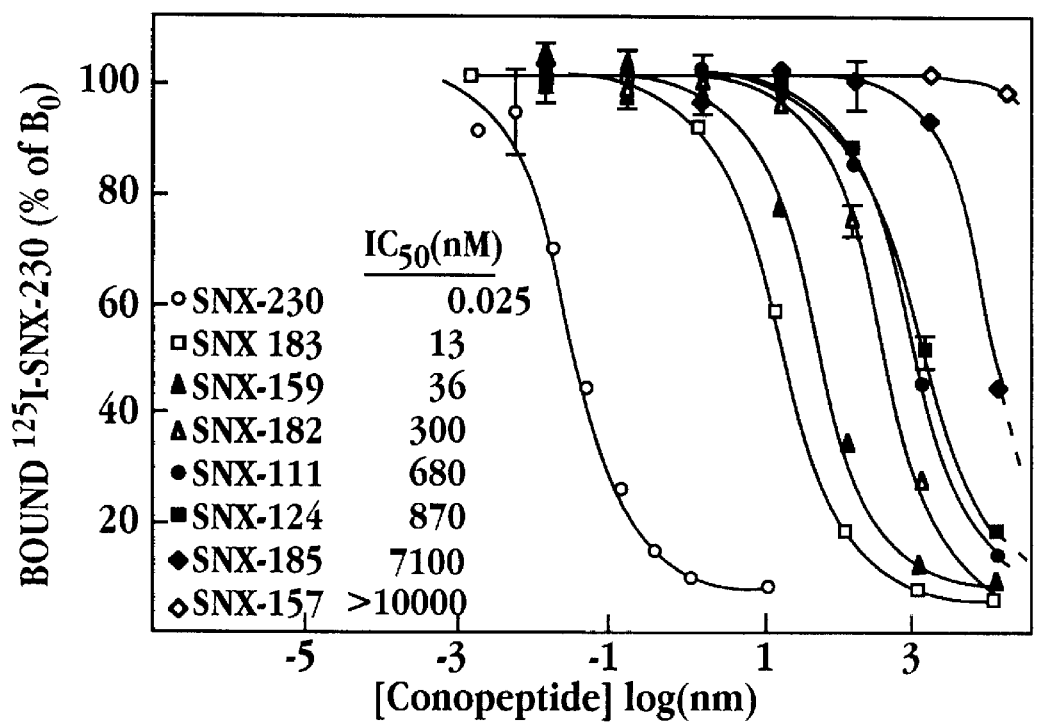
FIGS. 9A and 9B show computer-fit competitive binding curves for omega-conopeptide binding to the OCT MVIIC (SNX-230) binding site in rat brain synaptosomes.
Figure 9B:
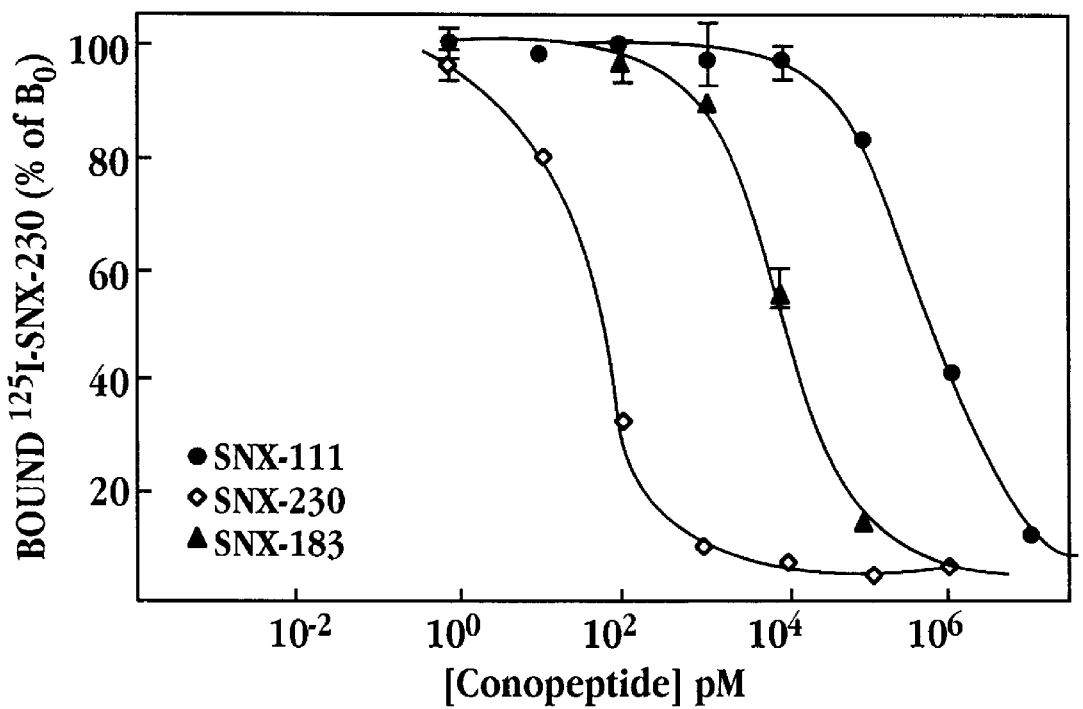

Similarly, IC$_{50}$ and K$_i$ values for compound binding to the SVIB (SNX-183) binding site can be calculated, as above, by determining the K$_d$ of labeled OCT SVIB (SNX-183) or OCT MVIIC (SNX-230) binding to a synaptosome preparation, then using competitive displacement of the labeled compound by the test compound, to determine the IC$_{50}$ and K$_i$ or relative potency values of the test compound. FIGS. 9A and 9B show computer-fit competitive binding curves for several omega-conopeptides whose binding to the SVIB (SNX-183) and/or MVIIC (SNX-230) binding sites was examined. From these curves, IC$_{50}$ values were determined as above.

Tables 3A and 3B list the relative potencies for binding of various omega-conopeptides to the site 1 and site 2 binding sites, and show the ratio of Ki or ID$_{50}$ values determined for binding of each compound to the sites.

TABLE 3A

Selectivity of Conopeptides for Site 1 and Site 2

| Compound | Ki (nM) for competition$^a$ with: | | Selectivity$^b$ for: | |
|---|---|---|---|---|
|  | [$^{125}$I]-SNX-111 | [$^{125}$I]-SNX-230 | site 1 | site 2 |
| SNX-111 | 0.002 | 150 | 75,000:1 |  |
| SNX-183 | 0.43 | 6 | 14:1 |  |
| SNX-230 | 0.20 | 0.03 |  | 1:7 |

$^a$Ki values were derived from analysis of competitive binding performed as described in FIG. 1.
$^b$Selectivity is expressed as the ratio of the Ki v 1alue determined for competition with [$^{125}$I]-SNX-230 binding divided by the Ki value for competition with [$^{125}$I]-SNX-111 binding.

TABLE 3B

Selectivity of Conopeptides for Site 1 and Site 2

| Compound | IC$_{50}$ (nM) for competition with: | | Selectivity$^a$ for: | |
|---|---|---|---|---|
|  | [$^{125}$I]-SNX-111 | [$^{125}$I]-SNX-230 | site 1 | site 2 |
| SNX-199 | 0.09 | 5,000 | 56,000:1 |  |
| SNX-236 | 0.03 | 1,500 | 50,000:1 |  |
| SNX-239 | 0.09 | 10,000 | 111,000:1 |  |

$^a$Selectivity is expressed as the ratio of the IC$_{50}$ value determined for competition with [$^{125}$I]-SNX-230 binding divided by the IC$_{50}$ value for competition with [$^{125}$I]-SNX-111 binding.

The identity of the MVIIA and SVIB binding sites in neuronal-cell membranes was examined by binding radio-labeled OCT MVIIA to synaptosomes, and crosslinking the peptide to the neuronal membranes, as detailed in Example 4. The labeled membranes were solubilized with sodium dodecyl sulfate (SDS), fractionated by polyacrylamide gel electrophoresis (PAGE), and examined by autoradiography for labeled polypeptide bands. In one case, the membranes were incubated with labeled peptide in the presence of excess unlabeled OCT MVIIA. A similar binding study was carried out with labeled OCT SVIB.

Figures 10A, 10B:
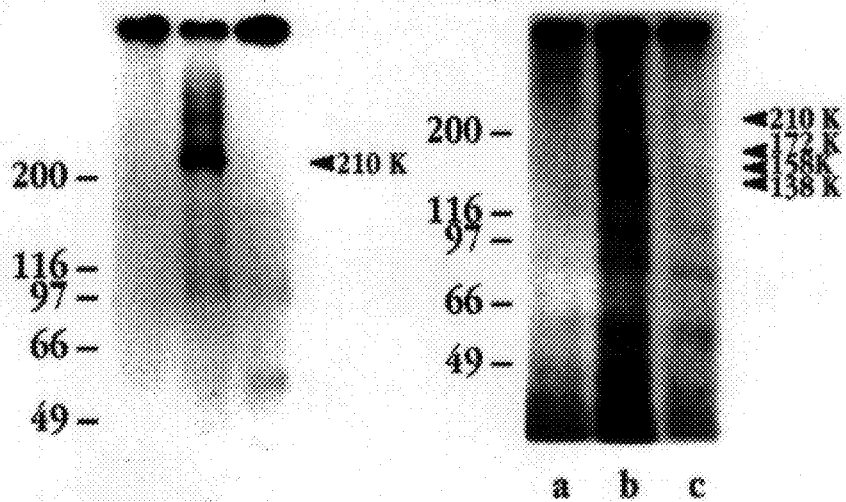
FIGS. 10(A and B) shows SDS-PAGE autoradiograms of rat synaptosomal membranes having covalently bound radioiodinated OCT MVIIA (SNX-111) (A) or covalently bound radioiodinated OCT SVIB (SNX-183) (B) added to the membranes in the presence (lanes c and f) or absence (lanes a,b and d,e) of non-radiolabeled OCT, where lanes a and d are control preparations in which no cross-linking agent was added.

Further evidence that the two receptor sites identified by SNX-111 and SNX-183 are distinct was obtained from affinity crosslinking studies in which [$^{125}$I]-SNX-111 and [$^{125}$I]-SNX-183 were chemically crosslinked to rat brain synaptosomal membrane preparations and then subjected to SDS-PAGE followed by autoradiography (FIG. 10). [$^{125}$I]-SNX-111 specifically labelled a protein of M$_r$ 210–220 kDa, as indicated in the autoradiograph. Unlabelled SNX-111 inhibited labeling of this protein with radioactive SNX-111 with an IC$_{50}$ of 30 pM, in good agreement with the IC$_{50}$ for site 1 determined by solution binding assays, described above. Labeling of this 210 kDa protein band by [$^{125}$I]-SNX-111 was also inhibited by SNX-183 but with lower affinity (IC$_{50}$=300 pM). Similar experiments with [$^{125}$I]-SNX-183 revealed that in addition to the expected labeled band at 210–220 KDa, three additional bands at 172, 150 and 138 kDa appear to be specifically labeled (FIG. 10B).

Figure 11A:
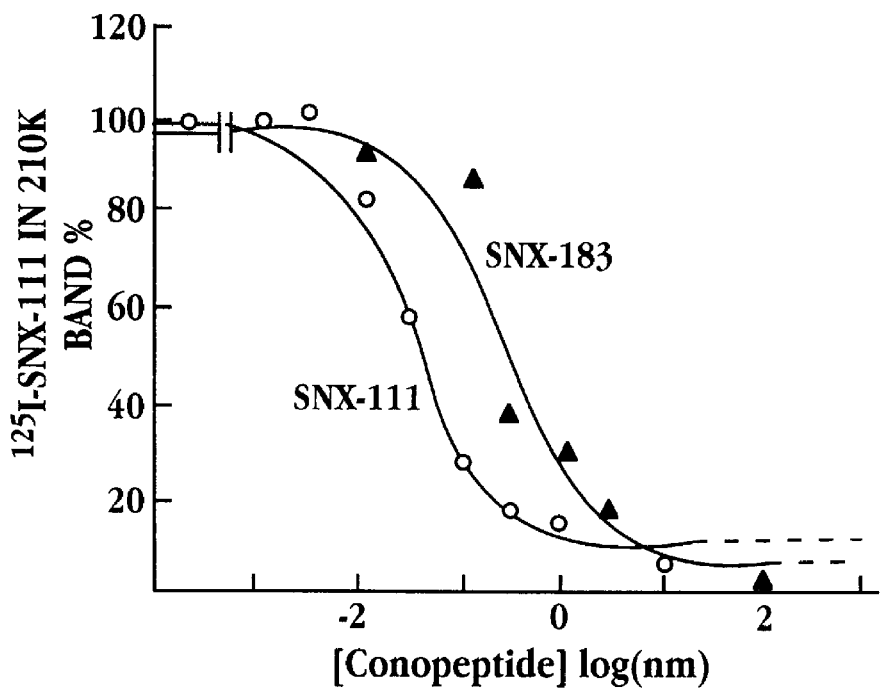
FIG. 11 shows plots of competition by unlabeled SNX-111 and SNX-183 for binding of [$^{125}$I]-SNX-111 (11A) and [$^{125}$I]-SNX-183 (11B) to the 210 kilodalton band of polypeptides present in rat synaptosomal membranes.
Figure 11B:
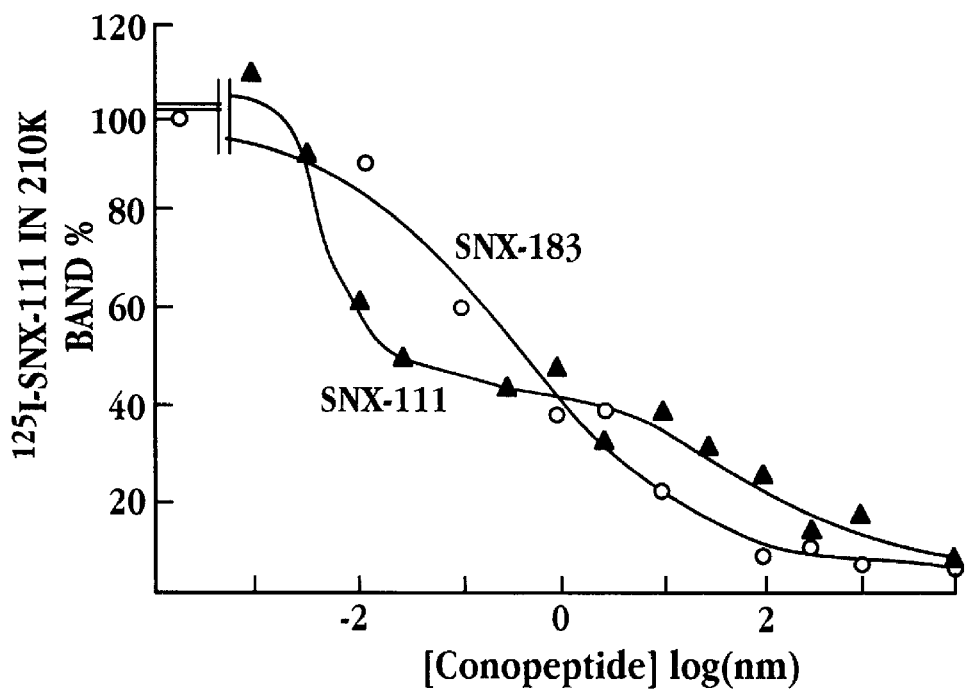

Analysis of the inhibition of incorporation of [$^{125}$I]-SNX-183 in the 210 kDa band by SNX-111 provides evidence for the presence of two distinct polypeptides of M$_r$ 210 kDa corresponding to site 1 and site 2. As shown in FIG. 1A, SNX-111 displaced [$^{125}$I]-SNX-183 from the 210 kDa polypeptide in a biphasic manner with IC$_{50}$ values of 6 pM and 65 nM. At low concentrations, SNX-111 effectively competed against [$^{125}$I]-SNX-183 for binding to site 1, while the binding of [$^{125}$I]-SNX-183 to site 2 was competitively displaced by SNX-111 only at much higher concentrations, as shown in FIG. 11B.

Inhibition of incorporation of [$^{125}$I]-SNX-183 into the 210 kDa band by SNX-183 is consistent with the ability of this compound to bind to both site 1 and site 2, but, as shown above, with much lower affinity than MVIIA (SNX-111) or TVIA (SNX-185) at site 1. The displacement curve displacement of MVIIA binding by SNX-183 is characteristically shallow, with an IC$_{50}$ of 360 pM (FIG. 11A). Taken together with the differential rank orders of binding affinities for omega-conopeptides at the two binding sites, as measured by displacement, these crosslinking experiments confirm that the primary binding sites of MVIIA and SNX-183 or SNX-230 are distinct molecular entities, both with M$_r$ 210–220 kD.

3. Localization of Binding of Omega-conopeptides in Nervous Tissue

The omega-conopeptide binding sites described above are distributed differentially throughout the nervous system. The regional distribution of sites 1 and 2 in rat brain sections were determined by autoradiography of brain sections exposed to the radiolabelled compounds, detailed in Example 5. The results presented in FIG. 12 show that the distribution of binding of [$^{125}$I]-SNX-111 is highly localized (A, B) and that non-specific binding is virtually non-existent (C, D). The pattern of binding is similar to that reported using [$^{125}$I]-GVIA preparations (Takemura). Comparison of the specific binding of [$^{125}$I]-SNX-111 and [$^{125}$I]-SNX-183 revealed overlapping but differential distribution of binding sites (E, F). Both ligands labeled the cortex, CA1, dentate gyrus and caudate-putamen. In these regions, binding of [$^{125}$I]-SNX-183 was unaffected by concentrations of SNX-111 which caused complete displacement of [$^{125}$I]-SNX-111 labeling (not shown), suggesting colocalization of sites 1 and 2. Greater abundance of site 2 in thalamic ventromedial lateral lobe and medial geniculate was revealed by the high density of binding of [$^{125}$I]-SNX-183 in these nuclei. In contrast, globus pallidus, Cop and substantia nigra were labeled only by [$^{125}$I]-SNX-111, indicating a preponderance of site 1 in these regions. The complete absence of [$^{125}$I]-SNX-183 binding in the substantia nigra suggests a third, distinct binding site recognized only by [$^{125}$I]-SNX-111, and by implication, a novel calcium channel subtype.

The identity of the sites was confirmed in each region by their relative affinities for the two conopeptides SNX-111 and SNX-183. Computer-aided densitometric analysis of the displacement of [$^{125}$I]-SNX-111 by SNX-183 in the different brain regions showed that the labeling of cortex and hippocampus by [$^{125}$I]-SNX-111 could be inhibited by lower concentrations of SNX-183 ($IC_{50}$ 100 nM), whereas higher concentrations of SNX-183 ($IC_{50}$ 300 nM) were needed to displace [$^{125}$I]-SNX-111 from the substantia nigra. Since a number of nuclei that are known to be rich in synapses and thus likely to contain a high density of presynaptic calcium channels were not labeled by either ligand, the two conopeptides can distinguish four different subtypes of neuronal binding sites, as summarized in Table 4. The four subtypes are, (i) those sensitive to both SNX-111 and SNX-183 (site 1), (ii) those sensitive to SNX-183 only, (site 2), (iii) those recognized by SNX-111 only and (iv) others recognized by neither conopeptide.

TABLE 4

Four classes of OCT binding site calcium channels

| Site | Binds SNX-111 | Binds SNX-183 | Examples |
| --- | --- | --- | --- |
| 1 | + | + | cortex, hippocampal CA1, CA3, thalamic nuclei, spinal cord (laminae I + II only) |
| 2 | − | + | cortex, hippocampal CA1, CA3, thalamic nuclei |
| 3 | − | − | midbrain nuclei, spinal grey matter (except laminae I + II), neuromuscular junction |
| 4 | + | − | substantia nigra, hippocampal CA2 |

4. Selective Inhibition of Neurotransmitter Release

Omega-conopeptides inhibit neurotransmitter release in various regions of the nervous system. As shown below, such inhibition varies according to the neurotransmitter, the omega-conopeptide, and the region studied. Neurotransmitters which can be measured, in accordance with various aspects of the invention, include, but are not limited to dopamine, norepinephrine, acetylcholine, GABA, glutamate, and a number of peptide neurotransmitters, such as substance P (McGeer).

Quantitation of release and inhibition thereof is determined by sensitive detection methods, also known in the art, including direct detection of release of endogenous stores by HPLC or specific radioimmunoassay (RIA), and detection of release of pre-loaded, labeled compound. Alternatively, or in addition, detection of release may be achieved using a number of indirect assays, exemplified by the electrophysiological studies described above, in which whole tissue response to electrical or chemical stimulation is measured.

Inhibition of release of the neurotransmitter norepinephrine from neuronal cells can be assayed in mammalian brain hippocampal slices by standard methods, such as detailed in Example 6A. Briefly, hippocampal slices are distributed to individual wells of a microtiter plate, and incubated with radiolabeled norepinephrine under conditions favoring cellular uptake of the transmitter. The cells are washed with a low-potassium medium, then bathed for 15 minutes in a high-potassium stimulation medium, in the presence of selected concentrations of a test compound. After removal of the stimulation buffer, radioactivity remaining in each slice is determined.

Figure 13A:
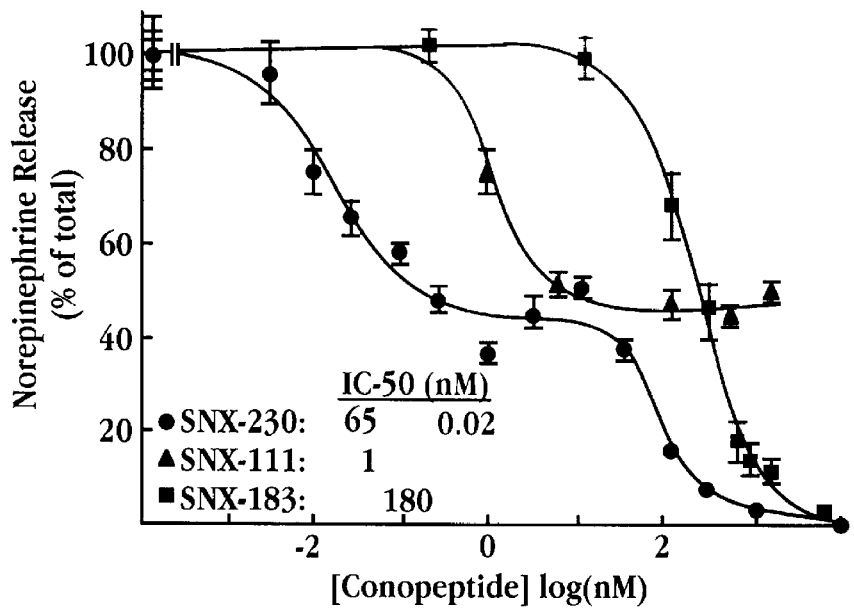
FIG. 13A shows a plot of inhibition of potassium-evoked norepinephrine release from neuronal tissue as a function of concentration of OCT peptides SNX-230 (closed circles), SNX-111 (closed triangles) or SNX-183 (closed squares)

FIG. 13A shows the effects of the three peptides SNX-111, SNX-183 and SNX-230 on the release of norepinephrine evoked by potassium depolarization, as detailed in Example 6A. SNX-111 inhibits release with high potency ($IC_{50}\approx1$ nM) but only partially (approx. 60%). SNX-183 is much less potent ($IC_{50}\approx180$ nM) but the inhibition is substantially 100%. SNX-230 also inhibits release completely, but in a biphasic manner, inhibiting approximately 50% with high potency ($IC_{50}\approx0.02$ nM) and 50% with much lower potency ($IC_{50}=65$ nM). In agreement with the binding studies discussed above, these results show that such norepinephrine release is mediated by at least two distinct subtypes of presynaptic calcium channels, one of which corresponds to the site 1 receptor identified by high affinity for SNX-111 and the other to the site 2 receptor recognized preferentially by SNX-230.

Table 5 shows $IC_{50}$ values for a variety of omega-conopeptides for inhibition of norepinephrine release. These values represent average $IC_{50}$ values calculated from thin (200$\mu$) and thick (400$\mu$) hippocampal slices. The three lowest $IC_{50}$ values, between 0.8 and 2.4 nM, correspond to omega-conopeptides which are most potent in this assay.

TABLE 5

Inhibition of Norepinephrine Release by Omega-conopeptides

| omega-conopeptides | $IC_{50}$ (nM) |
| --- | --- |
| GVIA (SNX-124) | 0.8 |
| MVIIA (SNX-111) | 1.5 |
| TVIA (SNX-185) | 2.4 |
| SNX-201 | 11 |
| SNX-195 | 11 |
| SNX-202 | 29 |
| SVIB (SNX-183) | 200 |
| SNX-191 | >100 |
| SVIA (SNX-157) | >4500 |

Effects of omega-conopeptides were also compared to those of OCT GVIA and amiodipine, an L-channel blocker, on potassium-stimulated release of dopamine and acetylcholine from slices of rat brain (striatal region) as described in Example 6. Briefly, in these experiments, striatal slices from rat brain were preloaded with radiolabelled dopamine or choline, then perfused for 45 minutes with bathing media. Slices were subjected to an S1 stimulus, consisting of addition of 15 mM potassium chloride to the bathing medium for 1 minute. Total outflow of radiolabeled neurotransmitter in response to S1 was measured. Slices were then washed, exposed to test compound for 20 minutes, then subjected to an S2 stimulus, as above. Comparison of outflow of neurotransmitter in response to S2 to outflow in response to S1 is a measure of drug effects on the system. Results are given as percent inhibition of release in Tables 6 and 7.

TABLE 6

Effect of Omega-Conopeptides and Amiodipine on
[³H] Dopamine Release from Striatal Slices

| Compound | Concentration | % inhibition |
|---|---|---|
| GVIA | 1 nM | 5 |
|  | 10 nM | 52 |
| MVIIA | 1 nM | 6 |
|  | 10 nM | 49 |
| Amiodipine | 1000 nM | 0 |

TABLE 7

Effect of Omega-Conopeptides and Amiodipine on
[³H] Acetylcholine Release from Striatal Slices

| Compound | Concentration | % inhibition |
|---|---|---|
| GVIA | 3 nM | 50 |
| MVIIA | 5.5 nM | 50 |
| Amiodipine | 1000 nM | 0 |

Figure 13B:
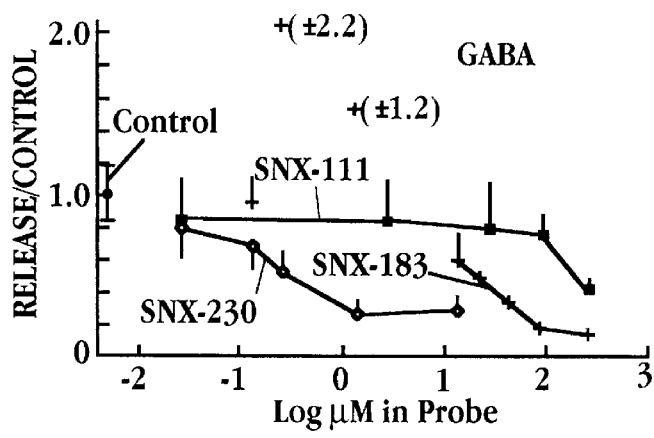
FIGS. 13B and 13C show plots of the fraction of control potassium-evoked in vivo release of GABA (13B) and glutamate (13B) in the presence of varying concentrations of conopeptides.
Figure 13C:
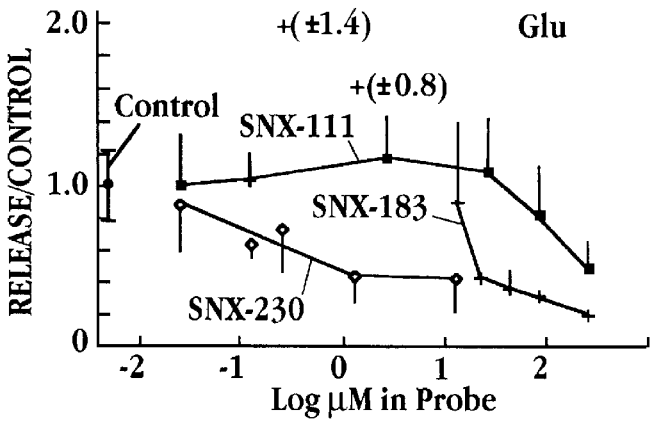

Neurotransmitter release can additionally be measured using in vivo microdialysis techniques (Ungerstadt, Westerlink, Benveniste) detailed in Example 6. Briefly, microdialysis probes were implanted stereotaxically into the hippocampal region of anesthetized rats. Local neurotransmitter release was stimulated by potassium ion depolarization of the region. Extracellular perfusate was analyzed for the presence of amino acid neurotransmitters glutamate and GABA before and after depolarization. Conopeptides SNX-111, SNX-183 and SNX-230 were tested for ability to attenuate release of GABA and glutamate. FIGS. 13B and 13C show plots of the fraction of control potassium-evoked release of GABA and glutamate in the hippocampus in the presence of varying concentrations of the conopeptides. These data were obtained from 3–7 separate experiments at each concentration of compound. From these experiments potency of inhibition of release by the conopeptides is estimated. Half maximal block of release of both glutamate and GABA occurred at concentrations of about 200 nM SNX-230, 20 $\mu$M SNX-183, and 200 $\mu$M SNX-111 in the hippocampal region.

Further means of measuring inhibition of neuronal transmitter release are isolated tissue assays, such as atrial strip, aorta, vas deferens and guinea pig ileum assays, in which the response to a stimulus, usually an electrical stimulus, is correlated to the amount of neurotransmitter released from neurons innervating the tissue (Kenakin). In the guinea pig ileum, inhibition of electrically stimulated contractions is correlated with inhibition of acetylcholine release, as demonstrated by the ability of cholinergic agonists to overcome such inhibition. Example 7E describes the preparation and assay in detail. Table 8 shows the $IC_{50}$ values for various omega-conopeptides on contraction of guinea pig ileum in response to electrical stimulation.

TABLE 8

Effects of Conopeptides on Electrically
Stimulated Contraction of Guinea Pig Ileum

| Compound | $IC_{50}$ (nM) |
|---|---|
| SNX-111 | 13 |
| SNX-185 | 29 |

TABLE 8-continued

Effects of Conopeptides on Electrically
Stimulated Contraction of Guinea Pig Ileum

| Compound | $IC_{50}$ (nM) |
|---|---|
| SNX-183 | 91 |
| SNX-157 | >100 |

5. Sympatholytic Activity

In accordance with the present invention, it has been determined that omega-conopeptides have sympatholytic properties. Such properties are conveniently measured in an anesthetized rat preparation in which sympathetic outflow to the vasculature has been removed from central control by ablation of the lower brain and spinal cord and by pharmacological manipulation as described in Example 10 ("pithed rat"). Subsequent electrical stimulation of the spinal cord selectively activates sympathetic outflow to the vasculature. Sympathetic activation can be determined in such a preparation by monitoring arterial blood pressure.

Figure 21:
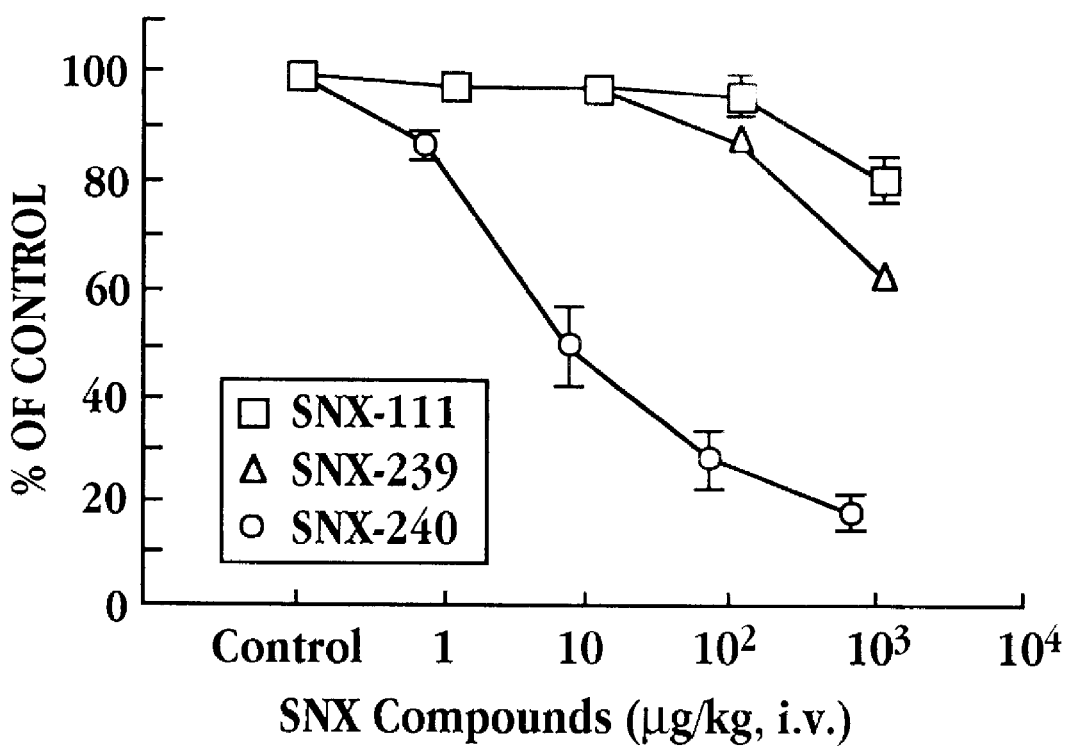
FIG. 21 shows the effects of SNX-111 (open circles), SNX-239 (open triangles) and SNX-240 (open squares) on stimulated arterial blood pressure in a pithed rat model.

FIG. 21 shows the results of studies in which SNX-111, SNX-239, and SNX-240 were tested at various doses for ability to block sympathetic outflow, as evidenced by a reduction in stimulated arterial blood pressure. Differential effects of these compounds on stimulated arterial blood pressure are apparent in this system. Whereas a dose of 1 mg/kg SNX-111 resulted in reduction by about 80% of stimulated arterial blood pressure, SNX-239 and SNX-240 were considerably less effective as sympatholytic agents. At a dose of 1 mg/kg, SNX-239 reduced stimulated blood pressure by about 35%, and SNX-240 reduced stimulated blood pressure by less than 20%. From the data presented, it can be estimated that SNX-239 is at least about 200 fold less potent as a sympatholytic agent than is SNX-111, when this activity is measured in the pithed rat model.

II. Treatment of Pain

In accordance with one aspect of the invention, it has been discovered that selected omega-conopeptides are analgesic. Analgesic omega-conopeptides are those which are effective (a) to inhibit voltage-gated calcium channels selectively in neuronal tissue, as evidenced by the peptide's ability to inhibit electrically stimulated contraction of the guinea pig ileum, and (b) to bind to omega conopeptide MVIIA binding sites present in neuronal tissue. Such binding to omega conopeptide MVIIA binding sites (site 1, as described herein) is selective, as evidenced by relatively high binding affinity at such sites, as compared to binding at an omega conopeptide site 2 (described herein as a high affinity binding site for SNX-230 or SNX-183). Such selectivity can be measured by the selectivity ratio illustrated in Tables 3A and 3B, above.

Moreover, in accordance with the invention it has been found that analgesic omega-conopeptides are effective as analgesic agents both in traditional opiate-sensitive models of nociceptive pain, such as the Rat Tail-Flick model or the rat formalin model, as well as in opiate-resistant models of pain, such as the allodynia model of neuropathic pain. These models, and results of omega-conopeptides in these models are described below.

A. Omega-Conopeptides

Omega-conopeptides useful in the treatment of pain have been found, in accordance with the invention, to conform to certain physical and chemical constraints, as described below. Generally, omega-conopeptides useful in the treatment methods are those which are 25–35 amino acids in length and which have three disulfide bonds at specified positions along their length.

Based on a sequence homology analysis of the peptides whose full sequences are known (FIG. 1), the naturally occurring active omega-conopeptides were grouped into distinct groups I and II, each with internal homologies distinct to that group, as can be appreciated from FIG. 14. Group I includes active omega-conopeptides MVIIA (SNX-111), MVIIB (SNX-159) and SNX-239, which possess binding constants to the MVIIA site within the range of compounds showing activity in treating pain. Group II includes TVIA (SNX-185), SNX-207 and SNX-236, which also possess binding constants in the range of compounds for analgesia. A third group includes inactive peptides SNX-231, and SVIA (SNX-157) and omega-conopeptides whose binding activities for the MVIIA site on neuronal membranes and/or activity in norepinephrine inhibition are outside the range of active compounds.

The three groups of omega-conopeptides are arranged in FIG. 14 with their six Cys residues aligned, which places these residues at positions 1, 8, 15, 16, 20, and 28. To make this alignment, gaps were introduced at the positions shown in the three groups. In the analysis below, these gaps retain the assigned number shown in FIG. 14, even though they represent amino acid deletions in the respective groups of active omega-conopeptides.

Sequence variation in the peptides, based on primary structure alone, was analyzed by adopting the following constraints:

1. The peptides in both active groups (I and II) include the Cys residues at position 1, 8, 15, 16, 20, and 28. Other Cys residues could be substituted at the positions indicated below only if they are selectively protected during oxidation of the peptide to form the three disulfide linkages.

2. The peptides in the active groups include three disulfide linkages connecting the Cys residues at positions 1 and 16, 8 and 20, and 15 and 28. As described above, the disulfide bridges are formed by air oxidation of the full sequence peptide in the presence of DTT. The ability of the peptide to form the three desired disulfide linkages would therefore require that the peptide, prior to disulfide bridging, be able to adopt a conformation which allows the three selected linkages, with or without the Cys protecting-group strategy discussed above. This constraint would thus exclude amino acid variations which prevent or otherwise hinder the formation of the three selected bridges.

Constraints 1 and 2 preserve the basic conformation of the omega-conopeptides imposed by the three disulfide bridges.

3. Within Group I, the amino acid variations which occur at the six non-conserved residues are allowed, including peptides in which the carboxy terminus is amidated or has a free acid form. That is, the first group compound derivatives include the peptide structures having the form: SEQ ID NO: 22-$X_1$-SEQ ID NO: 23-$X_2$-$X_3$-$X_4$-$X_5$-SEQ ID NO: 24-$X_6$-SEQ ID NO: 25-$X_7$-SEQ ID NO: 26-t, where $X_1$=K or S; $X_2$=S or H; $X_3$=R, L, or A; $X_4$=L or T; $X_5$=M or S; $X_6$=N or a deletion; SEQ ID NO 25 is R; $X_7$=S or deletion, and t=a carboxy or amidated/carboxyterminal group, and where SEQ ID NO: 22 is C K G K G A; SEQ ID NO: 23 is C; SEQ ID NO: 24 is Y D C C T G S C; and SEQ ID NO: 26 is G K C.

4. Within Group II, the amino acid variations which occur at the eight non-conserved residues are allowed, including peptides in which the carboxy terminus is amidated or has a free acid form. Thus, the second group compound derivatives include the peptide structures having the form: SEQ ID NO: 27-$X_1X_2X_3$-SEQ ID NO: 28-$X_4$-SEQ ID NO: 31-t, where $X_1$=X or R; $X_2$=T or L; $X_3$=S or M, $X_4$=X or P; and t=a carboxy or amidated carboxyterminal group, and where SEQ ID NO: 27 is C L S X G S S C S; SEQ ID NO: 28 is Y N C C R S C N; and SEQ ID NO. 31 is Y S R K C R.

5. Considering both active groups together, amino acid positions which are conserved in all active species are preserved. Thus, for example, the Cys residues, the 5-position glycine, the 13-position tyrosine, the 19-position serine, and the 26-position lysine are all preserved. Preferred OCT analogs or derivatives may be selected by comparing, for purposes of inter-sequence conservation and substitution, those sequences known to be active. For example, in the case of the treatment of pain, omega-conopeptides MVIIA (SNX-111), SNX-239, SNX-199, TVIA (SNX-185) and SNX-236 are known active compounds. Active derivatives are those peptides having, in addition to the conserved cysteine residues described above, a conserved glycine residue at position 5, conserved serine residues at positions 9, 19, and 24, and a conserved lysine residue at position 26. Inter-sequence substitution of variable residues is then preferable in the formation of active analogs. For example, analog position 2 may be occupied by a lysine or a leucine residue, and position 6 may be occupied by an alanine or a serine residue.

6. Considering both active groups together, there are amino acid positions which are likely to be variable within the range of active species. For example, the position 2 amino acid may be lysine or leucine, the position-3 amino acid may be glycine or serine, and the position 4 amino acid, hydroxyproline or arginine. In addition, if the two or more amino acids at a variant position are in a common substitution class, substitution within that class may be favorable. Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Ser, Thr, Pro, Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and a halogenated tyrosine in Group VI. Further, the classes may include both L and D stereoisomers, although L-amino acids are preferred for substitutions. 7. Considering the known inactive species, substitutions to amino acids which are present in inactive species, but not active ones, at any selected residue position, are not favored to preserve activity in the active compounds. Thus, for example, although a 3-position serine is present in both active and inactive compounds, 4-position serine or threonine is present in inactive species only, and either substitution is thus disfavored.

The above amino acid selection rules 6–7 are intended as a guide for allowed amino acid substitutions within active omega-conopeptides. Once an amino acid substitution or modification is made, the peptide is further screened for the requisite calcium channel antagonist activity, and the requisite activities for inhibition of neurotransmitter release and binding to the appropriate OCT binding site of neuronal membranes, as described above.

Several of the amino acid substitutions or modifications to the omega-conopeptide illustrate the principles outlined above.

Omega-conopeptides which are selected on the basis of these criteria, discussed in detail below, are tested for ability to produce analgesia in a standard test of analgesia, such as the Rat Tail-Flick test, wherein analgesia is measured by a prolongation of reaction time to a noxious radiant heat stimulus.

B. In vitro Properties of Analgesic Omega-conopeptides

1. Calcium Channel Blocking Activity

Calcium channel blocking activity was measured electrophysiologically in neuronal (N1E-115 or IMR-32) cell lines, as described in Section II, above, and in detail in Example 2. Omega-conopeptides having calcium channel blocking activity are those which block calcium currents in such cell lines with potencies in the range observed for omega-conopeptides MVIIA and GVIA in N1E-115 cells.

2. High Affinity Binding to OCT Binding Sites

Methods for determination of binding affinity to OCT binding sites are discussed in Examples 3–4, below.

Experiments testing reversibility of binding of SNX-111, SNX-183 and SNX-124 revealed that SNX-111 and SNX-183 exhibited dissociation half-times of two and five minutes, respectively. In contrast, SNX-124 did not dissociate appreciably from its binding site(s), even 1 hour following addition of excess unlabelled compound, indicating that SNX-124 binds irreversibly to its binding site in neuronal membranes.

Compounds were tested for their ability to displace binding of SNX-111, SNX-183, or SNX-230 from their respective binding sites (site 1 and site 2, as described above). In displacing SNX-111, it was found that compounds having analgesic activity, such as OCT MVIIA (SNX-111), SNX-239, SNX-236, SNX-199 SNX-159 and TVIA (SNX-185), have $IC_{50}$ values between about 15 and 300 pM, and $K_i$ values between about 1 and 100 pM. In contrast inactive compound SNX-183 had an $IC_{50}$ of greater than 1000 pM for binding at the MVIIA site.

From the foregoing, it is seen that active compounds in accordance with the invention are characterized by a high binding affinity for MVIIA binding site 1. The binding affinity for these sites may be characterized as follows. In the first approach, the binding affinity of the compound for binding site 1, as estimated by $IC_{50}$ in displacing MVIIA from the site, is compared directly with those of selected high affinity active compounds, such as SNX-111 and SNX-185. An active compound is one whose binding affinity is at least as high as and preferably within the range of binding affinities measured for such high affinity OCT's. Secondly, the binding affinity of the test compound can be characterized by binding to binding site 2, as estimated by $IC_{50}$ in displacing MVIIC (SNX-230) or SVIB (SNX-183) from the site. Thirdly, the binding affinity of the compound can be characterized by the ratio of binding constants or relative affinities of the compound for site 1 and site 2, as just described. Here an active compound is one whose binding ratio is within the range for the selected active peptides, such as MVIIA (SNX-111) and TVIA (SNX-185); i.e., the binding ratio is substantially within the range of the ratio observed for the omega-conopeptides MVIIA and TVIA.

A number of omega-conopeptide compounds which were tested gave $IC_{50}$ and $K_i$ values lower than or within the ranges of those of omega-conopeptides MVIIA (SNX-111) and TVIA (SNX-185) for binding at the SNX-111 site, as shown in Table 2, and these compounds should thus be considered candidates as analgesic compounds. In addition active compounds have relatively high selectivities of binding, equivalent or greater than those of MVIIA and TVIA, as shown in Tables 3A and 3B. However, some of these compounds, may not fulfill additional criteria for analgesic compounds of the invention, as described herein.

3. Localization of OCT Binding in the Central Nervous System

Conopeptide SNX-111 binds to distinct regions of the brain and spinal cord which are commonly associated with pain pathways (FIG. 12). These include the periaquaductal grey (PAG) region of the brain and the dorsal horn of the spinal cord. The distribution of CgTx (GVIA) binding shown by Takemura et al (1989) also shows localization of CgTx binding sites at a very high level in the dorsal horn of the spinal cord ($1^{st}$ and $2^{nd}$ layers of Rexed) and, to a lesser degree, in the central grey region of the mesencephalon, which may correspond to the PAG; however, some of these compounds may not fulfill additional criteria for analgesic compounds of the invention, as described herein.

4. Inhibition of Neurotransmitter Release

Another requisite property of analgesic OCT compounds, in accordance with the invention, is their ability to specifically inhibit depolarization-evoked and calcium-dependent neurotransmitter release from neurons. For example, it is shown here that analgesic omega-conopeptides inhibit of electrically stimulated release of acetylcholine at the myenteric plexus of the guinea pig ileum (Example 6E). This inhibition is associated anti-nociceptive activity, as seen in Table 8. Omega-conopeptides having analgesic activity have $IC_{50}$'s in the range of those values observed for active omega-conopeptides MVIIA (SNX-111) and TVIA (SNX-185), or less than approximately 50 nM, as observed in this assay.

5. In vivo Measurements of Analgesia

Analgesia is conveniently measured in one or more of a number of animal models, in which an animal's response to a given pain stimulus is measured.

a. Rat Tail-Flick Test

The rat tail-flick is a standard test in which latency of animal response to noxious stimulus (heat) is determined. This test is described in Example 7. Briefly, a rat is positioned such that its tail is exposed to a standard heat source, and the time that the animal voluntarily endures the heat, prior to moving its tail, is recorded. Analgesics, particularly opioid analgesics, prolong this time.

Figure 15:
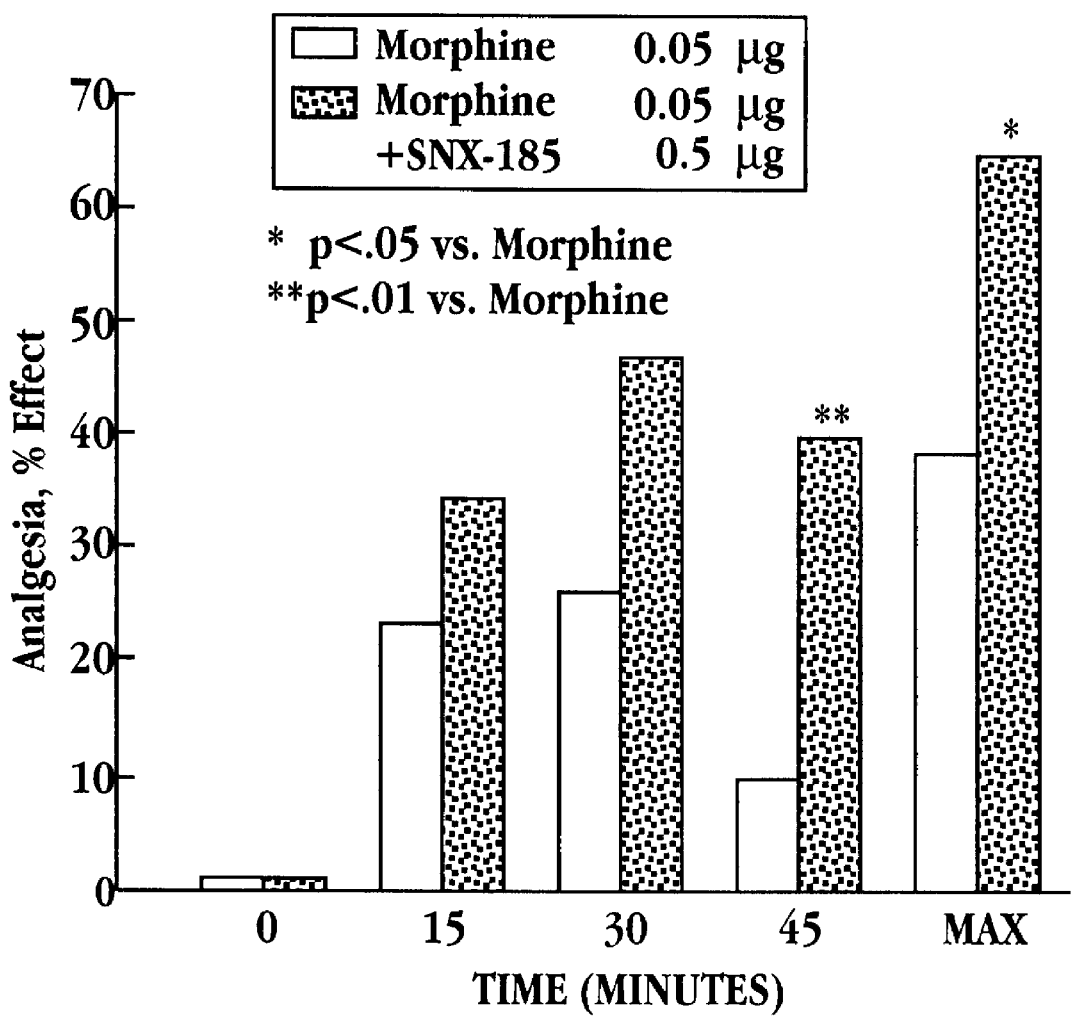
FIG. 15 shows the production of analgesia by a submaximal intrathecal dose of morphine (0.5 μg) administered alone (solid bars) and in the presence of 0.5 μg SNX-185 (hatched bars)
Figure 16A:
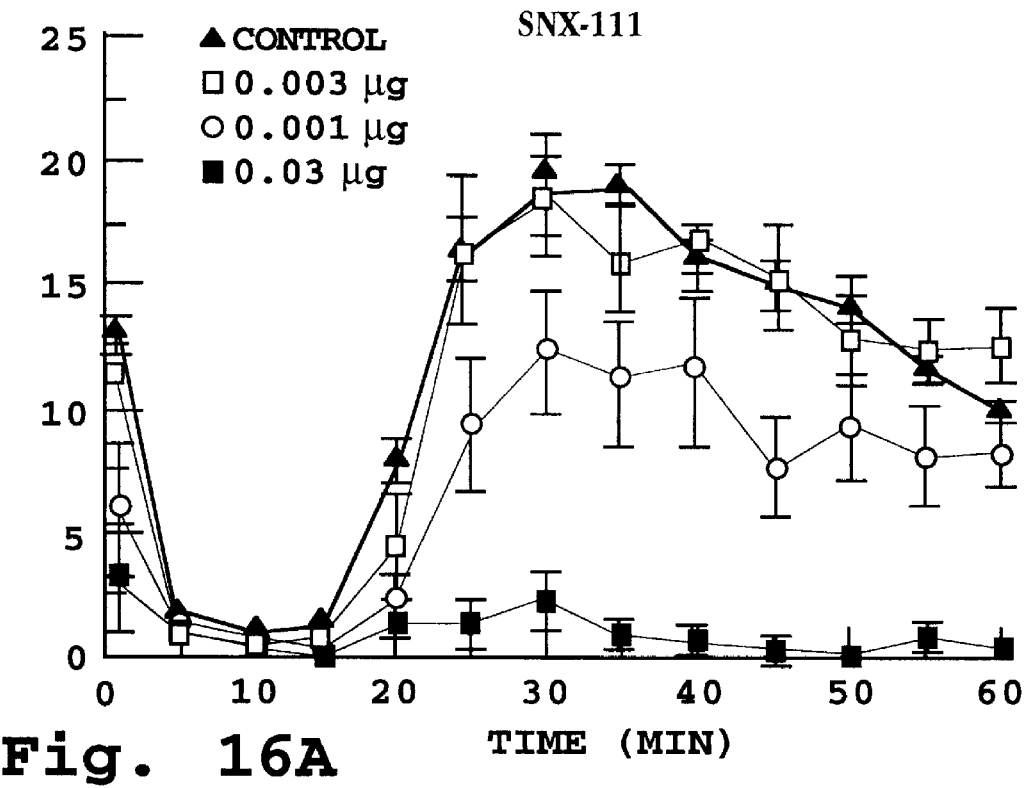
FIGS. 16(A–G) shows effects of varying doses of SNX-111(A), SNX-185(B), SNX-159 (C), SNX-199 (D), SNX-239 (E), SNX-231(F), and SNX-236 (G) on flinch response in rat formalin tests.
Figure 16B:
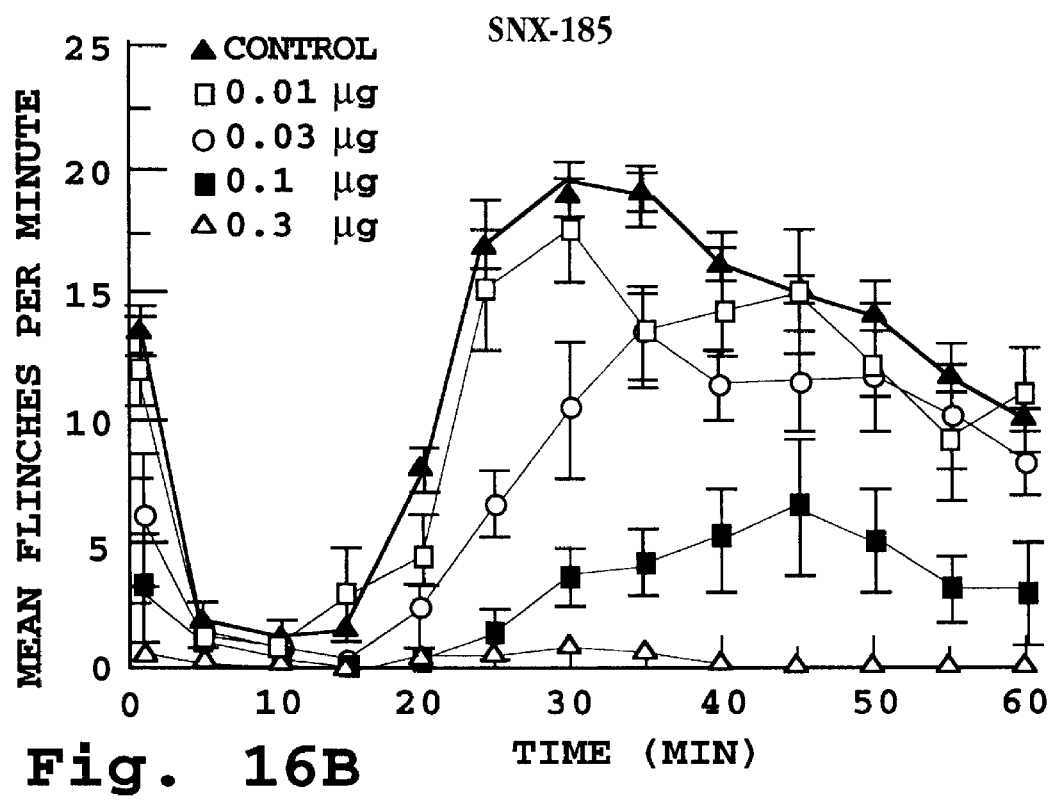
Figure 16C:
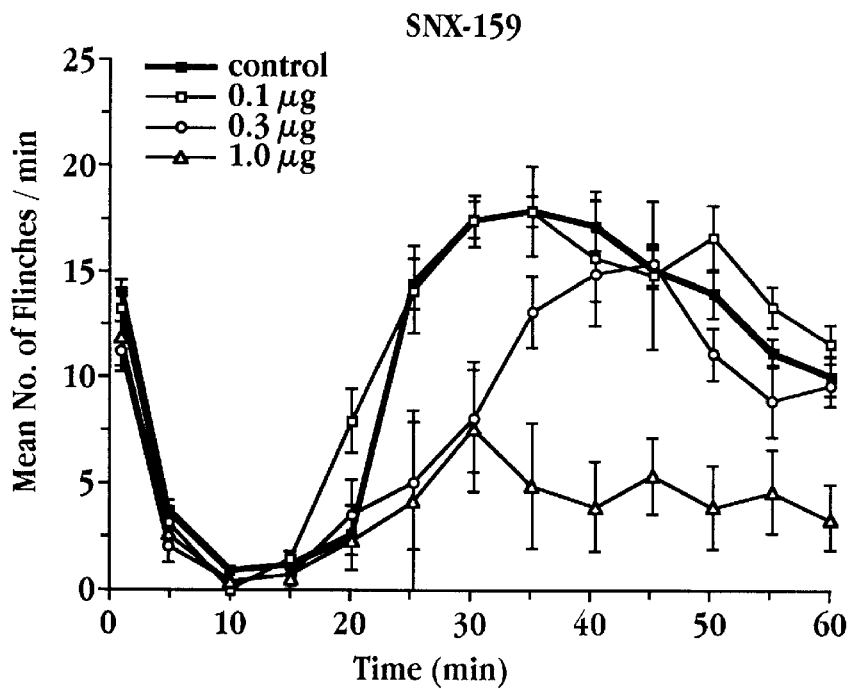
Figure 16D:
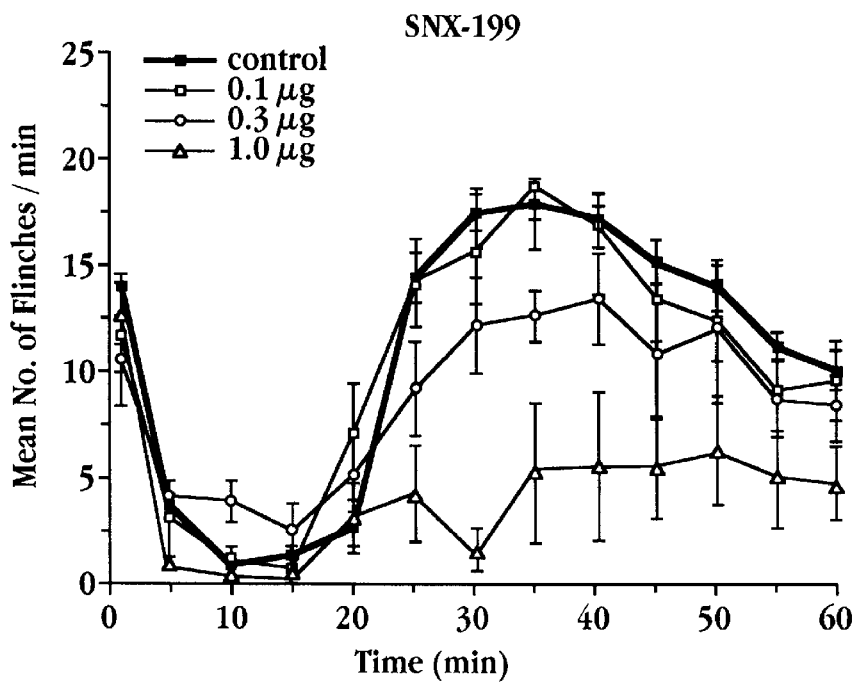
Figure 16E:
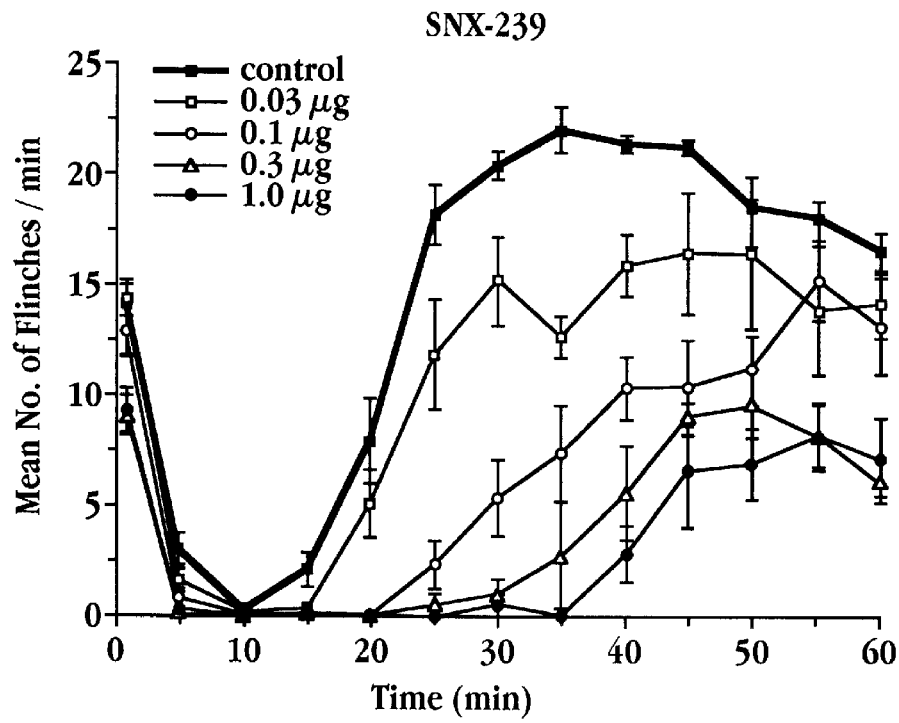
Figure 16F:
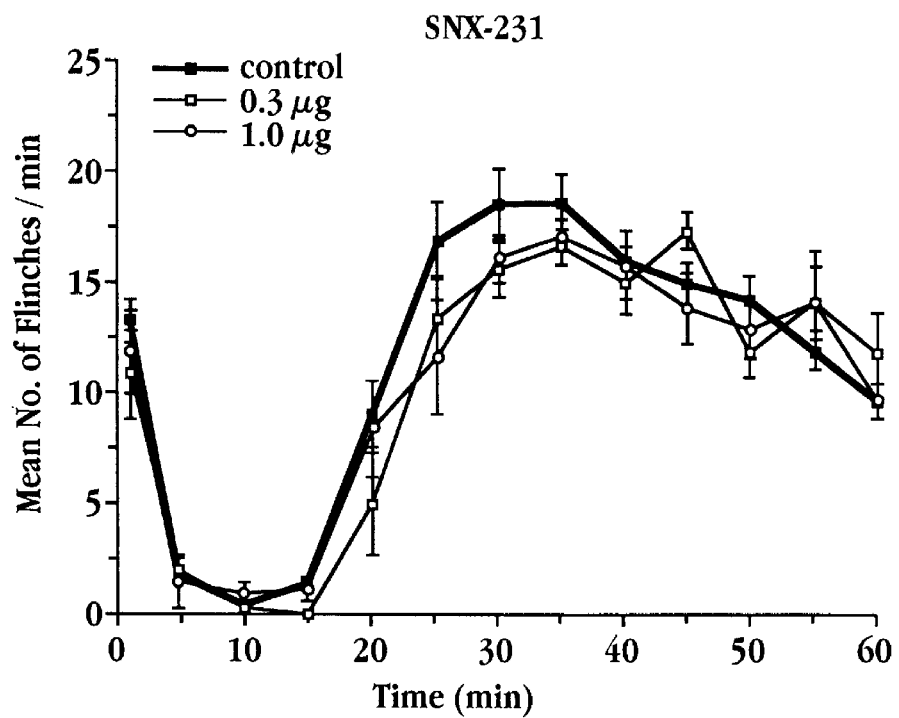
Figure 16G:
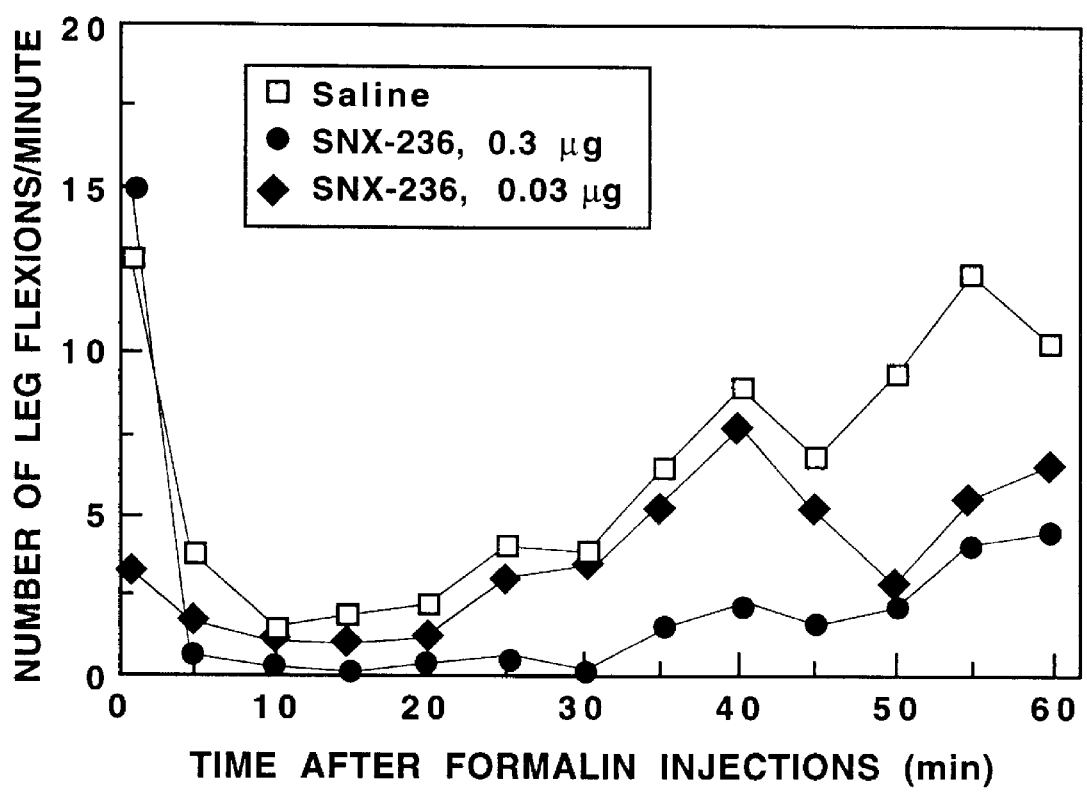

Shown in FIG. 15 are the results of experiments in which the effects of a sub-maximal dose of morphine were compared to those of the combination of a sub-maximal dose of morphine and a 0.5 μg (intrathecal) dose of SNX-185 in the Rat Tail-Flick Test. Intrathecal administration of SNX-185 enhanced the effects of a sub-maximal dose of morphine (FIG. 15) in this assay at all time points, and significantly at 45 min. after administration of compound.

b. Rat Formalin Test

The rat formalin test is another in vivo test of analgesic potency. This test reflects several levels of processing of nociceptive information in the spinal cord (see Wheeler-Aceto, et al., 1990; Wheeler-Aceto, et al., 1991). Protracted sensory input generated by the noxious stimulus employed in this test (formalin in the paw) has been shown to induce an acute pain response phase (phase 1) followed by a second phase (phase 2). This second phase is thought to represent a state of facilitated processing evoked by the afferent input present during phase 1 and to involve release of at least two substances, glutamate and a tachykinin, based on other pharmacological evidence (Yamamoto and Yaksh, 1991, 1992).

In the rat formalin test, a standard dose of formalin is injected into the rat paw, and flexions of the paw are quantitated over the following 60 minute period (Example 8). A biphasic response pattern is typically observed, with numerous responses observed during the period 5 min. after injection (Phase 1) and a second phase (Phase 2) which occurs during the period about 10–60 minutes following injection, in which the mean number of flinches per minute is recorded as a function of time. This pattern is illustrated by the graphs shown in FIGS. 16(A–G). Quantitation of responses during each phase is made by calculation of area under the curve of flinches/min. as described in Example 8.

FIGS. 16(A–G) shows results of experiments in which varying doses of SNX-111, SNX-185, SNX-159, SNX-199, SNX-239, SNX-231 and SNX-236 were tested for effects on the formalin response in rats. FIG. 17 shows dose-response curves generated from these data. SNX-111, SNX-185, SNX-236 and SNX-239 each exhibited potent and maximal inhibition of the Phase 2 response, while SNX-159 and SNX-199 were somewhat less potent in this regard. SNX-111 and SNX-185 likewise showed maximal inhibition of the phase 1 response, while SNX-239 produced less than 50% inhibition of Phase 1 response at the highest doses tested (0.3 and 1 $\mu$g). SNX-231 was inactive in both Phase 1 and Phase 2 responses. From the dose response curves, $ED_{50}$ doses (doses which produced approximately 50% inhibition) were determined separately for Phase 1 and Phase 2 responses. These doses are summarized in Table 9.

TABLE 9

$ED_{50}$ for Intrathecal Conopeptides on Phase 1 and Phase 2 of the Formalin Test

| Drug | N† | $ED_{50}$ ($\mu$g, IT) ± 95% CI Phase 1 | Phase 2 |
|---|---|---|---|
| SNX-111 | 21 | 0.011 (0.005–0.022) | 0.011 (0.007–0.015) |
| SNX-185 | 20 | 0.043 (0.030–0.061)‡ | 0.041 (0.03–0.06) |
| SNX-239 | 12 | 0.54 (0.09–2.2) | 0.052 (0.02–0.23) |
| SNX-159 | 12 | >1.0 $\mu$g | 0.47 (0.04–5.2) |
| SNX-199 | 12 | >1.0 $\mu$g | 0.76 (0.01–57) |
| SNX-231 | 12 | >1.0 $\mu$g | >1.0 |

†N = number of animals in the dose-responsive curve for calculation of $ED_{50}$.
‡$ED_{50}$ values were estimated from the 3 lower doses (0.03–0.3 $\mu$g) on the dose-responsive curve because the higher dose (1.0 $\mu$g) did not produce any additional effect (both 1.0 $\mu$g and 0.3 $\mu$g produced approximately a 50% reduction of the phase 1).

Figure 18:
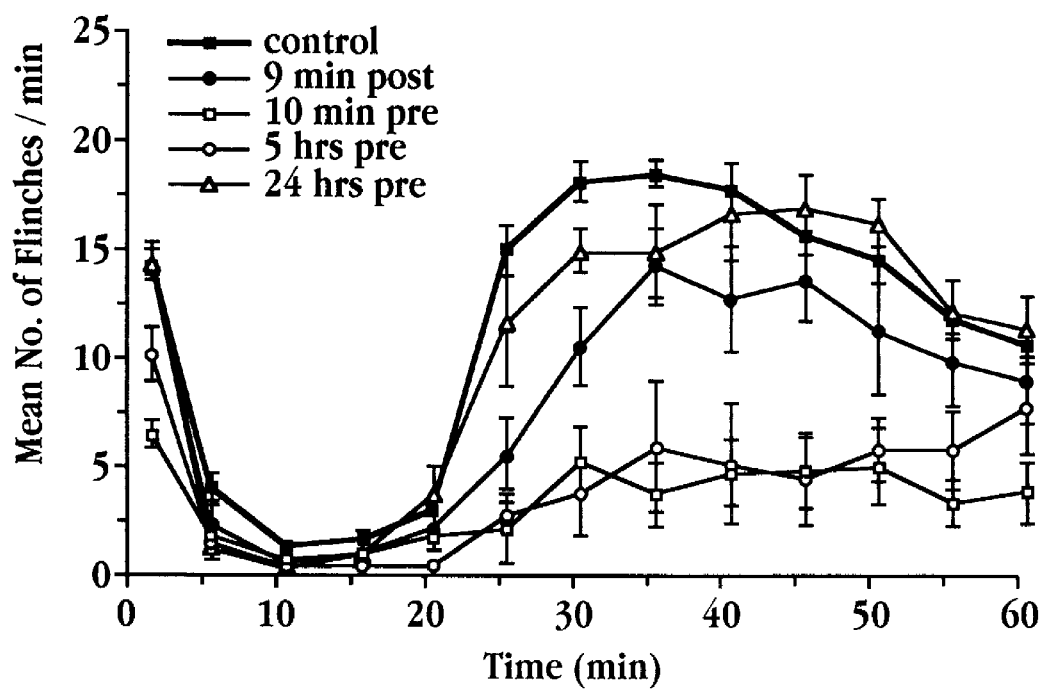
FIG. 18 shows time effect curves for effects of SNX-111 delivered 9 minutes, 10 minutes, 5 hours, or 24 hours prior to injection of formalin in the formalin test.

FIG. 18 shows the results of studies in which time of administration of SNX-111 was tested. SNX-111 was administered 9 minutes after (closed squares), 10 minutes before (open squares), 5 hours before (open circles) or 24 hours before (open triangles) injection of formalin. Significant reduction in pain response was observed in all except the 24 hour pre-treatment paradigm.

Figure 22A:
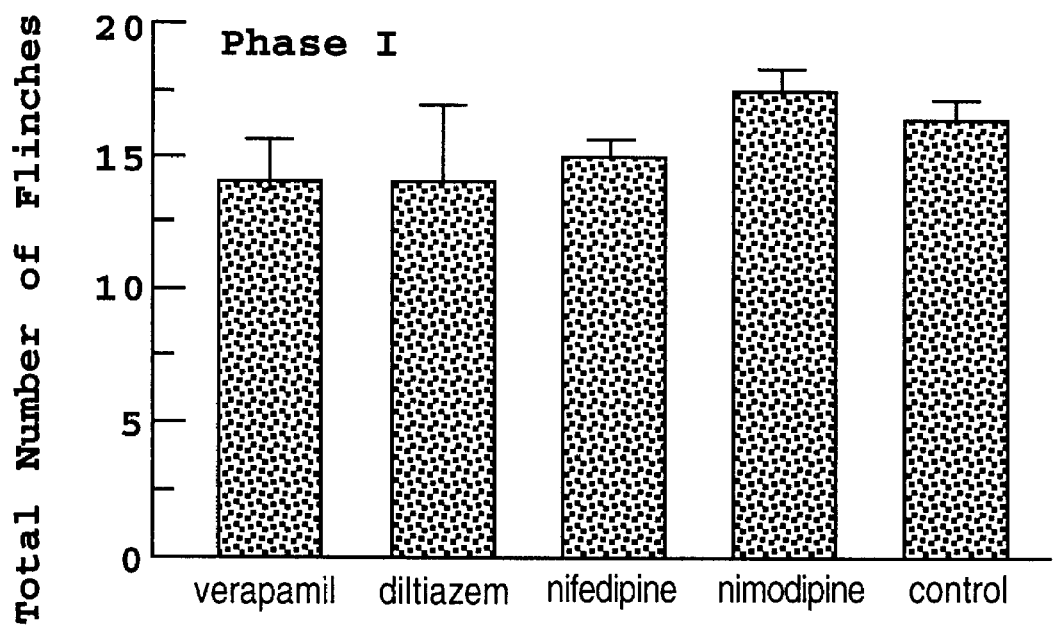
FIG. 22(A,B) shows the effects of L-type calcium channel blockers verapamil, diltiazem, nifedipine, and nimodipine on Phase 1(22A) and Phase 2(22B) in the rat formalin test.
Figure 22B:
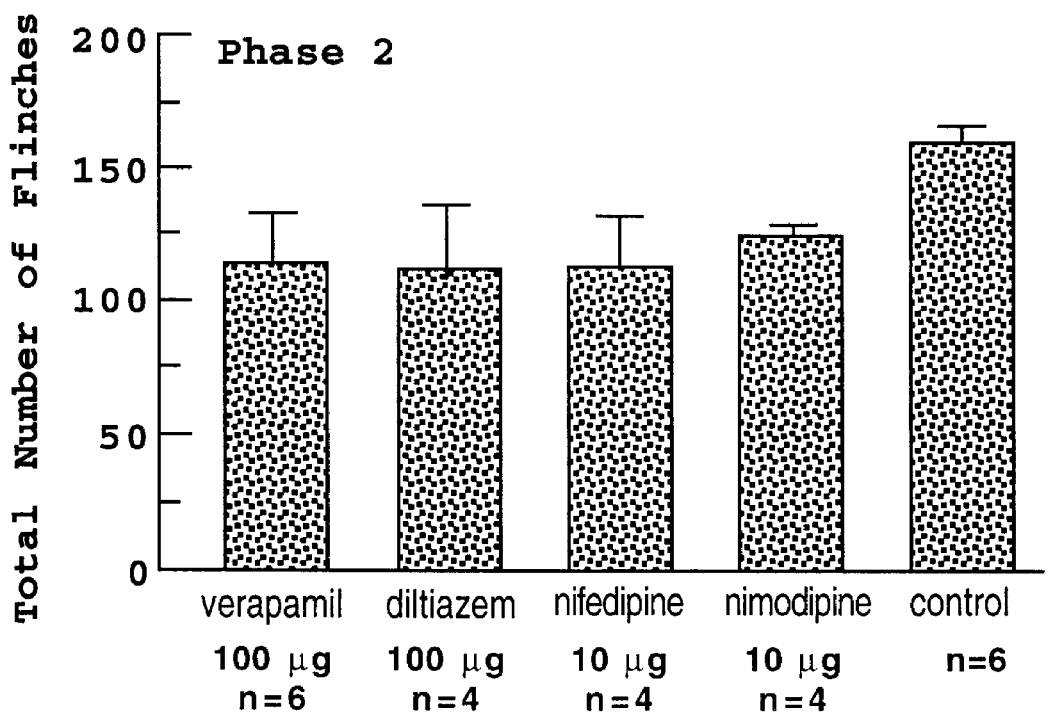

In separate studies, L-type calcium channel blocking dihydropyridine compounds nifedipine and nimodipine, as well as verapamil and diltiazem were without effect on Phase 1 and Phase 2 pain responses in the rat formalin test. The data for effects on Phase 1 and Phase 2 responses are summarized in FIGS. 22(A and B, respectively).

c. Neuropathic Pain Models

Analgesic potency of conopeptides can also be tested in animal models of neuropathic or neurogenic pain. One such model resembles the human condition termed causalgia or reflex sympathetic dystrophy (RSD) secondary to injury of a peripheral nerve. This condition is characterized by hyperesthesia (enhanced sensitivity to a natural stimulus), hyperalgesia (abnormal sensitivity to pain), allodynia (widespread tenderness, characterized by hypersensitivity to tactile stimuli), and spontaneous burning pain. In humans, neuropathic pain tends to be chronic and may be debilitating. This type of pain is generally considered to be non-responsive or only partially responsive to conventional opioid analgesic regiments (Jadad). In accordance with the invention, analgesic omega conotoxin peptides are effective in providing relief of neuropathic pain, as described below.

Experiments carried out in support of the present invention were performed in a rat model of peripheral neuropathy detailed in Example 9. Briefly, in the model used, rats are subjected to a surgical procedure, described by Kim et al. and Bennett et al., designed to reproducibly injure peripheral nerves (spinal nerves L5 and L6). These rats develop a hyperesthetic state, which can be measured, using one or more paradigms known in the art. Here, allodynia was measured by stimulation of neuropathic rat hindlimb using wire hairs having graded degrees of stiffness. Analgesic compounds reverse the heightened sensitivity such animals exhibit to the stimulus.

FIG. 19 shows results in the allodynia test of animals treated with SNX-111 (19A), SNX-239 (19B), SNX-159 (19C) and SNX-230. Data are expressed as percent maximum effect, where the maximum effect indicates a complete reversal of surgically induced allodynia, or relative insensitivity to stimulus (maximum equals 15 gram hair stimulus). A baseline of zero indicates a mean sensitivity to a wire hair graded at less than 3 grams. As shown in FIG. 19A, treatment of rats (n=6/treatment) with 1 or 3 $\mu$g SNX-111 resulted in elevation of threshold response. Peak elevation of response due to drug treatment (reversal of allodynia) was observed by 30–60 minutes, and effects lasted in excess of 60 minutes. SNX-239 showed significant analgesic effects at a dose as low as 0.33 $\mu$g, and evoked a prolonged analgesic response of at least 2 hours, as indicated. SNX-159 were also effective against neuropathic pain in this test at submicromolar doses (FIG. 19C), while SNX-230 was ineffective at such doses (FIG. 19D).

Figure 19A:
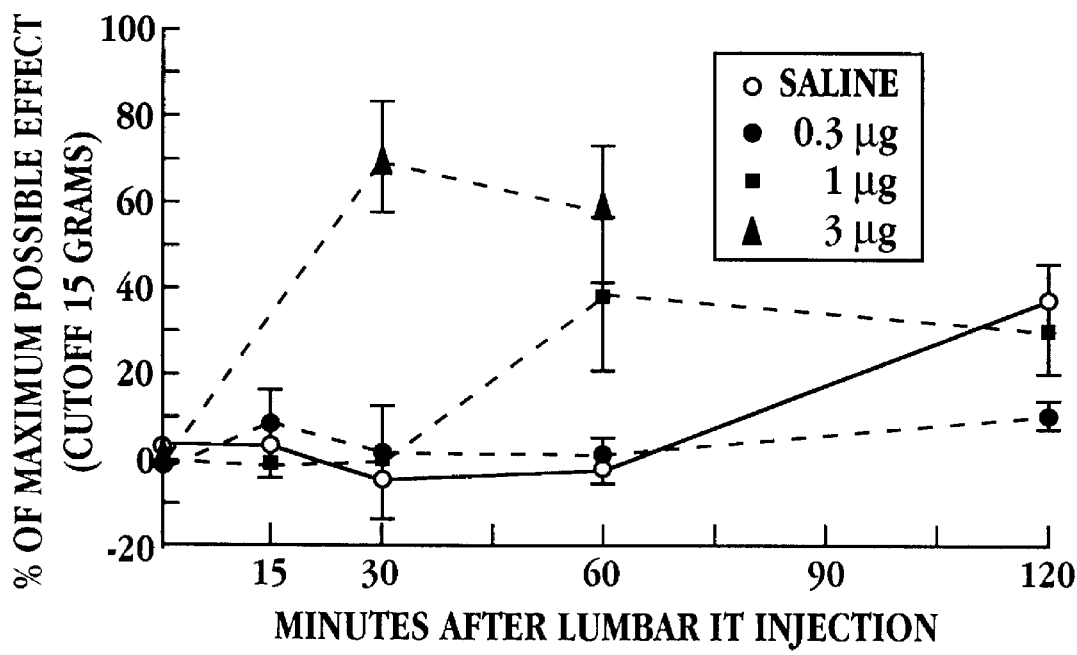
FIGS. 19(A–D) shows the effect of treatment with various omega-conopeptides on response of neuropathic rats to a wire hair as percent maximum effect, where SNX-111 (19A), SNX-239 (19B), SNX-159 (19C) and SNX-230 (19D) were tested at the doses indicated.
Figure 19B:
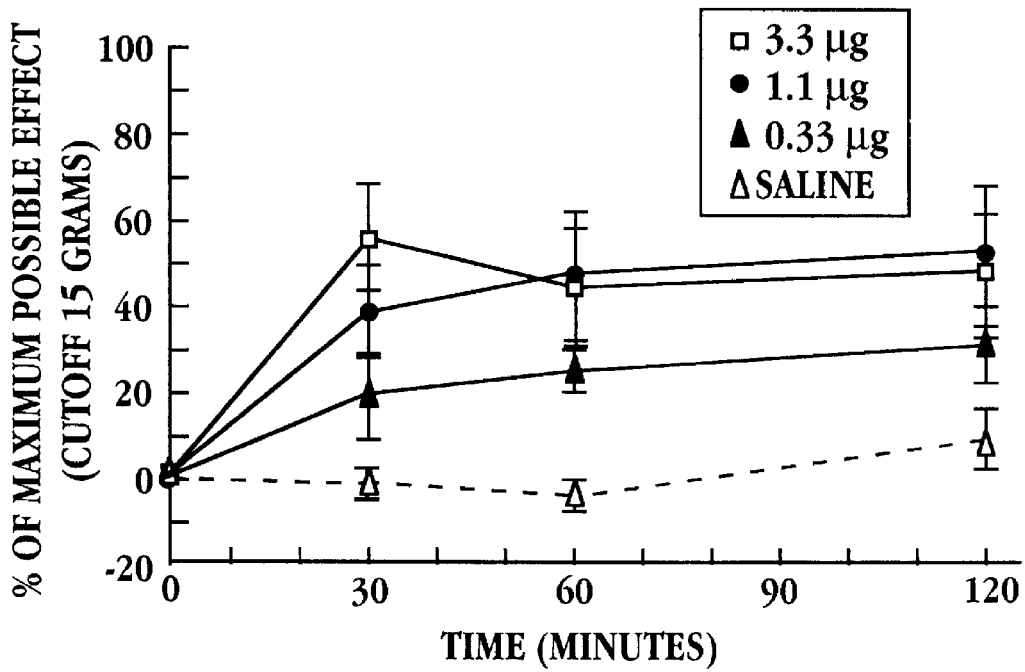
Figure 19C:
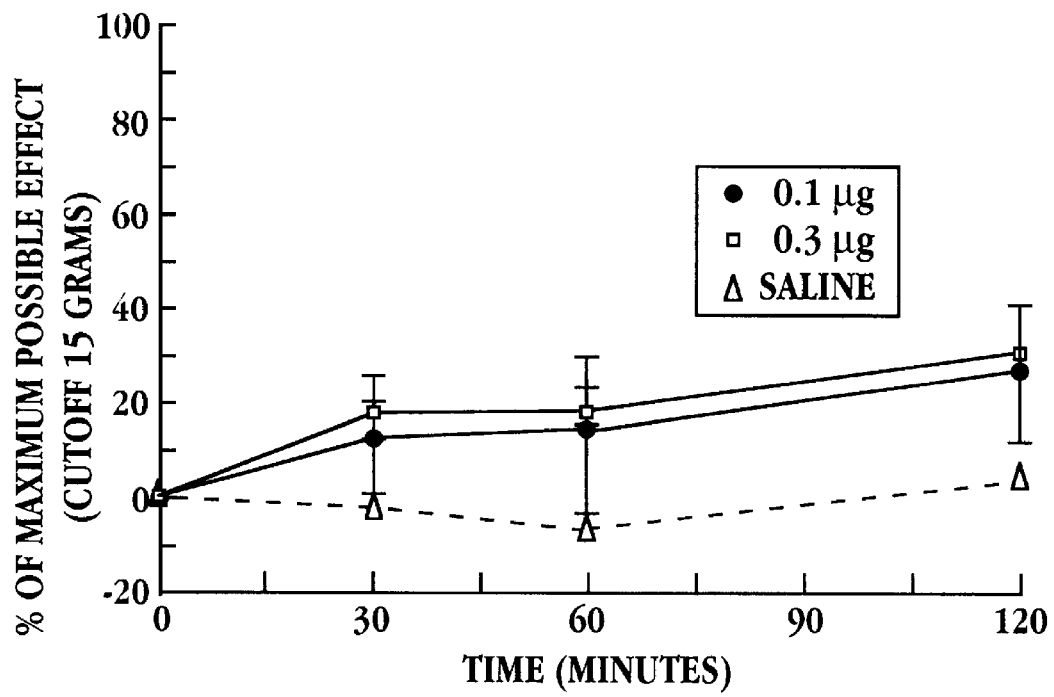
Figure 19D:
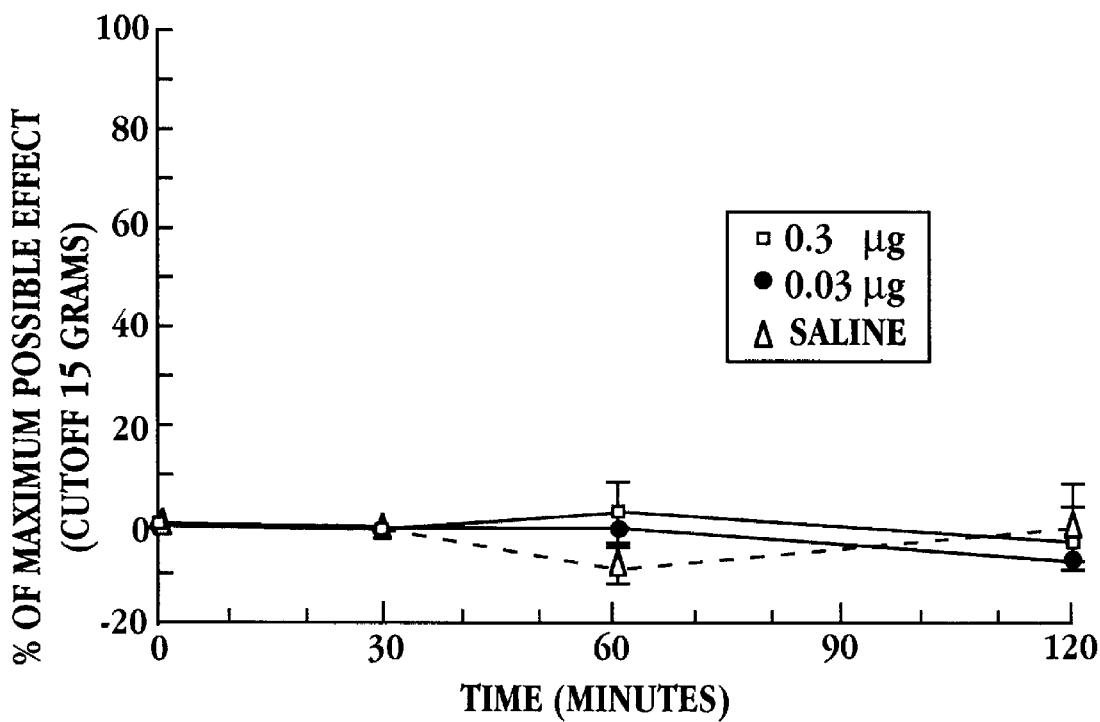
Figure 20A:
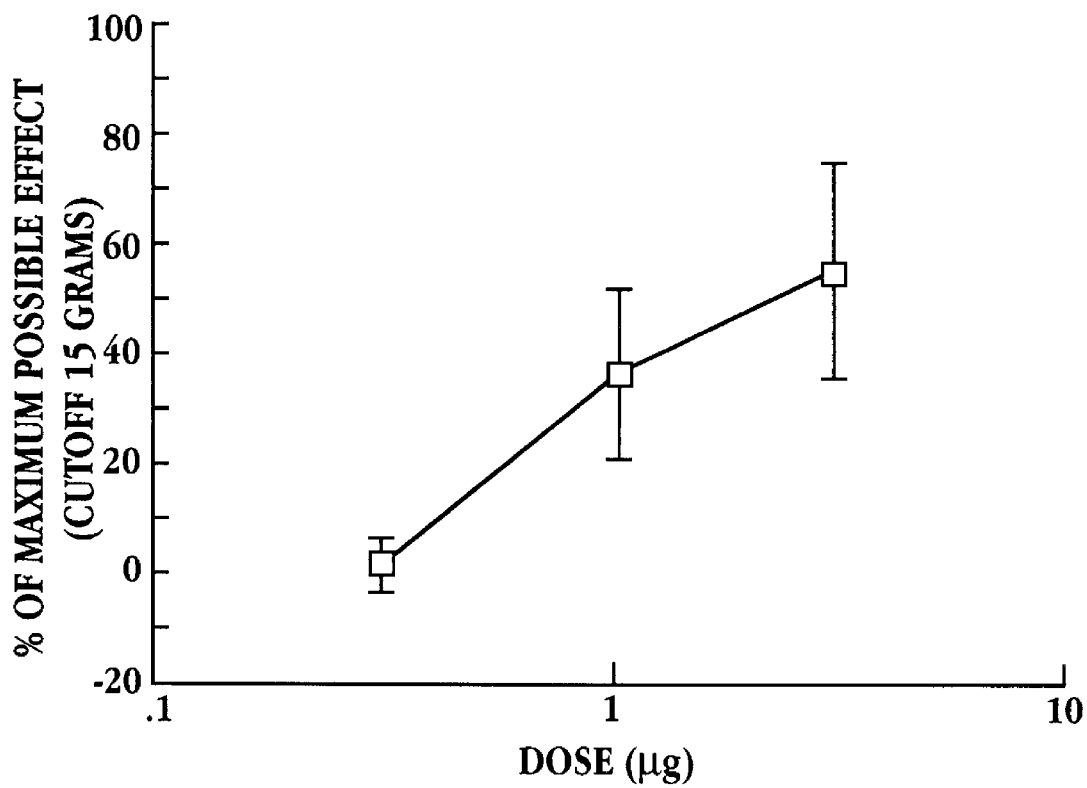
FIGS. 20(A,B) shows dose response curves of effects of omega-conopeptides SNX-111 (20A) and SNX-239 (20B) derived from the data illustrated in FIGS. 19A and 19B, respectively, in the neuropathic rat model.
Figure 20B:
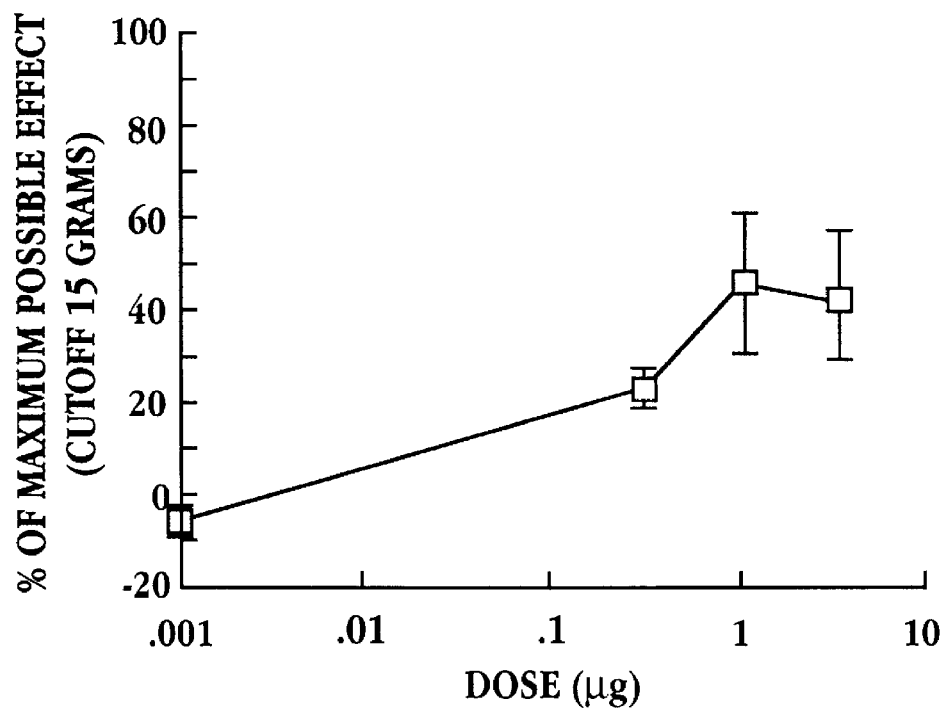

FIGS. 20A and 20B show dose response curves derived from the data shown in FIGS. 19A and 19B. These results indicate that analgesic omega conotoxin peptides, exemplified by SNX-111, are capable of reversing the hyperesthetic effects induced by nerve damage.

III. Treatment of Other Neurogenic Disorders

As indicated above, conopeptides such as MVIIA and TVIA, and their derivatives, have a number of peptide-specific binding/inhibitory activities, which include:

(1) high-affinity binding to the MVIIA binding site of neuronal cells;

(2) inhibition of norepinephrine release selectively in central nervous system neuronal cells;

(3) inhibition of voltage-gated calcium channels selectively in neuronal tissue, as evidenced by the inhibition of electrically stimulated contraction of the guinea pig ileum; and (4) inhibition (blockage) of membrane currents associated with N-type or omega HVA neuronal calcium channels is an isolated cell system, such as the mouse neuroblastoma cell line;

Previously it has been shown (co-owned U.S. Pat. No. 5,051,403) that conopeptides having defined binding/inhibitory activities are effective in reducing neuronal damage related to an ischemic condition in mammals. The binding/inhibitory activities of conopeptides effective in such treatment include:

(a) high-affinity binding to the MVIIA binding site; and
(b) selective inhibition of norepinephrine release in central nervous system neuronal cells.

Two conopeptides which have these characteristic activities, and which have been shown effective in reducing post-ischemia neuronal damage, are conopeptides MVIIA and TVIA.

In the Section above, it was shown that conopeptides, such as MVIIA and TVIA, which have defined binding/inhibitory activities, are effective in producing analgesia. The important binding/inhibitory activities are:

(a) high-affinity binding to the MVIIA binding site; and
(b) inhibition of voltage-gated calcium channels selectively in neuronal tissue, as evidenced by the inhibition of electrically stimulated contraction of the guinea pig ileum.

It is of interest, therefore, to show that conopeptides such as MVIIA, TVIA and derivatives thereof having (a) high-affinity binding to the MVIIA binding site of neuronal cells, and (b) a cell-inhibitory activity related to the inhibition of N-channel calcium currents, are also effective as therapeutic agents against other neurogenic conditions, as follows:

A. Schizophrenia

Schizophrenia is a neurogenic disorder which is currently treated primarily with compound such as phenothiazines and butyrophenones, which block dopamine receptors.

The in vitro selection criteria for omega-conopeptide useful in treating schizophrenia, include: a) blockade of voltage-gated calcium channels, b) high affinity reversible binding to an omega-conopeptide binding site localized to the limbic region of the brain, and c) inhibition of dopamine release from brain regions, particularly limbic brain regions.

Compounds showing sufficiently high activities in the above in vitro screening assays are then tested in an animal model used in screening anti-psychotic compounds, the rat striatal turning model. In the paradigm used, animals are subjected to unilateral lesion of the nigrostriatal pathway in the brain, by application of 6-hydroxydopamine to this pathway. Lesioned animals characteristically display a turning or circling behavior, with turning occurring in the direction ipsilateral to the lesioned side. Compounds useful in the treatment method of the invention, when injected locally to the striatum contralateral to the lesion, will correct the circling behavior.

B. Tardive Dyskinesia and Acute Dystonic Reactions

Tardive dyskinesia and acute dystonic reactions are movement disorders which are commonly produced as side effects of anti-psychotic therapy employing dopamine antagonists, such as haloperidol. These disorders are characterized by supersensitivity of dopamine receptors in certain regions of the brain associated with control of movement, particularly the basal ganglia. Currently, intermittent antipsychotic therapy is used in attempts to avoid onset of the disorder, and such disorders are treated by withdrawal of therapy.

Criteria for selection of an omega-conopeptide for treatment of tardive dyskinesia include: a) blockade of voltage-gated calcium channels, b) high affinity reversible binding to the OCT MVIIA peptide binding site localized to the basal ganglia, c) inhibition of dopamine release from striatal brain regions, and other regions of the basal ganglia, and d) a ratio of inhibition of dopamine release in the basal ganglia to inhibition of dopamine release in the limbic regions which is within the range of such ratio observed for SNX-111.

Compounds showing sufficiently high activities in the above in vitro screening assays are then tested in the rat striatal turning model, described above. Compounds useful in the method of treating such movement disorders, when injected to the striatum on the side of the brain contralateral to the lesion, correct the turning behavior.

C. Inflammation

A neurogenic component of inflammation has been described, in that blockade of the sympathetic nervous system, and particularly blockade of beta-adrenergic receptors, is helpful in reducing inflammatory joint damage. Compounds useful in the treatment of inflammation would be expected to have the following in vitro properties: a) blockade of voltage-gated calcium channels, b) high affinity binding to the omega-conopeptide binding sites, and c) inhibition of norepinephrine release from nervous tissue. Compounds exhibiting sufficiently high activities in such in vitro screening assays are tested in an animal model of rheumatoid arthritis, such as that described by Fitzgerald (1989).

D. Epilepsy

Epilepsy is a general term which describes disorders of the central nervous system characterized by repeated episodes of seizures. Such seizures may involve the sensory, autonomic or motor nervous systems and are recognized electrophysiologically by the presence of abnormal electric discharges in the brain. The pathophysiology of such abnormal discharge activity is not well understood; however there is evidence that loss of inhibitory neural input, such as GABA input, is involved in at least some epileptic seizures.

The ability of certain of the benzodiazepines (e.g. diazepam) to repress or inhibit epileptic episodes is considered by some to be evidence of a GABAergic pathophysiology in seizure activity, since these drugs are known to potentiate GABAergic neural inhibition via an effect on the GABA receptor-associated chloride ion channel. Biochemical effects of other anti-epileptic compounds include stabilization of excitable membranes by inhibition of voltage-sensitive sodium or potassium channels (phenytoin), and general depression of neuronal function characterized by facilitation of GABA-ergic transmission, inhibition of the effects of excitatory (glutaminergic) neurotransmission and depression of neurotransmitter release (phenobarbital).

Compounds useful in the treatment of epilepsy would be expected to have the following in vitro properties: a) blockade of voltage-gated calcium channels, b) high affinity binding to the omega-conopeptide binding sites, and c) inhibition of excitatory neurotransmitter release, such as glutamate release, from nervous tissue. Compounds exhibiting sufficiently high activities in such in vitro screening assays are tested in an animal model of epilepsy, such as the alumina cream cortical model or the genetic Mongolian gerbil model (Delgado).

The following examples are intended to illustrate various characteristics of the method of the invention, but are in no way intended to limit the scope of the invention.

EXAMPLE 1

Preparation of OCT Peptides

Abbreviations used in this example are BOC, tertiary butoxycarbonyl; DCM, dichloromethane; TFA, trifluoroacetic acid; IPM, N-isopropylmorpholine; BOC-AA-OH, BOC amino acid; DIEA, diisopropylethylamine; 2-ClZ, chlorobenzyloxycarbonyl; tosyl, p-toluenesulfonyl; DMF, N,N-dimethylformamide; TFE, trifluoroethanol; SA, symmetrical anhydride of BOC-AA-OH; DCCI, N,N-dicyclohexylcarbodiimide; E, ethyl ether; P, petroleum ether.

Commercially available benzhydrylamine-resin hydrochloride, Lot No. B30101, was obtained from commercial sources (Beckman Instruments Inc., Palo Alto, Calif.; Advanced ChemTech). With this resin, cleavage of a peptide formed on the resin, under the conditions described below, produces a peptide which is amidated at its carboxy end.

A. Preparing Protected Amino Acid Anhydrides

Each BOC-AA-OH (2.4 mmol) was dissolved in 5 ml $CH_2Cl_2$ and cooled to 0° C. The volume of DCM used for BOC-Leu-OH (dried in vacuo) was 12 ml, and the BOC-Leu-OH solution was not cooled. 2 ml 0.6M DCCI in DCM was added and the mixture stirred at 0° C. for 15 min. For BOC-Leu-OH, the mixture was also cooled after this addition. Precipitation of N,N-dicyclohexylurea was completed by storage at −20° C. for 1.5 hour, after which the precipitate was filtered and washed with ethyl ether (5 ml). The filtrate was evaporated to remove solvents and the product was crystallized in the solvent system given in the Table below. Residual amounts of DCM can affect the exact conditions for crystallization. Recrystallization was performed by dissolving in DCM, evaporating most of the solvent, and recrystallizing from the appropriate solvent.

Table of Amino acid Solvents

| Amino Acid | Solvent |
| --- | --- |
| Ala | DCM:E:P |
| Asp (Benzyl) | E:P |
| Gly | E:P |
| Leu | P |
| Lys (2-ClZ) | E:P |
| Met | E:P |
| Ser (Benzyl) | E:P |
| Thr (Benzyl) | E:P |
| Tyr (2-BrZ) | DCM:P |

B. Preparation of MVIIA

Synthesis of MVIIA peptide was performed on 0.58 g benzhydrilamine resin (0.40 mmol) in a Beckman Model 990 Peptide Synthesizer by a solid-phase method based on the primary structure shown in FIG. 1A.

A double coupling protocol was used for the incorporation of residues Cys-25 through Tyr-13, and a triple coupling protocol, for amino acids Met-12 through Cys-1. Symmetrical anhydrides were used in crystalline form as described in Yamashiro. Crystalline symmetrical anhydrides (1.0 mmole) were each dissolved in 6 ml DCM and stored in the amino acid reservoirs at 4° C. Side-chain protecting groups used were: Cys, 4-MeBenzyl; Lys, 2-ClZ; Ser, Benzyl; Arg, Tosyl; Thr, Benzyl; Asp, Benzyl; Tyr, 2-Br-Benzyl.

Unless specified, volumes were 8 ml, except for step 2 below, which was 10 ml, and all reactions were carried out at room temperature. After incorporation of the Asp-14 residue, the volume of step 2 was increased to 15 ml while all other volumes were raised to 10 ml after incorporation of the Arg-10 residue. The double coupling protocol consisted of steps 1–16 listed in the Table below.

Amino acids Met-12 through Cys-1 were added by a triple coupling protocol which included, in addition to steps 1–16, steps 17–20 in the MVIIA protocol Table.

MVIIA Protocol Table

| Step | Reagent |
| --- | --- |
| 1 | DCM wash (3 times) |
| 2 | 67% TFA/M (20 min.) |
| 3 | DCM wash (2 times) |
| 4 | 25% dioxane/DCM wash (2 times) |
| 5 | 5% DIEA/DCM wash |
| 6 | DCM wash |
| 7 | 5% DIEA/DCM wash |
| 8 | DCM wash (5 times) |
| 9 | 1.0 mmol SA in DCM (5 min) |
| 10 | 0.5 mmol IPM in 3 ml TFE plus 1 ml DCM |
| 11 | (5 min) |
| 12 | 0.5 mmol IPM in 5 ml DCM (5 min) |
| 13 | DMF wash (3 times) |
| 14 | 1.0 mmol SA in DMF (5 min) |
| 15 | 0.5 mmol IPM in 5 ml DCM (5 min) |
| 16 | 0.5 mmol IPM in 4 ml DMF (5 min) |
| 17 | DCM wash |
| 18 | DCM wash (2 times) |
| 19 | 1.0 mmol SA in DCM (5 min) |
|  | 0.5 mmol IPM in 4 ml DMF (5 min) |
| 20 | DCM Wash |

Crystalline symmetrical anhydrides (1 mmole) were each dissolved in 6 ml DCM or DMF and stored in the amino acid reservoirs at 4° C. Side-chain protecting groups used were: Cys, 4-MeBzl; Lys; ClZ; Ser, Bzl; Arg, tosyl; Thr, Bzl; Asp, Bzl; Tyr, BrZ.

For BOC-Arg(tosyl)-OH, the following mixture was prepared: 1.87 BOC-Arg(tosyl)-OH, 0.57 g 1-hydroxybenzotriazole, 15 ml DMF, stirred to dissolve, cooled to 4° C., added 0.52 ml diisopropylcarbodiimide, and split in half for steps 9 and 13. For this coupling, the protocol was modified as follows: step 8 was 3 times DCM wash and 2 times DMF wash; step 9 was for 10 min; step 11 was for 10 min; step 13 was for 10 min; step 14 was 0.4 mmol IPM in 4 ml DMF for 10 min; step 15 was for 10 min; step 16 was 1 times DMF wash and 1 time DCM wash. Reaction mixtures in steps 9, 10, 13,.14 and 18 were not drained.

The mixture for a third coupling for incorporating the Arg-10 residue consisted of 1.00 g BOC-Arg(tosyl)-OH, 1 ml DMF, 5 ml DCM, stirred to dissolve, and cooled to 4° C. to which is then added 1.67ml 0.6M DCCI in DCM.

After the last amino acid had been incorporated, the protected peptide resin was subjected to steps 1–4 to remove the N-terminal BOC group, collected on a filter with use of ethanol, and dried in vacuum to yield 2.61 g.

MVIIA has also been successfully synthesized on an ABI 430A synthesizer using slight modifications of the above protocol.

C. Deblocking and Cleavage in Liquid HF

A mixture of protected peptide resin (1.32 g), 2-mercaptopyridine (0.50 g), p-cresol (2.6 g), and liquid hydrogen fluoride (HF) (25 ml) was stirred at 0° C. for 80 min. The liquid HF was evaporated with a rapid stream of nitrogen gas, first below 0° C., then at 24° C. The mixture was stirred in ethyl acetate (25 ml) until a finely divided solid was obtained. The solid was filtered, washed with ethyl acetate, and air dried to yield 1.09 g. This solid was stirred in 50% aqueous acetic acid (10 ml) to dissolve the peptide material, filtered, and washed with 20 ml water. The filtrate was freeze-dried to yield 450 mg of fluffy powder.

D. Formation of Disulfide Bridges

A sample (300 mg) of the fluffy powder was dissolved in 30 ml of 0.05M ammonium bicarbonate, 10 mM dithiothreitol (DTT), and 2M guanidine hydrochloride. The solution, which had a pH of 6.7, was allowed to stand at 24° C. for 2 hr, then diluted with 120 ml of water and stirred for 20 hr at 24° C. DTT (25 mg) was added and the solution allowed to stand at 24° C. for 80 min. The mixture was then stirred at 4° C. for 3 days.

E. Isolation of MVIIA OCT

The solution from Part D was acidified with glacial acetic acid (2 ml), evaporated in vacuo to a low volume, and fractionated by gel filtration on Sephadex G-25 in a 2.5×48 cm column, using 1N acetic acid, to remove peptide polymeric species (exclusion volume), and salts (slowest moving peak). Fractions (5 ml) were collected, with peptide absorbance monitored at 280 nm. Fractions corresponding to the monomer peptide were pooled and freeze-dried to give 127 mg of fluffy powder. A sample of the monomeric material (34 mg) was purified by preparative HPLC on a Vydac 218TP1022 column with a gradient of 10–20% acetonitrile in 0.1% trifluoroacetic acid over 50 min at 8 ml/min, with detection at 226 nm and collection of 4 ml fractions. Fractions corresponding to the major peak were pooled, evaporated in vacuo to remove acetonitrile, and freeze-dried to yield 7.7 mg. Analytical HPLC on a Vydac 218TP104 column with the same solvent and gradient over 10 min followed by 10 min of isocratic elution at the 20% composition (1.5 ml/min) gave a single peak identical in behavior to an authentic sample of OCT MVIIA. Amino acid analysis of a 24-hr HCl-hydrolysate gave: Asp, 0.93; Thr,1.05; Ser, 2.85; half-cystine, 5.2; Gly, 4.08; Ala, 1.07; Met 0.94; Leu, 1.02; Tyr,0.85; Lys, 3.98; Arg, 2.09.

F. Radio-Iodination of MVIIA

MVIIA peptide was iodinated by reaction with Iodogen™ in the presence of NaI according to Cruz et al., with minor modification. 2 m Ci of carrier-free Na$^{125}$I, 75 ul 0.5M phosphate buffer pH 7.4 and 20 ul of 1 ug/ul peptide were added to a polypropylene test tube coated with 10 ug Iodogen™. The tube was agitated for 8 minutes, and the solution was chromatographed by HPLC through a 10×0.46 cm C-8 reverse phase column with a pore size of 300 Å (Brownlee Labs, Santa Clara, Calif.). The sample material was eluted with a gradient from 0.1% trifluoroacetic acid to 60% acetonitrile in 0.1% trifluoroacetic acid. The major peak of active radio-iodinated peptide was resolved at about 2 minutes greater retention time than the underivatized peptide.

The fractions containing this peak were collected and later diluted for use in binding experiments. MVIIA, iodinated under the conditions as above except with non-radioactive NaI, was tested for the ability to inhibit depolarization-dependent ATP release from synaptosomes as described in Ahmad and found to be as potent in this regard as the underivatized peptide.

G. Synthesis of Other OCT Peptides

Synthesis of other OCT peptides was according to the solid-phase method described in Example 1, except that a single coupling protocol involving steps 1–12 in Part C was used for coupling the first 10 C-terminal amino acids residues, and a double coupling method involving steps 1–16, Part C was used for coupling the final n⁻10 N-terminal residues, where n is 24–29. Releasing the peptide from the solid support, removing the blocking groups, and joining the disulfide bridges were carried out substantially as above, or as described in Part H, below. The peptide was separated from salts and polymeric peptide species by gel filtration on Sephadex G-25, and purified on preparative HPLC. For binding studies, each peptide can be radioiodinated essentially as above.

H. Alternate Oxidation Methods

Two alternative oxidation methods were used in the preparation of MVIIA/SNX-111.

1. The lyophilized crude linear peptide was dissolved in 3M guanidine hydrochloride and 1.2M ammonium acetate solution to yield a concentration of approximately 12 mg peptide/ml. DTT was added to a ratio of 15 mg DTT per 100 mg peptide, and the mixture was stirred at room temperature for 1 hour. The solution was diluted 6-fold with distilled water, and stirred at 4° C. for 3–5 days. The progress of peptide oxidation was monitored by HPLC. The endpoint of the oxidation process was the complete disappearance of free thiols, determined by Ellman reaction.

2. The lyophilized crude linear peptide was dissolved in 3M guanidine hydrochloride and 0.3M potassium phosphate solution to yield a concentration of approximately 12 mg peptide/ml. After addition of 40 mg cysteine and 15 mg DTT per 100 mg peptide, the pH of the solution was adjusted to 8.0–8.1 with potassium hydroxide solution. The mixture was stirred at room temperature for 1 hour. The peptide solution was diluted 6-fold with water, and stirred at 4° C. for 3–5 days. The progress of peptide oxidation was monitored by HPLC. The endpoint of the oxidation process was the complete disappearance of free thiols, determined by Ellman reaction. (Method 2 was used in the preparation of SNX-236 and SNX-239).

Following oxidation by either of the above methods, the solution was acidified with acetic acid to pH 3, and lyophilized.

EXAMPLE 2

Calcium-Channel Antagonist Activity: Inhibition of Ionic Currents

Ionic currents through calcium channels were examined in cells that were voltage-clamped by a single patch-clamp electrode. These whole-cell patch-clamp studies were performed mainly on N1E115 mouse neuroblastoma cells, although a variety of cell types, including human neuroblastoma cell line IMR-32, have been examined.

A. Current Measurement Methods

Most measurements were obtained using a bath saline that allowed examination of the calcium currents in the absence of other ionic currents. These solutions contained 80 mM NMDG (as a sodium replacement), 30 mM TEACl (to block potassium currents), 10 mM BaCl$_2$ (as a charge-carrier through the calcium channels), and 10 mM HEPES at pH 7.3. Some solutions also contained 2 mM quinidine (to block potassium currents) and 3 μM tetrodotoxin (to block sodium currents). Normal bath saline was (mM): 140 NaCl, 10 glucose, 3 KCl, 2 CaCl$_2$, 1 MgCl$_2$, 10 mM HEPES pH 7.3. Intracellular solutions contained 150 mM CsCl, 0.5 mM CaCl$_2$, 5 mM EGTA, 5 mM MgCl$_2$, 2 mM K$_2$ATP at pH 7.3–7.4. Bath saline and all internal solutions were filtered before use.

Pipets were made from Corning 7052 glass (Garner Glass Company, Claremont, Calif. 91711), coated with Sylgard (Dow Corning, Midland, Mich. 48640) and fire-polished before use. Bubble numbers were typically 5 to 6, with pipet resistances typically 2–5 MOhms. Corning 8161, Kimble, and other glasses were also used without noticeable effect on the calcium currents observed.

Recordings were carried out at room temperature with an Axopatch 1-C amplifier (Axon Instruments, Foster City, Calif. 94404) and analyzed with pCLAMP software (Axon Instruments). Data were filtered at 1000 Hz for a typical sampling rate of 0.1 kHz; in all cases data were filtered at a frequency at most ⅕ of the sampling rate to avoid biasing. Data were collected on-line by the software. Analysis was performed on-screen with print-out via a Hewlett-Packard LaserJet Printer (Hewlett-Packard, Palo Alto, Calif. 94306).

The typical experiment was conducted as follows: after seal formation followed by series resistance compensation and capacitative transient cancellation, a voltage clamp protocol was performed wherein the cell potential was stepped from the holding potential (typically –100 mV) to test potentials that ranged from –60 mV to +20 mV in 10 mV increments. The cell was held at the holding potential for 5 seconds between pulses. Protocols starting from other holding potentials usually covered the same range of test potentials.

B. Current Inhibition Measurement

FIG. 3 shows calcium current traces from an N1E-115 mouse neuroblastoma cell. The figure is read from left to right in time, with downward deflections of the trace indicating positive current flowing into the cell. Currents were elicited by a voltage step from 100 mV to –10 mV. The cell was bathed in saline with sodium replaced by NMDG and 10 mM Ba$^{++}$ instead of 2 mM Ca$^{++}$. Potassium currents were blocked by TEA in the bath and Cs$^+$ in the pipet solution.

The three traces in FIG. 3, labeled B–D, show decreasing calcium currents, with increasing MVIIA omega-conopeptide concentrations of 10 nM (3B), 50 nM (3C), and 200 nM (3D).

The response of voltage-gated calcium current to increasing dosages of OCTs MVIIA and GVIA are shown in FIG. 4. The calculated IC$_{50}$ is approximately 10 nM for GVIA and 100 nM for MVIIA. These values indicate extremely high specificity of the peptides for their site of action.

Table 1 compares IC$_{50}$ values for GVIA, MVIIA, SVIB and SVIA OCTs. Whereas OCT GVIA and OCT MVIIA show 50% inhibition of the measured calcium current at nanomolar concentration range, IC$_{50}$ values for OCT SVIB and OCT SVIA were not measurable within the range of concentrations tested, and are therefore listed as having IC$_{50}$ values above the micromolar concentrations indicated.

EXAMPLE 3

Omega-conopeptide Binding to Omega-conopeptide Binding Sites in Synaptosomal Membranes

A. Preparation of Mammalian-Brain Synaptosomes and Synaptosomal Membranes

Synaptosomes were prepared from rat whole brain or hippocampal region of brain. Rats were sacrificed, and forebrains were removed and transferred to 10 ml ice-cold 0.32M sucrose containing the following protease inhibitors (PI): 1 mM EGTA; 1 mM EDTA; 1 uM pepstatin; 2 uM leupeptin. Brains were homogenized using a motor-driven Teflon-glass homogenizer (approx. 8 passes at 400 rpm). Homogenates from 4 brains were pooled and centrifuged at 900×g for 10 minutes at 4 degrees. Supernatants were then centrifuged at 8,500×g for 15 minutes. Resulting pellets were resuspended in 10 ml each ice-cold 0.32M sucrose plus PI with vortex mixing. The suspension was then centrifuged at 8,500×g for 15 minutes. Pellets were resuspended in 20 ml ice-cold 0.32M sucrose plus PI. The suspension (5 ml/tube) was layered over a 4-step sucrose density gradient (7 ml each: 1.2M sucrose, 1.0M sucrose, 0.8M sucrose, 0.6M sucrose; all sucrose solutions containing PI). Gradient tubes were centrifuged in a swinging bucket rotor at 160,000×g for 60 minutes at 4 degrees. The 1.0M sucrose layer plus the interface between the 1.0 and 1.2M sucrose layers were collected and diluted with ice cold deionized water plus PI to yield a final sucrose concentration of 0.32M. The resulting suspension was centrifuged at 20,000×g for 15 minutes. Pellets were then resuspended in 5 ml ice-cold phosphate buffered saline plus PI. The resulting rat brain synaptosomes were then aliquoted and stored in a liquid nitrogen containment system.

Prior to use in binding assays, synaptosomes were thawed and diluted with 3 volumes of ice cold deionized water plus PI. This suspension was homogenized using a PT 10–35 Polytron (setting 6) for two 10-second bursts. The homogenate was centrifuged at 40,000×g for 20 minutes at 4 degrees. The resulting pellets were resuspended in about 5 ml of ice cold phosphate buffered saline plus PI. The resulting brain synaptosomal membrane preparation was aliquoted and stored at –80° C. until use. Protein concentration of the membrane preparation was determined using Bradford reagent (BioRad), with bovine serum albumin as standard.

B. Saturation Binding Assay

MVIIA OCT was radiolabeled with $^{125}$I-iodine by reaction with Iodogen™, essentially according to the method of Ahmad and Miljanich. Following the Iodogen reaction, the peptide solution was chromatographed by HPLC through a C-8 reversed phase column and eluted with a gradient from 0.1% trifluoroacetic acid in water to 0.1% trifluoroacetic acid in water/acetonitrile (40:60 vol/vol). The major peak of radioactivity following the underivatized MVIIA OCT was collected.

The binding constant (K$_d$) for [$^{125}$I]-MVIIA OCT to rat brain synaptosomal membranes was determined by a saturation binding method in which increasing quantities of [$^{125}$I] MVIIA OCT were added to aliquots of a synaptosomal membrane preparation (10 ug membrane protein, suspended in binding buffer consisting of 20 mM HEPES, pH 7.0, 75 mM NaCl, 0.1 mM EGTA, 0.1 MM EDTA, 2 μM leupeptin, 0.035 μg/ml aprotinin, and 0.1% bovine serum albumin (BSA), in a total volume of 0.5 ml). Binding at each concentration of labeled compound was determined in the absence and presence of 1 nM unlabeled MVIIA OCT to determine specific binding (as described in part B, below). The amount of labeled peptide specifically bound at each concentration was used to determine B$_{max}$, the concentration of specific binding sites on the synaptosomes, and K$_d$, following standard binding analysis methods (Bennett). FIG. 6A shows a saturation binding curve of [$^{125}$I]MVIIA to rat synaptosomal membranes. FIG. 6B shows a Scatchard transformation of the data, from which a calculated K$_d$ of about 10 pM is determined.

B. Reversibility of Binding

Rat brain synaptosomal membranes were incubated with a concentration of radiolabeled ligand approximating the $K_d$ of the ligand for its binding site, for a period of time sufficient to achieve equilibrium binding. A high concentration of unlabeled ligand was then added to the mixture, and the incubation continued. At time intervals, samples of the mixture were tested for binding of radiolabeled compound. As shown in FIG. 7, SNX-111 exhibited reversible binding with a dissociation half-time of about 2 min. Likewise, SNX-183 binding exhibited reversible binding with a dissociation half-time of about 5 min. In contrast, radiolabeled SNX-124 showed no dissociation from its binding site over the time period studied (60 min).

C. Competitive Displacement Binding Assay

1. Competitive Displacement of OCT MVIIA

Rat brain synaptosomal membranes prepared as described in Part A were suspended in a binding buffer consisting of 20 mM HEPES, pH 7.0, 75 mM NaCl, 0.1 mM EGTA, 0.1 mM EDTA, 2 $\mu$M leupeptin, 0.035 $\mu$g/ml aprotinin, and 0.1% bovine serum albumin (BSA). [$^{125}$I]-MVIIA (SNX-111) OCT (25–30,000 cpm, approximately 1500–2000 Ci/mmol) and test compound were aliquoted into polypropylene tubes, in the absence or presence of 1 nM MVIIA (SNX-111) OCT to determine non-specific binding. The membrane suspension was diluted and aliquoted last into the test tubes, such that each assay tube contained 10 $\mu$g membrane protein and the total volume was 0.5 ml. After incubation for 1 hour at room temperature, tubes were placed in an ice bath, then filtered through GF/C filters (Whatman), which were pre-soaked in 0.6% polyethyleneimine and prewashed with wash buffer (20 mM HEPES, pH 7.0, 125 mM NaCl, 0.1% BSA) using a Millipore filtration system. Just prior to filtration, each assay tube received 3 ml ice-cold wash buffer. The filtered membranes were washed with two 3 ml volumes of ice-cold wash buffer, dried, and filter-bound radioactivity was measured in a Beckman gamma counter (75% counting efficiency).

Representative displacement binding curves for rat brain synaptosomal membranes are illustrated in FIG. 8. $IC_{50}$ values were computed from line fit curves generated by a 4-parameter logistic function. These values represent the concentration of test compound required to inhibit by 50% the total specific binding of [$^{125}$I]-MVIIA (SNX-111) OCT to rat brain synaptosomal membranes, where specific binding is defined as the difference between binding of [$^{125}$I]-MVIIA (SNX-111) OCT in the absence and presence of excess (1 nM) unlabelled MVIIA OCT. Non-specific binding is that binding of radiolabeled compound which is measured in the presence of excess unlabeled MVIIA OCT. Such values serve as approximations of the relative affinities of a series of compounds for a specific binding site.

2. Competitive Displacement of OCT SVIB

Rat brain synaptosomal membranes were prepared as described in Example 3. OCT SVIB was radiolabeled by iodination with $^{125}$I-iodine by the Iodogen reaction, described in Example 4. Displacement binding of radiolabeled SVIB on rat brain synaptosomal membranes was carried out as in Example 4B. SVIB displacement curves for several of the omega-conopeptides assayed is shown in FIG. 9. $IC_{50}$ values and relative potency values were calculated as described below. Table 4 shows the relative potency values for omega-conopeptides examined, and the ratio of relative potencies of the compounds for the OCT MVIIA site and to the SVIB binding site.

The binding constant ($K_i$) for each test substance was calculated using non-linear, least-squares regression analysis (Bennett & Yamamura) of competitive binding data from 2 assays performed in duplicate on separate occasions. The relationship between $K_i$ and $IC_{50}$ (concentration at which 50% of labeled compound is displaced by test compound is expressed by the Cheng-Prusoff equation:

$$K_i = IC_{50}/(1+[L]/K_d)$$

where $IC_{50}$ is the concentration of test substance required to reduce specific binding of labeled ligand by 50%; [L] is the concentration of [$^{125}$I]-MVIIA (SNX-111) OCT used in the experiment; and $K_d$ is the binding constant determined for binding of [$^{125}$I]-MVIIA (SNX-111) OCT to rat brain synaptosomal membranes in saturation binding experiments. Table 3 summarizes computed $IC_{50}$ for various omega-conopeptides for the MVIIA binding site of rat brain-synaptosomal membranes.

Relative potency for displacement of binding is calculated as a ratio of the $IC_{50}$ of the test compound and the $IC_{50}$ of the reference compound. The reference compound is generally the unlabeled equivalent of the labeled ligand. Calculation of relative potency is as follows:

$$[\log (\text{relative potency})] = \log (IC_{50(ref)}) - \log (IC_{50(test)})$$

Relative potency values for binding at OCT MVIIA (SNX-111) and OCT SVIB (SNX-183) sites are listed in Table 3.

EXAMPLE 4

Crosslinking of [$^{125}$I]-SNX-111 and [$^{125}$I]-SNX-183 to Their Polypeptide Receptors

A. SDS-Gel Electrophoretic Analysis of Rat Hippocampal Synaptosomal Membrane Polypeptides Chemically Crosslinked with A

[$^{125}$I]-SNX-111 and B. [$^{125}$I]-SNX-183. Both radioactive ligands (1 nM) were incubated with rat hippocampal synaptosomal membranes in the absence (middle lanes) or presence (right lanes) of excess non-radioactive peptide at 1000 times the IC50 for binding (i.e., 10 nM for SNX-111 and 1 mM for SNX-183) and crosslinking was achieved by the addition of N-hydroxysuccinimide (NHS) and the water-soluble carbodiimide, EDC (45). The left lanes are controls to which EDC and NHS were not added.

B. Displacement of crosslinked [$^{125}$I]-SNX-183 by SNX-111

[$^{125}$I]-SNX-111 (A) or [$^{125}$I]-SNX-183 (B) crosslinked to the 210 kDa polypeptide(s) in rat hippocampal synaptosomal membranes were displaced by increasing concentrations of non-radioactive SNX-111 and SNX-183 (45). As expected, the site 1-specific ligand [$^{125}$I]-SNX-111 was displaced monotonically by both SNX-111 and SNX-183. In contrast, displacement of [$^{125}$I]-SNX-183 by SNX-111 is biphasic with IC50's similar to its IC50's for binding to site 1 and site 2. The amount of radioiodinated peptide incorporated into the 210 kDa band of crosslinked hippocampal synaptosomal membranes exposed to varying concentrations of competing peptides was estimated by scanning densitometry. The optical density of the 210 kDa band in the sample without added competing peptide was taken as 100%. Curves were fit to the data as described above.

EXAMPLE 5

Localization of OCT Binding Sites in Neuronal Tissue by Receptor Autoradiography Adult male (Fischer or Sprague-Dawley, 250–300 g) were euthanized with carbon-dioxide, and whole brains were dissected out of the skull and rapidly frozen in iso-pentane pre-cooled on frozen carbon dioxide. The frozen brains were stored at −80° C. and used within a week.

Coronal sections (20μ thick) were obtained by slicing (at −10° C.–15° C.) through the frozen brain using a cryostat microtome. The sections were thaw-transferred onto glass slides precoated with gelatin. Glass slides with the frozen sections were stored at −80° C. and used within a week. Binding of [$^{125}$I] MVIIA was performed at room temperature. Each brain section was incubated for 40 min. with 250 μl of binding buffer: (HEPES/NaOH (20 mM, pH 7.5), EDTA (0.1 mM), EDTA (0.1 mm) leupeptin (2 μM), Aprotinin (0.63 mg/ml), 1.5% BSA (RIA Grade), and [$^{125}$I] MVIIA (100–150 pM). To determine the proportion of non-specific binding selected adjacent brain sections were incubated with an excess of unlabelled peptide (25 nm).

After the incubation, binding buffer was carefully poured onto blotting paper and the slides transferred to a glass slide holder. Unbound [$^{125}$I] MVIIA was washed away by serially passing the slides through four dishes of washing buffer at room temperature for a total washing time of 16 min. Washing buffer contained HEPES/NaCH (50 m19, pH 7.5), NaCl (170 mM), BSA (RIA grade lg/L) and Triton X-100 (0.05%). After the final wash, the slides were dipped quickly five times in water and dried with a blow-dryer.

Dried slides were exposed to XAR-2 film, overnight at room temperature and developed. The developed images were examined wither directly or by computer assisted image analyzer. The assignment of binding to specific neuroanatomical sites was made using an anatomical atlas of rat brain (Paxinos).

Autoradiograms show the distributions of [$^{125}$I]-SNX-111 (A,B,C,D) and [$^{125}$I]-SNX-183 (E,F,G,H) binding to coronal rat brain sections. Labeling in the presence of excess non-radioactive SNX-111 (C,D) or SNX-183 (G,H) shows that non-specific labeling is negligible. Rostral sections (A,C,E,G) and caudal sections (B,D,F,H) are each adjacent or near-adjacent. "CA" indicates the $CA_3$ region of the hippocampus and "SN" indicates the substantia nigra.

EXAMPLE 6

Inhibition of Neurotransmitter Release

A. Inhibition of Norepinephrine Release

Inhibitory constants (IC50's) reflecting the potency of SNX-111 and SNX-183, for blocking the K$^+$-evoked release of exogenous, loaded [$^3$H]-norepinephrine from rat hippocampal slices were determined. Freshly dissected hippocampal slices in oxygenated buffered saline were loaded with [$^3$H]-norepinephrine and washed three times. Slices were then exposed to buffered saline (containing 3.3 mM K$^+$) for 1.5 minutes and the supernatants containing released basal norepinephrine were collected for scintillation counting. The slices were then depolarized by exposure to buffered saline containing 30 mM K$^+$ for 1.5 minutes and the supernatants, containing evoked norepinephrine, were also collected for scintillation counting. Slices were exposed to the desired concentration of peptide in all solutions from the time of loading with norepinephrine to the end of the experiment (about 2 hours). The data points are the differences of the means of 7 basal determinations and 7 evoked determinations at each drug concentration. Release in the absence of drug is taken as 100 per cent and the remaining points are scaled accordingly. The error bars are the standard errors of the means of the differences. Curves of best fit and the corresponding IC50's were derived. The single IC50 for SNX-111 is correlated with binding to site 1 calcium channels; the two IC50s for SNX-230 are for inhibition associated with binding to site 1 calcium channels (65 nM) and to site 2 calcium channels (0.02 nM); the apparent single IC50 for SNX-183 is presumed to reflect binding to both site 1 and site 2 calcium channels with about equal affinity (see text). Evoked release in the absence of Ca$^{++}$ in the buffer was equal to basal release (data not shown); thus all release shown is calcium-dependent release.

B. Inhibition of Dopamine Release from Rat Striatal Slices

Slices (0.3×0.3×1.5 mm) were prepared from rat striatum, and were pre-loaded with radiolabeled (tritiated) dopamine. Slices were perfused for 45 minutes in Krebs Ringer Bicarbonate buffer (oxygenated) as bathing medium. Release of neurotransmitter was stimulated by adding to the perfusion medium KCl at a concentration ranging between 4.8 and 15 mM, for a period of one minute. The first such exposure was termed S1. Perfusion with bathing medium was continued. Test compound(s) were introduced into the perfusion medium 20 minutes before the second stimulation (S2), which was done identically to Si. The ratio of S2/S1 was calculated to determine drug effects. A drug was considered to block release if S2/S1 was significantly less than unity.

C. Inhibition of Acetylcholine Release from Striatal Slices

Release of acetylcholine was measured as described above in part C for dopamine release, except that slices were pre-loaded with radiolabelled choline instead of dopamine.

D. Inhibition of Electrically Stimulated Contractions of Guinea Pig Ileum

Guinea pigs (300–400 gms) were decapitated and the ileum removed. A section of ileum about 6 cm from the caecum was placed immediately into Krebb's modified buffer maintained at 37° C. in a water bath, and aerated with a mixture of 95% $O_2$ and 5% $CO_2$. The buffer contains: KCl, 4.6 mM; $KH_2PO_4$, 1.2 mM; $MgSO_4$, 1.2 mM; Glucose, 10.0 mM; NaCl 118.2 mM; $NaHCO_3$, 24.8 mM; $CaCl_2$, 2.5 mM.

Small pieces of ileum were cut and pulled over a glass pipette, scored and the longitudinal muscle removed. Each piece was attached to an electrode at one end and to a force transducer at the other end. The preparation was lowered into an organ bath maintained at 37° C. and aerated with $O_2$:$CO_2$. The resting tension was set at 1 gm, and the tissue was stimulated at 30–50V with a duration of 4.5 msec per stimulation.

Baseline responses (contractions) were recorded for 10–15 min. and aliquots (100 ml) of drug were added to the bath until inhibition occurred. Following testing, tissues were washed until original response magnitude was achieved.

E. Microdialysis Measurement of Release of Central Amino Acid Neurotransmitters

1. Microdialysis

Adult male Fisher rats of 280–320 g body weight (Simonsen Labs) were used for these studies. In vivo dialysis experiments were performed in acutely anesthetized animals. Rats were injected intraperitoneally with 0.5 mg/kg atropine sulfate and 0.65 mg/kg sodium pentobarbital, followed by sodium pentobarbital as needed.

The CMA-10 microdialysis probes provided by Carnegie Medicin were used for sampling of the extracellular space. Probes of 2 mm length were used. Probes were stereotaxically implanted, vertically and in the center of the dorsal hippocampus. For placement in the hippocampus, coordinates from Bregma were; anterior-posterior, −3.3 mm, lateral 1.7 mm, and 4.4 mm depth. For placement of probes in the thalamus, the lateral and anterior-posterior coordinates were the same and the depth coordinate was 7.0 mm. Histology verified that probes were placed in the anticipated area.

In vitro dialysis experiments showed that, were probes were placed in a solution containing glutamine, much of this glutamine was recovered as glutamate in the dialysate. This effect was minimized by perfusing probes with nitric acid/water 1/1 for 10–30 minutes, followed by extensive washing with water and saline.

After implantation, probes were perfused at a flow rate of 2 ul per minute with saline containing 125 mM sodium chloride, and 1.0 mM magnesium chloride and 3 mM sodium N-(2-hydroxyethyl)piperazine-N'-(2-ethanesulfonic acid), pH 7.4. When increased concentrations of potassium or magnesium were infused, the ions were substituted for sodium. A 90-minute equilibration period was allowed before beginning experimental protocols.

A Carnegie Medicin CMA/100 syringe pump was used for dialysate perfusion. Solutions were manually switched using a Carnegie Medicin model CMA/110 value, or automatically with a Valco model E10 valve. In the latter case, solution switches were time programmed with the Valco series valve interface using an IBM personal computer. Fractions of 20 ul (10 min) were collected over a 30 ul of dimethylformamide: water, 1:3 using a Gilson model 212b liquid handler.

2. Peptide Delivery to and Stability in the Extracellular Fluid

To determine peptide stability in the extracellular fluid, radioiodinated SNX-111 and SNX-230 were perfused for a period of 2 hours through probes implanted in the hippocampus. Unlabeled peptide (2.7 uM) was co-perfused with the radioiodinated derivative. At the end of the infusion period, the animal was sacrificed and the brain was separated down the midline. Both sides of the brain were homogenized in 10 ml of acetone/water/hydrochloric acid (40/6/1 (v/v/v) containing 1 mg/ml ascorbic acid. As controls, radioiodinated SNX-111 and SNX-230 were added to extracts of the side of the brain contralateral to the probe. An excess of sodium acetate (to hydrochloric acid) was then added, the extracts centrifuged, and supernatants extracted with an excess of diethylether. The ether saturated aqueous extracts were passed over octadecylsilica extraction cartridges ("sep-paks", Waters, Inc., Milford, Mass.). In all cases, between 60 and 80% of the radioactivity eluted in the aqueous extract passed over the solid phase extraction cartridge, and negligible material could be subsequently eluted with 60% methanol in water containing 0.1% trifluoroacetate.

The aqueous eluant from the sep-paks contained the intact conopeptides, and (after removal of residual organic solvents with a stream of nitrogen) these samples were further fractionated by gradient elution from octadecylsilica. Chromatography was over a 4.5×250 mm wide pore octadecyl-silica column (Vydac TP), 10 um particle diameter), with a 3×30 mm guard column filled with the same packing material (10–15 um particle diameter). A gradient of 1% min of methanol in 0.1% trifluoroacetic acid (started at the same time as sample injection) was used to fractionate the extracts (1–2 ml injection volume).

For determination of peptide diffusion in the extracellular space, the protocol described by Dykstra, et al. (1992) was followed. Radioiodinated SNX-111 was perfused for 2.5 hours through a probe implanted in the hippocampus, with 8 or 270 uM unlabeled peptide added as carrier. After perfusion, the head was frozen in liquid nitrogen. Sections perpendicular to the probe (40 um) were processed for autoradiography, and film density was quantitated by computerized image analysis. The radioactivity in each section was also quantitated by gamma counting.

In order to examine possible selective permeability through dialysis probes, the iodinated derivatives of SNX-111 and SNX-183 were perfused for 1 hour through the same probes placed in eppendorf tubes. The recovery in the bath external to the probe for SNX-111 was $1.3 \pm 0.61\%$ standard deviation (n=3), and for SNX-183 the mean recovery was $1.3 \pm 0.56\%$ (n=3). When iodinated peptides were perfused (for 2 or 2.5 hours) through probes implanted in vivo, the amount of radioactivity recovered in the brain was $1.1 \pm 0.53\%$ of the total perfused (n=6 experiments pooled for SNX-111 and SNX-230). Iodinated peptides were not lost to the microdialysis apparatus, as judged by a comparison of peptide concentrations in syringes and collected fractions.

3. Amino Acid Analysis

Amino acids were determined with the o-phthaldialdehyde procedure as previously described (Newcomb, 1983), but with the following modifications. The reagent was made by mixing about 100 mg o-phthaldialdehyde (Sigma Chemical Co., St. Louis, Mo.), 500 ul ethanethiol (Fluka), and 30 ml 0.5M sodium borate, pH 10.0–10.2. Elution used an aqueous buffer made by mixing 16.0 g of sodium dihydrogen phosphate, and 2.1 g of disodium hydrogen phosphate in four liters of water (pH 5.1–5.2). Methanol was used for elution, and acetonitrile was added as needed to effect resolution of GABA from ammonia. Baseline resolution of aspartate, glutamate, asparagine, histidine, glutamine, serine, arginine, PEA, taurine, alanine, and GABA was achieved. Detection was by a Gilson (Middleton, Wash.) model 121 or a Hewlett-Packard (Palo Alto, Calif.) model 1046A fluorescence detector.

4. Quantitative Analysis of Peptide Effects on Release

Amounts of eight amino acids (glutamate, asparagine, glutamine, serine, Pea, taurine, alanine and GABA) in dialysates were determined and were found to be similar to previously reported values for rat brain (Lehman, 1989). Dialysate concentrations of serine were unchanged with the potassium stimulus in the present studies, in accordance with previously published results (Westerink, et al., 1987).

For the analysis of release in response to potassium stimulation, pulses of 4 to 6 minutes of 100 mM potassium were perfused through probes at 30 minute intervals (the time differences were related to the timing of stimulus and fraction collection periods; run down of release did not change with minor differences in the stimulation protocol). The ratios of individual amino acids to serine were first calculated. The amount of release was defined as the increase over the basal level of this ratio. Release in successive potassium pulses was normalized to (divided by) that in the first potassium pulse. The extent of effects of probe infused agents was quantified as (Sn/S1)treated/ (Sn/S1) control, where S1 is the ratio to serine minus basal in the first pulse and Sn is the value for the nth pulse, where control values were determined in experiments in which potassium was administered and amino acids were quantitated in the absence of test compounds.

In experiments in which test compounds were applied, the first three stimuli contained no test compound. The values for S3/S1 in the experimental populations were compared to those in the control populations. In all experiments, there were no significant differences between the two data sets (t-test, p>0.1). Peptides were applied in the perfusion saline at 1 or 2 concentrations over 1 or 2 sets of 3–4 subsequent stimuli. When two peptide concentrations were tested in one experiment, the initial concentration was normally 5–10 fold lower than the second concentration applied. For each peptide concentration in each experiment, the mean value of the fraction of the control release was calculated for 2–4 pooled stimuli. For tests of the statistical significance of peptide effects, the ratio to the mean control release with peptide applied was compared to that obtained in the second and third stimuli of the same experiments.

Results of experiments in which conopeptides SNX-230, SNX-183, and SNX-111 were tested at varying concentrations for effects on potassium stimulated release of glutamate and GABA from the hippocampus, as described above, are summarized in FIG. 13B and FIG. 13C. A concentration dependent inhibition of release of both glutamate and GABA was observed for SNX-230 and SNX-183. SNX-111 was inhibitory only at much higher concentrations.

EXAMPLE 7

Rat Tail-Flick Assay for Analgesia

Male Sprague-Dawley rats (250–300g; Simonsen) were implanted with intrathecal (i.t.) catheters, which were inserted through the atlanto-occipital membrane and threaded subdurally about 8 cm therefrom. Animals were not used in experiments until at least 2 days following implantation.

To perform the Tail-Flick test, a rat was restrained in a plastic cone having openings at each end, and was placed on a platform, positioned such that its tail hung down from the platform in close proximity to a heating bulb. Latency to flick the tail away from the bulb was recorded. A trial consisted of four such flicks at 1–2 min. intervals, where the first latency time was generally not used, and the three subsequent tests were averaged. Latencies measured in the absence of analgesic agent(s) were recorded for each rat as "Baseline latency."

Rats were then removed from the restraining cones, and injected (i.t.) with test compound in a volume of 5 $\mu$l, followed by 10 $\mu$l saline. Animals were subjected to post-drug trials at one or more time intervals thereafter (usually 25 min and 45 min.), as described above. In the cases where drug enhancement was tested, test compound was first injected, followed by tail-flick trials, to assess the potency of the drug alone. Approximately 1 hour later, a known analgesic, such as morphine, was injected, and trials repeated.

Drug effects were calculated as follows:

$$\% \text{ Effect} = 100 \times \frac{\text{(post-drug latency)} - \text{(baseline latency)}}{\text{(maximum latency)} - \text{(baseline latency)}}$$

where maximum latency was measured as experimental cut-off time, the time beyond which the tail was not allowed by the experimenter to be exposed to heat, due to risk of burn to the animal.

EXAMPLE 8

Rat Formalin Test for Analgesia

Rats (male Sprague-Dawley, 275–300 g, Harlan Industries, Indianapolis, Ind.) were implanted with lumbar intrathecal catheters under halothane anesthesia (Yaksch and Rudy). Catheters (Polyethylene PE-10) extended from the cisterna to the rostral edge of the lumbar enlargement. 3–5 days after implant, animals without motor dysfunction were tested. Drugs tested in this assay were dissolved in sterile saline (0.9% NaCl) and injected in a volume of 10 ul followed by 10 ul sterile saline to clear the catheter.

Animals were examined for the effects of drugs given in the formalin test, in which 50 ul of 5% formalin was injected on the plantar surface of the paw of a lightly anesthetized (halothane, 3%) animal. The number of spontaneous flinching/shaking of the injected paw were counted at intervals after the injection of the formalin. Counts were made for one minute periods, the first time points beginning 2–3 minutes and 5–6 minutes post-injection. Counts were then taken at 5 minute intervals from 10–60 minutes post injection.

Injection of formalin alone or with vehicle (saline) resulted in a biphasic response pattern of hind paw withdrawals (see, for example, FIG. 16). The area under the curve of the flinches/min was calculated for phase 1 (time= 0–10 min) and phase 2 (10–60 min). These values were plotted versus the intrathecal log dose (ug) and the results are shown in FIGS. 17A and 17B.

Dose-response curves were generated using values calculated as percent of the maximum possible inhibition (maximal suppression of the formalin response=100%). The sum of flinches for the observation periods, i.e., the mean total number of flinches for phase 1 (0–9 minutes) and phase 2 (10–60 minutes), respectively, are determined for each control group (i.e., animals receiving intrathecal saline). This is defined as the effects$_{group}$ in that control group. The % of the maximum possible inhibition (% MPI) for each drug treated rat is then calculated by the formula:

$$\% \text{ MPI} = \frac{[\text{Maximum effect}_{group}] - [\text{Maximum effect drug treated rat}]}{\text{Maximum effect in effect}_{group}} \times 100$$

Figure 17A:
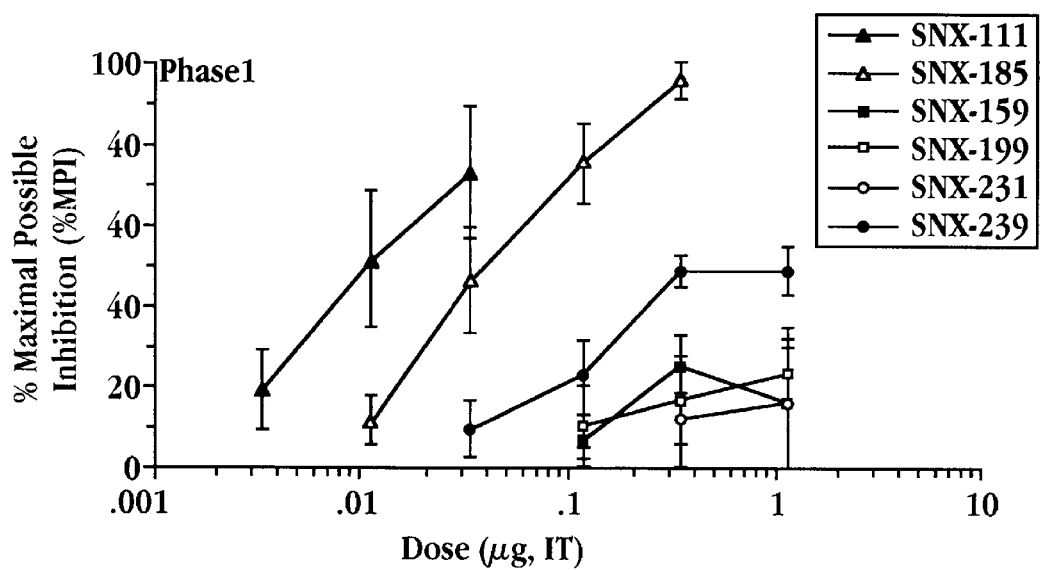
FIGS. 17A and 17B show log dose response curves for effects of SNX-111, SNX-185, SNX-159, SNX-199, SNX-231 and SNX-239 on phase 1(A) and phase 2(B) of the formalin test.
Figure 17B:
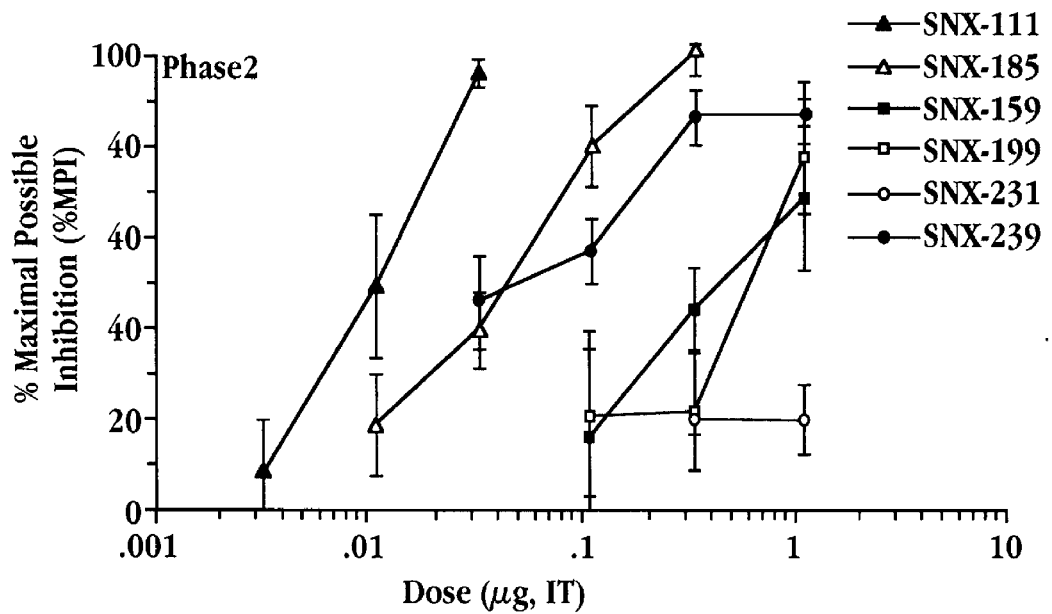

This value calculated for each rat was then used to construct drug group dose-response curves, shown in FIG. 17A for Phase 1 responses and FIG. 17B for Phase 2 responses. The dose-response lines were fitted using a least square linear regression. ED50 (effective dose resulting in a 50% reduction of the control formalin response) and 95% confidence intervals were calculated according to formulae given by Tallarida and Murray (1987).

Motor function was reflexed by the placing/stepping reflex, where a normal behavior is a stepping reflex when the hindpaws are drawn across the edge of a table. Righting and ambulation were assessed by placing the rat horizontally with its back on the table with normally gives rise to an immediate coordinated twisting of the body to an upright position. Catalepsy (spontaneous mobility) was tested by placing the forepaws on a horizontal bar kept at 4 cm from a table surface. Failure to move from the bar within 30 seconds was defined as a positive cataleptic response.

EXAMPLE 9

Rat Model of Peripheral Neuropathy

Male Sprague-Dawley rats (200–350 gm) were prepared with chronic lumbar intrathecal catheters inserted under halothane anesthesia (Yaksh and Rudy). Animals were placed in a prone position and the left paraspinal muscles were separated from the spinous processes at the $L_4$–$S_2$ levels, as described by Kim et al. The left L5 and L6 nerve roots were exposed and tightly ligated with 6-0 surgical silk suture. The rats were allowed to recover from anesthesia. Allodynia was typically observed to occur beginning 1–2 days post-surgery and continuing for as long as 45 days.

For testing, animals were placed in plastic cubicles with open wire mesh bottoms. Compound dissolved in preservative-free saline solution was administered in a volume of 10 μl through the intrathecal catheter, followed by 10 μl saline to flush the catheter line. Animals were tested for allodynia at various time points after drug treatment, as described below.

To assess the threshold of a non-noxious stimulus required to produce a left hind paw withdrawal (allodynia), Von Frey hairs (ranging from 0.4–15 grams), were systematically applied to the surgically treated hind paw. Failure to evoke a response was cause to test the next stiffer hair. Evocation of a brisk withdrawal response was cause to test the next lower stimulus intensity. This paradigm was repeated according to a statistical method (Dixon) to define the 50% response threshold. Allodynia was evidenced by a threshold less than 3 grams (referring to the hair stimulus intensity) exhibited by all surgically treated animals.

Results of animals treated with saline, or various doses of omega-conopeptides are shown in FIGS. 19 and 20. Data in FIG. 19 are expressed as percent maximum effect, where the maximum effect indicates a complete reversal of allodynia, or insensitivity to stimulus (maximum equals 15 gram hair cutoff). A baseline of zero indicates a mean sensitivity less than 3 grams. As shown in FIG. 17, treatment of rats (n=6/treatment) with 1 or 3 μg SNX-111 resulted in elevation of threshold response. Peak effects were observed by 30–60 minutes, and effects lasted in excess of 60 minutes.

Animals were also observed for the appearance of general motor dysfunction, as evidenced by inability to ambulate symmetrically and for any other overt signs of unusual activity. No effects on motor activity were observed in saline-treated animals; a dose-dependent tremor characteristic of SNX-111 administration was observed in animals given SNX-11.

EXAMPLE 10

Measurement of Sympatholytic Activity

Male Sprague-Dawley rats were anesthetized with sodium pentobarbital (60 mg/kg, i.v.). The right carotid artery, jugular vein, and trachea were cannulated. Arterial blood pressure was recorded continuously from the right common carotid artery via a pressure transducer on a polygraph (Grass model 79D). The venous line was used for drug injections, delivered in a volume of 1 ml/kg. Atropine (1 mg/kg, i.v.) was administered to eliminate vagal or sacral stimulation effects. Rats were ventilated with room air via tracheal cannula attached to a rodent respirator (CWE, model SAR-830) at a frequency of 50 strokes per minute with a tidal volume of 1.5 ml/100 g body weight. Core temperature was maintained with a warming pad.

The anesthetized rats were pithed by inserting a 2 mm diameter stainless rod through the orbit into the spinal canal. Gallamine (10 mg/kg, i.v.) was administered. The spinal cord was stimulated using the pithing rod as a positive electrode and a stainless steel needle placed subcutaneously as the indifferent electrode. Electrical stimulation was delivered via a Grass S44 stimulator. A 15 minute stabilization period was observed prior to further manipulations. Vehicle or test compound was administered through the venous line. Ten minutes following administration, the sympathetic outflow was stimulated using a 5 Hz, 50 V, 1 msec pulse (15 sec duration) given through the spinal cord stimulator. Blood pressure was monitored and recorded continuously.

Although the invention has been described with respect to particular embodiments, it will be apparent to those skilled that various changes and modifications can be made without departing from the invention.

---

It is claimed:

1. A method of treating inflammation in a subject, in need of said treatment comprising
administering to the subject a pharmacologically effective dose of an omega-conopeptide effective to (i) block voltage-gated calcium channels, (ii) bind with high affinity to an omega conopeptide binding site, and (iii) inhibit neurotransmitter release from nervous tissue.

2. The method of claim 1, wherein said effectiveness is within the range of activities measured for omega-conopeptides MVIIA/SNX-111, SNX-199, SNX-236, SNX-239 and TVIA/SNX-185.

3. The method of claim 1, wherein said neurotransmitter is norepinephrine.

4. The method of claim 1, wherein said omega-conopeptide is MVIIA.

5. A method of treating inflammation and associated pain in a subject, in need of said treatment comprising
administering to the subject a pharmacologically effective dose of an omega-conopeptide effective to (i) block voltage-gated calcium channels, (ii) bind with high affinity to an omega conopeptide binding site, and (iii) inhibit neurotransmitter release from nervous tissue.

6. The method of claim 3, wherein said effectiveness in (i) blocking voltage-gated calcium channels, (ii) binding with high affinity to an omega conopeptide binding site, and (iii) inhibiting neurotransmitter release from nervous tissue is within the range of activities measured for omega-conopeptides MVIIA/SNX-111, SNX-199, SNX-236, SNX-239 and TVIA/SNX-185.

7. The method of claim 5, wherein said neurotransmitter release is norepinephrine release.

8. The method of claim 5, wherein said neurotransmitter release is acetylcholine release in a guinea pig ileum preparation.

9. The method of claim 5, wherein said omega-conopeptide is MVIIA.

* * * * *